(12) United States Patent
Haupt et al.

(10) Patent No.: US 9,388,148 B2
(45) Date of Patent: *Jul. 12, 2016

(54) ACYLAMINOCYCLOALKYL COMPOUNDS SUITABLE FOR TREATING DISORDERS THAT RESPOND TO MODULATION OF DOPAMINE D3 RECEPTOR

(71) Applicants: AbbVie Deutschland GmbH & Co. KG, Wiesbaden (DE); AbbVie Inc., North Chicago, IL (US)

(72) Inventors: Andreas Haupt, Ludwigshafen (DE); Jürgen Dinges, North Chicago, IL (US); Liliane Unger, Ludwigshafen (DE); Karsten Wicke, Ludwigshafen (DE); Robert Van Waterschoot, Riehen (CH); Karla Drescher, Ludwigshafen (DE); Ana Relo, Ludwigshafen (DE)

(73) Assignees: AbbVie Inc., North Chicago, IL (US); AbbVie Deutschland GmbH & Co. KG, Wiesbaden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/213,169

(22) Filed: Mar. 14, 2014

(65) Prior Publication Data

US 2014/0303176 A1 Oct. 9, 2014

Related U.S. Application Data

(60) Provisional application No. 61/786,869, filed on Mar. 15, 2013, provisional application No. 61/918,524, filed on Dec. 19, 2013.

(51) Int. Cl.
*C07D 403/04* (2006.01)
*A61K 31/496* (2006.01)
(Continued)

(52) U.S. Cl.
CPC .......... *C07D 295/155* (2013.01); *A61K 31/496* (2013.01); *C07D 239/42* (2013.01); *C07D 403/04* (2013.01)

(58) Field of Classification Search
CPC ............................ C07D 403/04; A61K 31/496
USPC .............. 540/575; 544/295; 514/218, 252.14, 514/252.2
See application file for complete search history.

(56) References Cited

U.S. PATENT DOCUMENTS 7,652,055 B2 1/2010 Galley et al.
2006/0235004 A1 10/2006 Geneste et al.
(Continued)

FOREIGN PATENT DOCUMENTS

WO 2004080981 A1 9/2004
WO 2004/108706 12/2004
(Continued)

OTHER PUBLICATIONS

Le Foil, et al., PubMed Abstract (Expert Opin Investig Drugs, 16(1):45-57), Jan. 2007.*
(Continued)

*Primary Examiner* — Deepak Rao
(74) *Attorney, Agent, or Firm* — Neal Gerber & Eisenberg LLP

(57) ABSTRACT

The present invention relates to novel acylaminocycloalkyl compounds, in particular to the compounds of the formula I as described herein and to their salts and N-oxides. The compounds possess valuable therapeutic properties and are suitable, in particular, for treating diseases that respond to modulation of the dopamine D3 receptor.

(I)

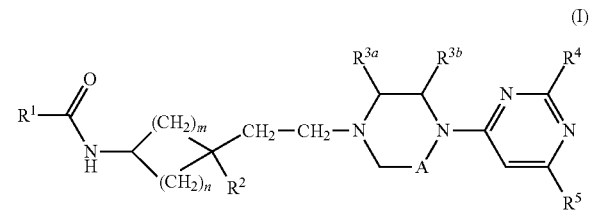

In formula I, the variables have the following meanings:
m is 1 or 2,
n is 1 or 2,
A is selected from the group consisting of $CH_2$, $CH_2CH_2$, $CHFCH_2$ and $CF_2CH_2$,
$R^1$ is an oxygen containing cyclic radical selected such as $C_3$-$C_6$ cycloalkyl, which carries one or two oxygen containing radicals selected from the group consisting of OH, $C_1$-$C_2$-alkoxy, fluorinated $C_1$-$C_2$-alkoxy, and a carbonyl oxygen,
$R^2$ is selected from the group consisting of hydrogen, OH and fluorine,
$R^{3a}$ is selected from the group consisting of hydrogen and methyl,
$R^{3b}$ is selected from the group consisting of hydrogen and methyl,
$R^4$ is branched $C_4$-$C_6$ alkyl or branched fluorinated $C_4$-$C_6$ alkyl, and
$R^5$ is inter alia $C_1$-$C_6$ alkyl, fluorinated $C_1$-$C_3$ alkyl, $C_1$-$C_2$-alkoxy-$C_1$-$C_4$-alkyl, fluorinated $C_1$-$C_2$-alkoxy-$C_1$-$C_4$-alkyl, hydroxy-$C_1$-$C_4$-alkyl, fluorinated hydroxy-$C_1$-$C_4$-alkyl, oxetanyl, fluorinated oxetanyl, oxolanyl, fluorinated oxolanyl, $C_3$-$C_5$ cycloalkyl, fluorinated $C_3$-$C_5$ cycloalkyl, etc.

6 Claims, No Drawings

(51) Int. Cl.
  *C07D 295/155* (2006.01)
  *C07D 239/42* (2006.01)

(56) References Cited

U.S. PATENT DOCUMENTS

| | | | |
|---|---|---|---|
| 2008/0261992 | A1 | 10/2008 | Geneste et al. |
| 2009/0143398 | A1 | 6/2009 | Szalai et al. |
| 2011/0118232 | A1 | 5/2011 | Geneste et al. |
| 2014/0303176 | A1 | 10/2014 | Haupt et al. |

FOREIGN PATENT DOCUMENTS

| | | | |
|---|---|---|---|
| WO | 2005118558 | A2 | 12/2005 |
| WO | 2005118571 | A1 | 12/2005 |
| WO | 2006/015842 | | 2/2006 |
| WO | 2006066885 | A1 | 6/2006 |
| WO | 2006/082456 | | 8/2006 |
| WO | 2007/148208 | | 12/2007 |
| WO | 2008065500 | A2 | 6/2008 |
| WO | 2009/056625 | | 5/2009 |
| WO | 2010034648 | A1 | 4/2010 |
| WO | 2011/161009 | | 12/2011 |
| WO | 2012/004206 | | 1/2012 |
| WO | 2014064038 | | 5/2014 |
| WO | 2014140246 | | 9/2014 |

OTHER PUBLICATIONS

Layzer, Degenerative Diseases of the Nervous System, Cecil Textbook of Medicine, 20th Edition, vol. 2, pp. 2050-2057, 1996.*
Damasio, Alzheimer's Disease and Related Dementias, Cecil Textbook of Medicine, 20th Edition, vol. 2, pp. 1992-1996, 1996.*
Wolff, Some consideration for prodrug design, Burger's Medicinal Chemistry and Drug Discovery, 5th edition, vol. I: Principles and Practice, pp. 975-977, 1995.*
Bundgaard, Design of Prodrugs, p. 1, 1985.*
Banker et al., Prodrugs, Modern Pharmaceutics, Third Edition, Revised and Expanded, pp. 451 and 596, 1996.*
Silverman, Prodrugs and Drug Delivery Systems, The Organic Chemistry of Drug Design and Drug Action, pp. 352-400, 1992.*
Benoit, S.C. et al., "Altered feeding responses in mice with targeted disruption of the dopamine-3 receptor gene," Behav. Neurosci. (2003) 117(1):46-54.
Diaz, G.J. et al., "The [3H]dofetilide binding assay is a predictive screening tool for hERG blockade and proarrhythmia: comparison of intact cell and membrane preparations and effects of altering [K+]o," J. Pharm. Toxicol. Methods (2004) 50:187-199.
Dooley, M. et al., "Pramipexole. A review of its use in the management of early and advanced Parkinson's disease," Drugs & Aging (1998) 12(6):495-514.
Heidbreder, C.A. et al., "The role of central dopamine D3 receptors in drug addiction: a review of pharmacological evidence," Brain Res. Rev. (2005) 49:77-105.
Joyce, J.N., "Dopamine D3 receptor as a therapeutic target for antipsychotic and antiparkinsonian drugs," Pharm & Therap. (2001) 90:231-259.
Laszy, J. et al., "Dopamine D3 receptor antagonists improve the learning performance in memory-impaired rats," Psychopharm. (2005) 179:567-575.
Levant, B. et al., "D3 dopamine receptors in rat spinal cord: implications for sensory and motor function," Neurosci. Lett. (2001) 303:9-12.
Levant, B. et al., "Dopamine D3 receptors. Relevance for the drug treatment of Parkinson's disease," CNS Drugs (1999) 12(6):391-402.
Muhlbauer, B. et al., "Dopamine D3 receptors in the rat kidney: role in physiology and pathophysiology," Acta Physiologica Scandinavica (2000) 168(1):219-223.
Rogoz, Z. et al., "Anxiolytic-like effects of preferential dopamine D3 receptor agonists in an animal model," Polish Journal of Pharmacol. (2003) 55:449-454.
Schwartz, J-C. et al., "The dopamine D3 receptor as a target for antipsychotics," in Novel Antipsychotic Drugs, H.Y. Meltzer, editor, Raven Press, New York (1992) 135-144.
Sokoloff, P. et al., "Molcular cloning and characterization of a novel dopamine receptor (D3) as a target for neuroleptics," Nature (1990) 347:146-151.
Sokoloff, P. et al., "Localization and function of the D3 dopamine receptor," Arzneim. Forsch./Drug Res. (1992) 42 (I):224-230.
Visanji, N.P. et al., "Dopamine D3 receptor stimulation underlies the development of L-DOPA-induced dyskinesia in animal models of Parkinson's disease," Neurobiol. of Disease (2009) 35:184-192.
Berk M., et al., "Dopamine Dysregulation Syndrome: Implications for a Dopamine Hypothesis of Bipolar Disorder," Acta Psychiatrica Scandinavica, 2007, vol. 116 (Suppl. 434), pp. 41-49.
Goldberg J.F., et al., "Preliminary Randomized, Double-Blind, Placebo-Controlled Trial of Pramipexole Added to Mood Stabilizers for Treatment-Resistant Bipolar Depression," American Journal of Pyschiatiy, 2004, vol. 161 (3), pp. 564-566.
Gross M.L., et al., "Renoprotective Effect of a Dopamine D3 Receptor Antagonist in Experimental Type II Diabetes," Laboratory Investigation, 2006, vol. 86 (3), pp. 262-274.
Hori H., et al., "The Efficacy of Pramipexole, a Dopamine Receptor Agonist, as an Adjunctive Treatment in Treatment-Resistant Depression: An Open-Label Trial," The Scientific World Journal, 2012, vol. 2012 Article ID 372474, 8 pages.
Zarate C.A. Jr., et al., "Pramipexole for Bipolar II Depression: A Placebo-Controlled Proof of Concept Study," Biological Psychiatry, 2004, vol. 56 (1), pp. 54-60.
International Search Report for Application No. PCT/EP2013/071947, mailed on Nov. 25, 2013, 3 pages.
Agid Y., et al., "How Can Drug Discovery for Psychiatric Disorders be Improved?," Nature Reviews Drug Discovery, 2007, vol. 6 (3), pp. 189-201.
Belliotti T R., et al., "Novel Cyclohexyl Amides as Potent and Selective D3 Dopamine Receptor Ligands," Bioorganic & Medicinal Chemistry Letters , 1997, vol. 7 (18), pp. 2403-2408.
Bountra C., et al., "Current Understanding, Emerging Therapies and Novel Approaches to Drug Discovery" in: Pain, Marcel Dekker, Inc., 2003, 167 pages.
Brinkmann V., et al., "Fingolimod (FTY720): Discovery and Development of an Oral Drug to Treat Multiple Sclerosis," Nature Reviews Drug Discovery, 2010, vol. 9 (11), pp. 883-897.
Broft A.I., et al., "Bulimia Nervosa and Evidence for Striatal Dopamine Dysregulation: A Conceptual Review," Physiology & Behavior, 2011, vol. 104 (1), pp. 122-127.
Collins I., et al., "Design and Development of Signal Transduction Inhibitors for Cancer Treatment: Experience and Challenges with Kinase Targets," Current Signal Transduction Therapy, 2006, vol. 1, pp. 13-23.
Fairburn C.G., et al., "Eating Disorders," Lancet, 2003, vol. 361 (9355), pp. 407-416.
Frank G.K., et al., "Increased Dopamine D2/D3 Receptor Binding after Recovery from Anorexia Nervosa Measured by Positron Emission Tomography and [11c]Raclopride," Biological Psychiatry, 2005, vol. 58 (11), pp. 908-912.
Girouard H., et al., "Neurovascular Coupling in the Normal Brain and in Hypertension, Stroke and Alzheimer Disease," Journal of Applied Physiology (1985), 2006, vol. 100 (1), pp. 328-335.
Hafenbradl D., et al., "In Vitro Characterization of Small-Molecule Kinase Inhibitors" in: Protein Kinases as Drug Targets, Klebl B., eds., et al., Wiley-VCH Verlag GmbH & Co., Mar. 2011.
International Search Report for Application No. PCT/EP2014/055062, mailed on May 30, 2014, 4 pages.
Joyce J. N., et al., "Dopamine D3 Receptor Agonists for Protection and Repair in Parkinson's Disease," Current Opinion in Pharmacology, 2007, vol. 7 (1), pp. 100-105.
Joyce J.N., et al., "Dopamine D3 Receptor Antagonists as Therapeutic Agents," Drug Discovery Today, 2005, vol. 10 (13), pp. 917-925.
Judge S.I., et al., "Potassium Channel Blockers in Multiple Sclerosis: Neuronal Kv Channels and Effects of Symptomatic Treatment," Pharmacology & Therapeutics, 2006, vol. 111 (1), pp. 224-259.

(56) References Cited

OTHER PUBLICATIONS

Lewitt P. A., "Levodopa for the Treatment of Parkinson's Disease," The New England Journal of Medicine, 2008, vol. 359 (23), pp. 2468-2476.

Mitchell J. D., et al., "Amyotrophic Lateral Sclerosis," Lancet, 2007, vol. 369 (9578), pp. 2031-2041.

Mulert C., et al., "A Ser9Gly Polymorphism in the Dopamine D3 Receptor Gene (DRD3) and Event-Related P300 Potentials," Neuropsychopharmacology, 2006, vol. 31 (6), pp. 1335-1344.

Newman A.H., et al., "Dopamine D3 Receptor Partial Agonists and Antagonists as Potential Drug Abuse Therapeutic Agents," Journal of Medicinal Chemistry, 2005, vol. 48 (11), pp. 3663-3379.

Non-Final Office Action mailed Oct. 21, 2014 for U.S. Appl. No. 14/213,720, filed Mar. 14, 2014.

O'Brien J.T., et al., "Vascular Cognitive Impairment," The Lancet Neurology, 2003, vol. 2 (2), pp. 89-98.

Pettersson-Fernholm K.J., et al., "Dopamine D3 Receptor Gene Polymorphisms, Blood Pressure and Nephropathy in Type 1 Diabetic Patients," Nephrology Dialysis Transplantation, 2004, vol. 19 (6), pp. 1432-1436.

Shah R.S., et al., "Current Approaches in the Treatment of Alzheimer's Disease," Biomedicine & Pharmacotherapy, 2008, vol. 62 (4), pp. 199-207.

Testa B., et al., "Prodrug Design" in: Encyclopedia of Pharmaceutical Technology, 3rd Edition, Swarbrick J., ed., 2007, pp. 3008-3014.

Xi Z.X., et al., "The Novel Dopamine D3 Receptor Antagonist NGB 2904 Inhibits Cocaine's Rewarding Effects and Cocaine-Induced Reinstatement of Drug-Seeking Behavior in Rats," Neuropsychopharmacology, 2006, vol. 31 (7), pp. 1393-1405.

Altinbas, K. et al., "Clinical potential of cariprazine in the treatment of acute mania," Psychiatria Danubina (2013) 25 (3):207-213.

Blakeley S., Eds., Renal Failure and Replacement Therapies, 2008, pp. 26-32.

Citrome, L., "Cariprazine in bipolar disorder: clinical efficacy, tolerability and place in therapy," Adv. Ther. (2013) 30 (2)102-113.

Eduard V., Ed., "Managing Bipolar Disorder in Clinical Practice," in : Overview of Bipolar Disorder, Springer Healthcare Ltd, 2013.

Final Office Action mailed Apr. 1, 2015 for U.S. Appl. No. 14/213,720, filed Mar. 14, 2014.

United States Patent Office Notice of Allowance for U.S. Appl. No. 14/213,720 dated Aug. 18, 2015 (6 pages).

United States Patent Office Action for U.S. Appl. No. 14/213,720 dated Nov. 5, 2015 (9 pages).

United States Patent Office Action for U.S. Appl. No. 14/051,626 dated Aug. 10, 2015 (13 pages).

Lateef A., et al., Unmet Medical Needs in Systemic Lupus Erythematosus, Arthritis Research & Therapy, 2012, 14 (4), pp. 1-9.

Pal S.K., et al., "Emerging Agents in Renal Cell Carcinoma," in: Kidney Cancer Principles and Practice, Lara P.N., eds., Springer Berlin Heidelberg, 2012, pp. 285-301.

Vankayala H., et al., "Renal Cell Carcinoma: Clinical Presentation, Staging, and Prognostic Factors," in: Kidney Cancer Principles and Practice, Lara P.N., et al., eds., Springer Berlin Heidelberg, 2012, pp. 69-88.

Zhu L.J., et al., "Anti-TNF-Therapies in Systemic Lupus Erythematosus," Journal of Biomedicine and Biotechnology, 2010, pp. 1-8.

\* cited by examiner

ACYLAMINOCYCLOALKYL COMPOUNDS SUITABLE FOR TREATING DISORDERS THAT RESPOND TO MODULATION OF DOPAMINE D3 RECEPTOR

CROSS-REFERENCE TO RELATED APPLICATIONS

This claims priority to U.S. Patent Application No. 61/786,869, filed on Mar. 15, 2013, and U.S. Patent Application No. 61/918,524, filed on Dec. 19, 2013, the entire contents of all of which are fully incorporated herein by reference.

BACKGROUND OF THE INVENTION

The present invention relates to novel acylaminocycloalkyl compounds, in particular to the compounds of the formula I as described herein. The compounds possess valuable therapeutic properties and are suitable, in particular, for treating diseases that respond to modulation of the dopamine D3 receptor.

Neurons obtain their information by way of G protein-coupled receptors, inter alia. A large number of substances exert their effect by way of these receptors. One of them is dopamine. Confirmed findings exist with regard to the presence of dopamine and its physiological function as a neurotransmitter. Disorders in the dopaminergic transmitter system result in diseases of the central nervous system which include, for example, schizophrenia, bipolar disorders, depression, Parkinson's disease, disorders associated with drug abuse. These diseases, and others, are treated with drugs which interact with the dopamine receptors.

Up until 1990, two subtypes of dopamine receptor had been clearly defined pharmacologically, termed D1 and D2 receptors. More recently, a third subtype was found, namely, the D3 receptor which appears to mediate some effects of antipsychotics and antiparkinsonian drugs (J. C. Schwartz et al., "The Dopamine $D_3$ Receptor as a Target for Antipsychotics" in Novel Antipsychotic Drugs, H. Y. Meltzer, ed., Raven Press, New York 1992, pages 135-144; M. Dooley et al., Drugs and Aging 1998, 12:495-514; J. N. Joyce, Pharmacology and Therapeutics 2001, 90:231-59, "The Dopamine D3 Receptor as a Therapeutic Target for Antipsychotic and Antiparkinsonian Drugs"). Since then, the dopamine receptors have been divided into two families. On the one hand, there is the D2 group, consisting of D2, D3 and D4 receptors, and, on the other hand, the D1 group, consisting of D1 and D5 receptors.

Whereas D1 and D2 receptors are widely distributed, D3 receptors appear to be expressed regioselectively. Thus, these receptors are preferentially to be found in the limbic system and the projection regions of the mesolimbic dopamine system, especially in the nucleus accumbens, but also in other regions, such as the amygdala. Because of this comparatively regioselective expression, D3 receptors are regarded as being a target having few side-effects and it is assumed that while a selective D3 ligand would have the properties of known antipsychotics, it would not have their dopamine D2 receptor-mediated neurological side-effects (P. Sokoloff et al., Arzneim. Forsch./Drug Res. 42(1):224 (1992), "Localization and Function of the $D_3$ Dopamine Receptor"; P. Sokoloff et al., Nature, 347:146 (1990), "Molecular Cloning and Characterization of a Novel Dopamine Receptor (D3) as a Target for Neuroleptics").

Selective Dopamine D3 receptor ligands have been suggested for the treatment of Parkinson's disease, schizophrenia, depression, motivation disturbances (amotivation) (see J. N. Joyce, Pharmacology and Therapeutics 90, 2001, 231-259; B. Levant, CNS Drugs 1999, 12, 391), for the treatment cognitive dysfunction, in particular cognitive dysfunction associated with schizophrenia or dementia (see J. Laszy et al., Psychopharmacology, 2005, 179, 567-575), for the treatment of disturbances associated with substance abuse, i.e. for the treatment of drug addiction or drug dependence (see J. N. Joyce, loc. cit. and C. A. Heidbreder, Brain Research Reviews 49, 2005, 77-105), for the treatment of anxiety (see Z. Rogoz et al., Polish Journal of Pharmacology, 2003, 55, 449-454), for the treatment of pain (see Levant et al., Neurosci. Lett. 2001, 303, 9), for the treatment of renal function disorders (see B. Mühlbauer, E. Müster, G. Luippold, Acta Physiologica Scandinavica, 2000, 168 (1), 219-223), for the treatment of eating disorders (see S. C. Benoit, J. A. McQuade, D. J. Clegg, M. Xu, P. A. Rushing, S. C. Woods, R. J. Seeley, J. Randy, Behavioral Neuroscience, 2003, 117(1), 46-54) and for the treatment of dyskinesia, especially L-3,4-dihydroxyphenylalanine (L-DOPA) induced dyskinesia (LID) (see Naomi P. Visanji, Susan H. Fox, Tom Johnston, Gabriela Reyes, Mark J. Millan, Jonathan M. Brotchie, Neurobiology of Disease 35 (2009), 184-192).

WO 2006/082456 describes cyclohexylamides, which are Dopamine D3, D2 and 5HT1A antagonists. The cycloalkyl moiety of the compounds of WO 2006/082456 carries an alkylene-N-piperazinyl radical, where the other nitrogen carries a phenyl radical having a fused saturated carbocyclic radical.

Similar compounds are also known from WO 2007/148208, where the fused carbobicyclic radical is replaced by unsubstituted or substituted aryl or hetaryl and where the acyl group requires to be substituted.

Similar compounds are also known from US2009/143398, where the carbobicyclic radical is replaced by a 5,6-dichloro-2-amino-4-pyrimidyl radical.

Similar compounds are also known from WO 2011/161009 and WO 2012/004206, where the carbobicyclic radical is replaced by a 5,6-disubstituted 2-pyridyl radical having a fused heterocycle.

Compounds having a heteroaromatic ring, which is bound via a linker to a piperazine radical carrying a 1-(4-pyrimidinyl)-piperazinyl radical receptor have been described previously in WO 2004/080981, WO2004/108706, WO 2005/118558, WO 2005/118571, WO 2006/015842 and WO 2009/056625. The compounds possess high affinities for the dopamine $D_3$ receptor, and have therefore been proposed as being suitable for treating diseases of the central nervous system.

Although some of the compounds of prior art are known to have high affinities for the Dopamine D3 receptor of less than 10 nM, there is still an ongoing need for compounds which selectively bind to the Dopamine D3 receptor. In particular, there is an ongoing need for compounds which have one of the following characteristics:

i. Selective binding to the Dopamine D3 receptor, in particular vis-à-vis binding to the Dopamine D2 receptor, adrenergic receptors such as alpha-1 or alpha-2 receptors or serotonine type receptors such as serotoninergic 5HT1 and 5HT2 receptors;

ii. metabolic stability, in particular microsomal stability, e.g. measured in vitro, in liver microsomes from various species (e.g. rat or human) in human cells, such as hepatocytes;

iii. no or only low inhibition of cytochrome P450 (CYP) enzymes: cytochrome P450 (CYP) is the name for a superfamily of heme proteins having enzy-matic activity (oxidase). They are also particularly important for the degradation (metabolism) of foreign substances such as drugs or xenobiotics in mammalian organisms. The principal representatives of the types and subtypes of CYP in the human body are: CYP 1A2, CYP 2C9, CYP 2D6 and CYP 3A4. If CYP 3A4 inhibitors (e.g. grapefruit juice, cimetidine, erythro-mycin) are used at the same time as medicinal substances which are degraded by this enzyme system and thus compete for the same binding site on the enzyme, the degradation thereof may be slowed down and thus effects and side effects of the administered medicinal substance may be undesirably enhanced;

iv. a suitable solubility in water (in mg/ml);

v. suitable pharmacokinetics (time course of the concentration of the compound of the invention in plasma or in tissue, for example brain). The pharmacokinetics can be described by the following parameters: half-life, volume of distribution (in $l \cdot kg^{-1}$), plasma clearance (in $l \cdot h^{-1} \cdot kg^{-1}$), AUC (area under the curve, area under the concentration-time curve (in $ng \cdot h \cdot l^{-1}$), oral bioavailability, (the dose-normalized ratio of AUC after oral administration and AUC after intravenous administration), the so-called brain-plasma ratio (the ratio of AUC in brain tissue and AUC in plasma);

vi. no or only low blockade of the hERG channel: compounds which block the hERG channel may cause a prolongation of the QT interval and thus lead to serious disturbances of cardiac rhythm (for example so-called "torsade de pointes"). The potential of compounds to block the hERG channel can be determined by means of the displacement assay with radiolabelled dofetilide which is described in the literature (G. J. Diaz et al., Journal of Pharmacological and Toxicological Methods, 50 (2004), 187-199). A smaller IC50 in this dofetilide assay means a greater probability of potent hERG blockade. In addition, the blockade of the hERG channel can be measured by electro-physiological experiments on cells which have been transfected with the hERG channel, by so-called whole-cell patch clamping (G. J. Diaz et al., Journal of Pharmacological and Toxicological Methods, 50 (2004), 187-199);

vii. high free fraction in brain, i.e. the fraction of the compound bound to proteins should be low;

viii. low lipophilicity.

BRIEF DESCRIPTION OF THE INVENTION

The present invention is thus based on the object of providing compounds which selectively bind to the dopamine D3 receptor at low concentrations.

The compounds are further intended to display at least one of the properties i. to viii. mentioned above, in particular high selectivity with regard to dopamine D3 receptor vs. dopamine D2 receptor, enhanced metabolic stability, in particular microsomal stability, cytosolic stability or hepatocyte stability, low affinity to the HERG receptor, low inhibition of cytochrome P450 (CYP) enzymes, suitable solubility in water and suitable pharmacokinetics.

This object and further objects are achieved by the compounds of the general formula I described below, the N-oxides and the pharmaceutically suitable salts thereof:

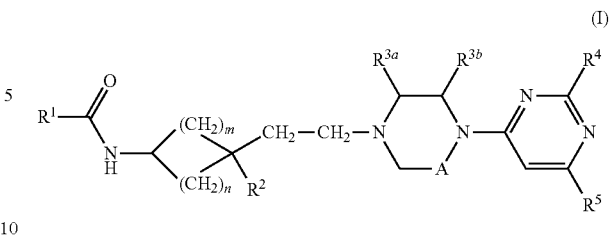

where
m is 1 or 2,
n is 1 or 2,
A is selected from the group consisting of $CH_2$, $CH_2CH_2$, $CHFCH_2$ and $CF_2CH_2$, $R^1$ is an oxygen containing cyclic radical selected from oxetanyl, fluorinated oxetanyl, oxolanyl, fluorinated oxolanyl, $C_3$-$C_6$ cycloalkyl, which carries one or two oxygen containing radical selected from the group consisting of OH, $C_1$-$C_2$-alkoxy, fluorinated $C_1$-$C_2$-alkoxy, and a carbonyl oxygen, and which may additionally carry 1 or 2 radicals selected from fluorine, $C_1$-$C_2$-alkyl and fluorinated $C_1$-$C_2$-alkyl;

$R^2$ is selected from the group consisting of hydrogen and fluorine, $R^{3a}$ is selected from the group consisting of hydrogen and methyl, $R^{3b}$ is selected from the group consisting of hydrogen and methyl, $R^4$ is branched $C_4$-$C_6$ alkyl or branched fluorinated $C_4$-$C_6$ alkyl, and $R^5$ is selected from the group consisting of $C_1$-$C_6$ alkyl, fluorinated $C_1$-$C_3$ alkyl, $C_1$-$C_2$-alkoxy-$C_1$-$C_4$-alkyl, fluorinated $C_1$-$C_2$-alkoxy-$C_1$-$C_4$-alkyl, hydroxy-$C_1$-$C_4$-alkyl, fluorinated hydroxy-$C_1$-$C_4$-alkyl, oxetanyl, fluorinated oxetanyl, oxolanyl, fluorinated oxolanyl, $C_3$-$C_5$ cycloalkyl, fluorinated $C_3$-$C_5$ cycloalkyl, $C_3$-$C_5$ cycloalkyl-$C_1$-$C_4$-alkyl, fluorinated $C_3$-$C_5$ cycloalkyl-$C_1$-$C_4$-alkyl, $C_3$-$C_5$ cycloalkoxy-$C_1$-$C_4$-alkyl and fluorinated $C_3$-$C_5$ cycloalkoxy-$C_1$-$C_4$-alkyl, where the cycloalkyl moiety in the last six mentioned groups of radicals may carry 1 or 2 radicals selected from hydroxyl, $C_1$-$C_2$-alkoxy, fluorinated $C_1$-$C_2$-alkoxy, $C_1$-$C_2$-alkyl and fluorinated $C_1$-$C_2$-alkyl, where the cycloalkoxy moiety in the last two mentioned radicals may carry 1 or 2 radicals selected from hydroxyl, $C_1$-$C_2$-alkoxy, fluorinated $C_1$-$C_2$-alkoxy, $C_1$-$C_2$-alkyl and fluorinated $C_1$-$C_2$-alkyl.

The present invention therefore relates to the compounds of the general formula I, the N-oxides and the pharmaceutically acceptable salts of the compounds of formula I, the prodrugs of the compounds of formula I and the pharmaceutically acceptable salts of said N-oxides and prodrugs of the compounds of formula I. The present invention in particular relates to the compounds of the general formula I and to their pharmaceutically acceptable salts.

The present invention therefore relates to the compounds of the general formula I, the N-oxides and the pharmaceutically acceptable salts of the compounds of formula I, the prodrugs of the compounds of formula I and the pharmaceutically acceptable salts of said N-oxides and prodrugs of the compounds of formula I for the use as a medicament.

The present invention also relates to the compounds of the general formula I, the N-oxides, the pharmaceutically acceptable salts of the compounds of formula I, the prodrugs of the compounds of formula I and the pharmaceutically acceptable salts of said N-oxides or prodrugs of the compounds of formula I for the use in the treatment of a medical disorder susceptible to treatment with a dopamine D3 receptor ligand, in particular from a disorder selected from neurological and psychiatric disorders which can be treated by modulation of the dopamine $D_3$ receptor, in particular by at least partially antagonizing the dopamine D3 receptor.

The compounds of the formula I, their pharmaceutically acceptable salts, their N-oxides and their prodrugs, and the pharmaceutically acceptable salts of said N-oxides or prodrugs selectively bind to the dopamine $D_3$ receptor even at low concentrations, and are in particular at least partial antagonists of the D3 receptor.

They are additionally distinguished by a high selectivity in relation to binding to the dopamine D3 receptor vis-à-vis binding to dopamine D2 receptor or adrenergic or serotonergic receptors such as alpha-1, alpha-2, 5HT1 and 5HT2. The compounds of the invention may additionally have one or more of the above mentioned properties ii. to viii.

The compounds of the formula I, their pharmaceutically acceptable salts, their N-oxides, their prodrugs, and the pharmaceutically acceptable salts of said N-oxides, and prodrugs are therefore particularly suitable for treating disorders and conditions in creatures, especially human creatures, which can be treated or controlled by modulation of the dopamine D3 receptor.

The diseases which respond to the influence of dopamine D3 receptor ligands or agonists include disorders and diseases of the central nervous system, in particular affective disturbances, neurotic disturbances, stress disturbances and somatoform disturbances and psychoses, and especially Parkinson's disease, schizophrenia, major depressive disorder (depression), motivation disturbances, bipolar disorder, disorders related to substance abuse (also termed drug abuse), eating disorders, cognitive dysfunction, in particular cognitive dysfunction associated with schizophrenia or dementia, anxiety, attention deficit disorder with or without hyperactivity, personality disorder and dyskinesia, in particular L-DOPA induced dyskinesia (LID). In addition, D3-mediated diseases may include disturbances of kidney function, i.e. renal function disorders, in particular kidney function disturbances which are caused by diabetes such as diabetes mellitus, also termed as diabetic nephropathy. It may also be possible to ameliorate pain by administering dopamine D3 receptor ligands.

The invention therefore also relates to the use of the compounds of the formula I, their N-oxides, prodrugs and their pharmaceutically acceptable salts and the pharmaceutically acceptable salts of said N-oxides or prodrugs, for the manufacture of a medicament, in particular of a medicament which is suitable for the treatment of a disorder or a condition which can be treated by modulation of the dopamine D3 receptor.

The invention further relates to a medicament, in particular a medicament which is suitable for the treatment of a disorder or a condition which can be treated by modulation of the dopamine D3 receptor and in particular by at least partially antagonizing the dopamine D3 receptor. The medicament comprises at least one compound of the formula I, as described herein, or an N-oxide, or a prodrug of said compound I, or a pharmaceutically acceptable salt of the compound of the formula I or a pharmaceutically acceptable salt of the N-oxide, or the prodrug of compound of the formula I.

DETAILED DESCRIPTION OF THE INVENTION

The terms "compound of the formula I" and "compounds I" are used as synonyms.

The term "prodrugs" means compounds which are metabolized in vivo to the compounds I of the invention. Typical examples of prodrugs are described in C. G. Wermuth (editor): The Practice of Medicinal Chemistry, Academic Press, San Diego, 1996, pages 671-715. These include for example phosphates, carbamates, amino acids, esters, amides, peptides, ureas and the like. Suitable prodrugs in the present case may be for example derivatives of those compounds I carrying an OH group, where the OH group forms an ester linkage, i.e. where the hydrogen atom of the OH group is substituted by a $C_1$-$C_4$-alkylcarbonyl group, e.g. by acetyl, propionyl, n-propylcarbonyl, iso-propylcarbonyl, n-butylcarbonyl or tert-butylcarbonyl (pivaloyl), by benzoyl, or by an acyl group derived from an amino acid, e.g. glycine, alanine, serine, phenylalanine and the like, which is linked to the oxygen or nitrogen of the OH group via the carbonyl group of the amino acid. Further suitable prodrugs are alkylcarbonyloxyalkyl carbonates of compounds I carrying an OH group in which the hydrogen atom of the OH group has been replaced by a group of the formula —C(=O)—O—CHR$^p$—O—C(=O)—R$^q$ in which R$^p$ and R$^q$ are independently of one another $C_1$-$C_4$-alkyl. Such carbonates are described for example in J. Alexander, R. Cargill, S. R. Michelson, H. Schwam, J. Medicinal Chem. 1988, 31(2), 318-322. These groups can then be eliminated under metabolic conditions and result in compounds I. Therefore, said prodrugs and their pharmaceutically acceptable salts are also part of the invention.

The term "pharmaceutically acceptable salts" refers to cationic or anionic salts compounds, wherein the counter ion is derived from pharmaceutically acceptable non-toxic bases or acids including inorganic or organic bases and inorganic or organic acids.

As the compound of formula I or its prodrug, or N-oxide is basic, salts may be prepared from pharmaceutically acceptable non-toxic acids, including inorganic and organic acids. Such acids include acetic, trifluoroacetic acid, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids. It will be understood that, as used herein, references to the compounds of formula I are meant to also include the pharmaceutically acceptable salts.

The compounds of the invention may be in the form of a mixture of diastereomers, or of a mixture of diastereomers in which one of the two diastereomers is enriched, or of essentially diastereomerically pure compounds (diastereomeric excess de >90%). The compounds are preferably in the form of essentially diastereomerically pure compounds (diastereomeric excess de >90%). The compounds I of the invention may furthermore be in the form of a mixture of enantiomers (for example as racemate), of a mixture of enantiomers in which one of the two enantiomers is enriched, or essentially in enantiomerically pure compounds (enantiomeric excess ee >90%). It is preferred to employ the compounds enantiomerically pure or diastereomerically pure.

The present invention moreover relates to compounds as defined herein, wherein one or more of the atoms depicted in formula I have been replaced by a stable isotope (e.g., hydrogen by deuterium, $^{12}$C by $^{13}$C, $^{14}$N by $^{15}$N, $^{16}$O by $^{18}$O) or by an instable isotope (e.g. $^{12}$C by $^{11}$C, $^{16}$O by $^{15}$O, $^{19}$F, by $^{18}$F), preferably by a stable isotope, or enriched with regard to said isotope beyond the natural level. Of course, the compounds according to the invention contain more of the respective isotope than this naturally occurs and thus is anyway present in the compounds I.

The compounds of the formula I and their salts in the solid form may exist in more than one crystal structure (polymorphism), and may also be in the form of hydrates or other solvates. The present invention includes any polymorph of the compound I or its salt as well as any hydrate or other solvate.

In the context of the present description, unless stated otherwise, the terms "alkyl", "fluorinated alkyl", "alkoxy", "fluorinated alkoxy" and radicals derived therefrom, such as "hydroxyalkyl", "alkoxyalkyl", "fluorinated hydroxyalkyl" and "fluorinated alkoxyalkyl", represent groups of individual radicals. The groups of noncyclic radicals "alkyl", "alkoxy", "fluorinated alkoxy", "hydroxyalkyl", "alkoxyalkyl", "fluorinated hydroxyalkyl" and "fluorinated alkoxyalkyl", always include both unbranched and branched "alkyl", "alkoxy", "fluorinated alkoxy", "hydroxyalkyl", "alkoxyalkyl", "fluorinated hydroxyalkyl" and "fluorinated alkoxyalkyl", respectively.

The prefix $C_n$-$C_m$- indicates the respective number of carbons in the hydrocarbon unit. Unless indicated otherwise, fluorinated substituents usually have 1, 2, 3, 4, 5, 6 or 7 fluorine atoms.

Examples of meanings are:

Alkyl, and the alkyl moieties for example in alkoxy, alkoxyalkyl and hydroxyalkyl: saturated, straight-chain or branched hydrocarbon radicals having one or more C atoms, e.g. 1, 2, 3, 4, 5 or 6 carbon atoms. Examples of $C_1$-$C_3$-alkyl are methyl, ethyl, n-propyl and 1-methylethyl.

Branched $C_4$-$C_6$ alkyl is a branched alkyl radical having 4, 5 or 6 carbon atoms. Examples of branched $C_4$-$C_6$-alkyl are 1-methylpropyl, 2-methylpropyl, 1,1-dimethylethyl (=tert.-butyl), 1-methylbutyl, 2-methylbutyl, 3-methylbutyl, 2,2-dimethylpropyl, 1-ethylpropyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Fluorinated alkyl and the alkyl moieties for example in fluorinated alkoxy, fluorinated alkoxyalkyl and fluorinated hydroxyalkyl: saturated, straight-chain or branched hydrocarbon radicals having one or more C atoms, e.g. 1, 2, 3, 4, 5 or 6 carbon atoms, in particular 1 or 2 carbon atoms, where at least one of the hydrogen atoms of the hydrocarbon radical has been replaced by a fluorine atom, examples including fluoromethyl, difluoromethyl, trifluoromethyl, 2-fluoroethyl, 2,2-difluoroethyl, 2,2,2-trifluoroethyl, 1-fluoroethyl, 1,1-difluoroethyl, 1,1,2,2-tetrafluoroethyl, pentafluoroethyl etc.

Branched fluorinated $C_4$-$C_6$ alkyl is a branched alkyl radical having 4, 5 or 6 carbon atoms, as defined above, where at least one of the hydrogen atoms of the branched alkyl radical has been replaced by a fluorine atom, examples including 1-(fluoromethyl)ethyl, 1-(difluoromethyl)ethyl, 1-(trifluoromethyl)ethyl, 1,1,1,3,3,3-hexafluoro-2-propyl, heptafluoro-2-propyl, 1-(fluoromethyl)-1-propyl, 1-(difluoromethyl)-1-propyl, 1-(trifluoromethyl)-1-propyl, 2-(fluoromethyl)-2-propyl, 2-(difluoromethyl)-2-propyl and 2-(trifluoromethyl)-2-propyl.

$C_1$-$C_2$-alkoxy is methoxy and ethoxy.

$C_1$-$C_2$-alkoxy-$C_1$-$C_2$-alkyl is methoxymethyl, ethoxymethyl, 1-methoxyethyl, 2-methoxyethyl, 1-ethoxyethyl and 2-methoxyethyl.

$C_1$-$C_2$-alkoxy-$C_1$-$C_4$-alkyl: $C_1$-$C_2$-alkoxy$C_1$-$C_2$-alkyl as mentioned above and also, for example 2-(methoxy)propyl, 2-(ethoxy)propyl, 3-(methoxy)propyl, 3-(ethoxy)propyl, 2-(methoxy)butyl, 2-(ethoxy)butyl, 3-(methoxy)butyl, 3-(ethoxy)butyl, 4-(methoxy)butyl and 4-(ethoxy)butyl.

Hydroxyalkyl: an alkyl radical ordinarily having 1, 2, 3 or 4 C atoms, in which one hydrogen atom is replaced by an OH radical. Examples thereof are hydroxymethyl, 1-hydroxyethyl, 2-hydroxyethyl, 1-hydroxypropyl, 2-hydroxypropyl, 1-methyl-1-hydroxyethyl, 1-methyl-2-hydroxyethyl, 3-hydroxypropyl, 2-hydroxybutyl, 3-hydroxybutyl, 4-hydroxybutyl, 1-methyl-2-hydroxypropyl, 1,1-dimethyl-2-hydroxyetyl, 1-methyl-1-hydroxypropyl etc.

Fluorinated alkoxy is an alkoxy radical as described above, in which the hydrogen atoms of these groups are partly or completely replaced by fluorine atoms, i.e. for example fluorinated $C_1$-$C_2$-alkoxy, such as fluoromethoxy, difluoromethoxy, trifluoromethoxy, 2-fluoroethoxy, 2,2-difluoroethoxy, 2,2,2-trifluoroethoxy, 1,1,2,2-terafluoroethoxy and pentafluoro-ethoxy.

Fluorinated alkoxyalkyl is an alkoxyalkyl radical as described above, in which the hydrogen atoms of the alkoxy part and/or of the alkyl part are partly or completely replaced by fluorine atoms, i.e. for example fluorinated $C_1$-$C_2$-alkoxy-$C_1$-$C_2$-alkyl-, such as fluoromethoxymethyl, difluoromethoxymethyl, trifluoromethoxymethyl, 2-fluoroethoxymethyl, 2,2-difluoromethoxymethyl, 2,2,2-trifluoroethoxymethyl, 1,1,2,2-terafluoroethoxymethyl, pentafluoroethoxymethyl, 1-(fluoromethoxy)ethyl, 1-(difluoromethoxy)ethyl, 1-(trifluoromethoxy)ethyl, 1-(2-fluoroethoxy)ethyl, 1-(2,2-difluoroethoxy)ethyl, 1-(2,2,2-trifluoroethoxy)ethyl, 1-(1,1,2,2-terafluoroethoxy)ethyl, 1-(pentafluoroethoxy)ethyl, 2-(fluoromethoxy)ethyl, 2-(difluoromethoxy)ethyl, 2-(trifluoromethoxy)ethyl, 2-(2-fluoroethoxy)ethyl, 2-(2,2-difluoroethoxy)ethyl, 2-(2,2,2-trifluoroethoxy)ethyl, 2-(1,1,2,2-terafluoroethoxy)ethyl, 2-(pentafluoroethoxy)ethyl, methoxyfluoroethyl, ethoxyfluoro-methyl, methoxydifluoromethyl, ethoxydifluoromethyl, difluoromethoxyfluoroethyl, 2,2,2-trifluoroethoxyfluoromethyl, difluoromethoxydifluoromethyl, 2,2,2-trifluoroethoxydifluoromethyl, 2-methoxy-1-fluoroethyl, 2-ethoxy-1-fluoroethyl, 2-difluoromethoxy-1-fluoroethyl, 2-(2,2-difluoroethoxy)-1-fluoroethyl, 2-(2,2,2-trifluoroethoxy)-1-fluoroethyl, 2-methoxy-1,1-difluoroethyl, 2-ethoxy-1,1-difluoroethyl, 2-difluoromethoxy-1,1-difluoroethyl, 2-(2,2-difluoroethoxy)-1,1-difluoroethyl and 2-(2,2,2-trifluoroethoxy)-1,1-difluoroethyl. Examples of fluorinated $C_1$-$C_2$-alkoxy-$C_1$-$C_4$-alkyl are fluorinated $C_1$-$C_2$-alkoxy-$C_1$-$C_2$-alkyl as defined above and also for example 3-(fluoromethoxy)propyl, 3-(difluoromethoxy)propyl, 3-(trifluoromethoxy)propyl, 3-(2-fluoroethoxy)propyl, 3-(2,2-difluoroethoxy)propyl, 3-(2,2,2-trifluoroethoxy)propyl, 3-(1,1,2,2-terafluoroethoxy)propyl, 3-(pentafluoro-ethoxy)propyl, 2-fluoro-3-methoxypropyl, 2-fluoro-3-ethoxypropyl, 2,2-difluoro-3-methoxypropyl, 3-difluoromethoxy-2,2-difluoropropyl, 2-fluoro-3-(fluoromethoxy)propyl, 4-(fluoromethoxy)butyl, 4-(difluoromethoxy)butyl, 4-(trifluoromethoxy)butyl, 4-(2-fluoroethoxy)butyl, 4-(2,2-difluoroethoxy)butyl, 4-(2,2,2-trifluoroethoxy)butyl, 4-(1,1,2,2-terafluoroethoxy)butyl, 4-(pentafluoro-ethoxy)butyl, 1-fluoro-4-methoxybutyl, 2-fluoro-4-methoxybutyl, 3-fluoro-4-methoxybutyl, 2-fluoro-3-ethoxypropyl, 2-fluoro-3-fluoromethoxy-2-methyl-butyl, 2,2-difluoro-3-methoxybutyl, 4-difluoromethoxy-2,2-difluorobutyl, 2-fluoro-4-(fluoromethoxy)butyl.

$C_3$-$C_6$ cycloalkyl is a cycloaliphatic radical having 3, 4, 5 or 6 carbon atoms as ring members, while $C_3$-$C_5$ cycloalkyl is a cycloaliphatic radical having 3, 4 or 5 carbon atoms as ring members, examples including cyclopropyl, cyclobutyl, cyclopentyl and cyclohexyl.

Fluorinated $C_3$-$C_5$ cycloalkyl is a $C_3$-$C_5$ cycloalkyl radical as defined above, in which the hydrogen atoms of the cycloalkoxy part and/or of the alkyl part are partly or completely replaced by fluorine atoms, examples including 1-fluorocyclopropyl, 2-fluorocyclopropyl, 2,2-difluorocyclopropyl, 1-fluorocyclobutyl, 2-fluorocyclobutyl, 2,2-difluorocyclobutyl, 3-fluorocyclobutyl, 3,3-difluorocyclobutyl, 1-fluorocyclopentyl, 2-fluorocyclopentyl, 3-fluorocyclopentyl, 2,2-difluorocyclopentyl, 2,3-difluorocyclopentyl, etc.

$C_3$-$C_5$ cycloalkyl-$C_1$-$C_4$-alkyl is a $C_1$-$C_4$-alkyl radical as defined above, where one hydrogen atom is replaced by a cycloalkyl radical, examples including cyclopropylme-thyl, cyclobutylmethyl, 1-cyclopropylethyl, 2-cyclopropylethyl, 1-cyclobutylethyl, 2-cyclobutylethyl cyclopentylmethyl, 1-cyclopentylethyl and 2-cyclopentylethyl.

Fluorinated $C_3$-$C_5$ cycloalkyl-$C_1$-$C_4$-alkyl is a $C_3$-$C_5$ cycloalkoxy-$C_1$-$C_4$-alkyl radical as defined above, in which the hydrogen atoms of the cycloalkyl part and/or of the alkyl part are partly or completely replaced by fluorine atoms.

$C_3$-$C_5$ cycloalkoxy-$C_1$-$C_4$-alkyl is a $C_1$-$C_4$-alkyl radical as defined above, where one hydrogen atom is replaced by a cycloalkoxy radical such as cyclopropyloxy, cyclo-butyloxy or cyclopentyloxy, examples including cyclopropoxymethyl, cyclobutoxyme-thyl, 1-cyclopropoxyethyl, 2-cyclopropoxyethyl, 1-cyclobutoxyethyl, 2-cyclobutoxyethyl cyclopentoxymethyl, 1-cyclopentoxyethyl and 2-cyclopentoxyethyl.

Fluorinated $C_3$-$C_5$ cycloalkoxy-$C_1$-$C_4$-alkyl is a $C_3$-$C_5$ cycloalkoxy-$C_1$-$C_4$-alkyl radical as defined above, in which the hydrogen atoms of the cycloalkoxy part and/or of the alkyl part are partly or completely replaced by fluorine atoms.

Examples of oxetanyl include 2-oxetanyl and 3-oxetanyl. Fluorinated oxetanyl includes e.g. 2-fluoro-2-oxethanyl, 3-fluoro-2-oxetanyl, 3,3-difluoro-2-oxetanyl, 2-fluorooxetan-3-yl, 3-fluorooxetan-3-yl and 2,2-difluorooxetan-3-yl.

Examples of oxolanyl include 2-oxolanyl and 3-oxolanyl. Fluorinated oxolanyl includes e.g. 2-fluoro-2-oxolanyl, 3-fluoro-2-oxolanyl, 4-fluoro-2-oxolanyl, 5-fluoro-2-oxolanyl, 2-fluoro-3-oxolanyl, 3-fluoro-3-oxolanyl, 4-fluoro-3-oxolanyl, 5-fluoro-3-oxolanyl, 3,3-difluoro-2-oxolanyl, 4,4-difluoro-2-oxolanyl, 5,5-difluoro-2-oxolanyl, 2,2-difluoro-3-oxolanyl, 4,4-difluoro-3-oxolanyl and 5,5-difluoro-3-oxolanyl.

In relation to their intended use, the variables m, n, A, $R^1$, $R^2$, $R^{3a}$, $R^{3b}$, $R^4$ and $R^5$ in formula I in particular have the following meanings, where these represent, both considered on their own and in combination with at least one other or all, special embodiments of the compounds of the formula I:

In a first group of particular embodiments, $R^1$ in formula I is selected from the group consisting of $C_3$-$C_6$ cycloalkyl, which carries one oxygen containing radical selected from the group consisting of OH, methoxy, and a carbonyl oxygen, and which may additionally carry 1 radical selected from fluorine, $C_1$-$C_2$-alkyl and fluorinated $C_1$-$C_2$-alkyl. More particularly, $R^1$ is selected from the group consisting of $C_3$-$C_6$ cycloalkyl, which carries one hydroxyl group, and which may additionally carry 1 radical selected from fluorine, $C_1$-$C_2$-alkyl and fluorinated $C_1$-$C_2$-alkyl. Particularly preferred examples of $R^1$ include 1-hydroxycyclopropyl, 2-hydroxycyclopropyl, 1-hydroxycyclobutyl, 2-hydroxycyclobutyl, 3-hydroxycyclobutyl, 3-hydroxy-3-(trifluoromethyl)-cyclobutyl, 2-oxocyclobutyl, 3-hydroxycyclopentyl, 2-hydroxycyclopentyl, 3-hydroxycyclohexyl, 4-hydroxycyclohexyl, 4-methoxycyclohexyl and 4-oxocyclohexyl. Especially $R^1$ is cis- or trans-3-hydroxycyclobutyl, cis- or trans-3-hydroxycyclopentyl, cis- or trans-3-hydroxycyclohexyl or cis- or trans-4-hydroxycyclohexyl. In a very special group of embodiments, $R^1$ is trans-4-hydroxycyclohexyl. In another very special group of embodiments $R^1$ is cis-4-hydroxycyclohexyl. In a further very special group of embodiments, $R^1$ is trans-3-hydroxycyclobutyl. In yet a further very special group of embodiments $R^1$ is cis-3-hydroxycyclobutyl.

In a second group of particular embodiments, $R^1$ in formula I is selected from the group consisting of oxetanyl and oxolanyl. More particularly, $R^1$ is selected from the group consisting of 2-oxetanyl and 3-oxetanyl.

$R^2$ is in particular hydrogen.

In a particular group of embodiments, the variable m in formula I is 2.

In another particular group of embodiments, the variable m in formula I is 1.

In a particular group of embodiments, the variable n in formula I is 2.

In a special group of embodiments, the both variables m and n in formula I are 2.

In another special group of embodiments, the both variables m and n in formula I are 1.

In another special group of embodiments, the variable m in formula I is 2 while the variable n is 1.

In particular groups of embodiments of the invention, both $R^{3a}$ and $R^{3b}$ are hydrogen or one of $R^{3a}$ and $R^{3b}$ is methyl, while the other is hydrogen.

In a special group of embodiments of the invention, both $R^{3a}$ and $R^{3b}$ in formula I are hydrogen.

In another special groups of embodiments of the invention one of $R^{3a}$ and $R^{3b}$ in formula I is methyl, while the other is hydrogen.

If $R^{3a}$ is methyl, the carbon atom bearing the radical $R^{3a}$ is an asymmetric centre and thus said carbon atom may adopt either S-configuration or R-configuration. The invention thus relates both to the essentially pure R-enantiomer (enantiomeric excess ee >90%), i.e. to the compounds of formula I, where $R^{3a}$ is methyl and the carbon atom bearing the radical $R^{3a}$ has R-configuration, and to the essentially pure S-enantiomer (enantiomeric excess ee >90%), i.e. to the compounds of formula I, where $R^{3a}$ is methyl and the carbon atom bearing the radical $R^{3a}$ has S-configuration. The invention also relates to racemic mixtures of said R-enantiomer and said S-enantiomer as well as to non-racemic mixtures, which are enriched with regard to either said R-enantiomer or said S-enantiomer.

Likewise, if $R^{3b}$ is methyl, the carbon atom bearing the radical $R^{3b}$ is an asymmetric centre and thus said carbon atom may adopt either S-configuration or R-configuration. The invention thus relates both to the essentially pure R-enantiomer (enantiomeric excess ee >90%), i.e. to the compounds of formula I, where $R^{3b}$ is methyl and the carbon atom bearing the radical $R^{3b}$ has R-configuration, and to the essentially pure S-enantiomer (enantiomeric excess ee >90%), i.e. to the compounds of formula I, where $R^{3b}$ is methyl and the carbon atom bearing the radical $R^{3a}$ has S-configuration. The invention also relates to racemic mixtures of said R-enantiomer and said 5-enantiomer as well as to non-racemic mixtures, which are enriched with regard to either said R-enantiomer or said S-enantiomer.

In particular groups of embodiments, the variable A in formula I is $CH_2$.

In further particular groups of embodiments, the variable A in formula I is $CH_2CH_2$, $CHFCH_2$ or $CF_2CH_2$. If A is $CHF_2CH$, then the $CH_2$-group of A is preferably attached to the nitrogen. If A is $CF_2CH_2$, then the $CH_2$-group of A is preferably attached to the nitrogen. Especially, A is $CH_2$.

In particular groups of embodiments, the variable $R^4$ in formula I is attached to the pyrimidine ring by a tertiary carbon atom such as in tert.-butyl or 2-methyl-2-butyl. In particular, the variable $R^4$ in formula I is tert.-butyl.

A special group 1.1 of embodiments relates to compounds of the formula I, where

A is $CH_2$, $CH_2CH_2$, $CHFCH_2$ or $CF_2CH_2$ and especially $CH_2$;

$R^1$ is 4-hydroxycyclohexyl, 3-hydroxycyclobutyl, or 3-(trifluoromethyl)-3-hydroxycyclobutyl;

$R^2$ is hydrogen;

$R^{3a}$ and $R^{3b}$ are hydrogen or either $R^{3a}$ is methyl and $R^{3b}$ is hydrogen or $R^{3a}$ is hydrogen and $R^{3b}$ is methyl; and $R^4$ is tert-butyl.

A further special group 1.2 of embodiments relates to compounds of the formula I, where A is $CH_2$;

$R^1$ is trans 4-hydroxycyclohexyl or trans 3-hydroxycyclobutyl;

$R^2$ is hydrogen;

$R^{3a}$ and $R^{3b}$ are hydrogen or either $R^{3a}$ is methyl and $R^{3b}$ is hydrogen or $R^{3a}$ is hydrogen and $R^{3b}$ is methyl; and $R^4$ is tert-butyl.

In particular groups of embodiments, especially in the embodiments 1.1 and 1.2, the variable $R^5$ in formula I is preferably selected from the group consisting of $C_1$-$C_6$ alkyl, fluorinated $C_1$-$C_3$ alkyl, and $C_3$-$C_5$ cycloalkyl, which is unsubstituted or carries 1 or 2 radicals selected from fluorine, $C_1$-$C_2$-alkyl and fluorinated $C_1$-$C_2$-alkyl. In these groups of embodiments, $R^5$ is in particular selected from the group consisting of difluoromethyl, trifluoromethyl, isopropyl, tert.-butyl, cyclopropyl, 1-methylcyclopropyl, 1-fluorocyclopropyl, 2-fluorocyclopropyl, 2,2-difluorocyclopropyl, cyclobutyl, 1-fluorocyclobutyl, 3,3-difluorocyclobutyl, and cyclopentyl and even more particularly selected from the group consisting of cyclobutyl, difluoromethyl, trifluoromethyl, isopropyl and tert.-butyl and especially cyclobutyl.

In another particular groups of embodiments, the variable $R^5$ in formula I is selected from the group consisting of $C_1$-$C_2$-alkoxy-$C_1$-$C_2$-alkyl, fluorinated $C_1$-$C_2$-alkoxy-$C_1$-$C_2$-alkyl and hydroxy-$C_1$-$C_4$-alkyl, especially from the group consisting of $C_1$-$C_2$-alkoxy-$C_1$-$C_2$-alkyl and hydroxy-$C_1$-$C_4$-alkyl. In these groups of embodiments, $R^5$ is in particular selected from the group consisting of methoxymethyl, ethoxymethyl, 2-methoxyethyl, difluoromethoxymethyl, 2-(difluoromethoxy)ethyl, trifluoromethoxymethyl, 2-(trifluoromethoxy)ethyl, methoxydifluoromethyl, ethoxydifluoromethyl, 2-methoxy-1,1-difluoroethyl, hydroxymethyl, 2-hydroxyethyl, 2-hydroxypropyl and 2-hydroxy-2-methylpropyl, especially from the group consisting of methoxymethyl, ethoxymethyl, 2-methoxyethyl, 2-hydroxyethyl, 2-hydroxypropyl and 2-hydroxy-2-methylpropyl.

In yet a further particular groups of embodiments, the variable $R^5$ in formula I is selected from the group consisting of oxetanyl, fluorinated oxetanyl, oxolanyl, fluorinated oxolanyl, and $C_3$-$C_5$ cycloalkyl, which carries 1 or 2 radicals selected from hydroxyl, $C_1$-$C_2$-alkoxy and fluorinated $C_1$-$C_2$-alkoxy. In these groups of embodiments, $R^5$ is in particular selected from the group consisting of 2-oxetanyl, 3-oxetanyl, 2-oxolanyl, 3-oxolanyl, 3-methoxycyclobutyl and 3-hydroxycyclobutyl.

A particular group (A) of embodiments of the invention relates to compounds of the formula Ia

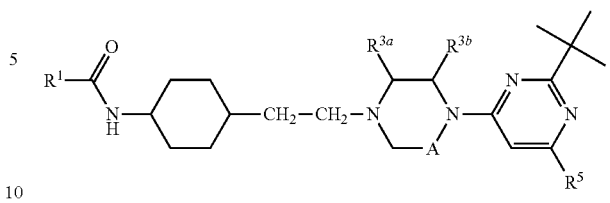

where $R^1$, $R^{3a}$, $R^{3b}$, $R^5$ and A are as defined above, the physiologically tolerated salts of these compounds and the N-oxides thereof.

Another particular group (B) of embodiments of the invention relates to compounds of the formula Ib

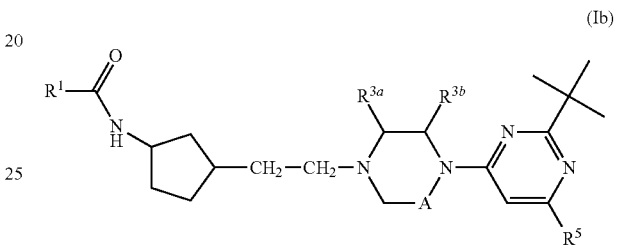

where $R^1$, $R^{3a}$, $R^{3b}$, $R^5$ and A are as defined above, the physiologically tolerated salts of these compounds and the N-oxides thereof.

Another particular group (C) of embodiments of the invention relates to compounds of the formula Ic

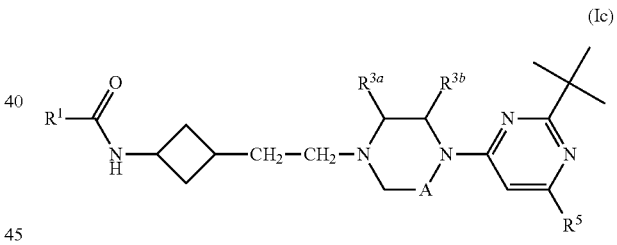

where $R^1$, $R^{3a}$, $R^{3b}$, $R^5$ and A are as defined above, the physiologically tolerated salts of these compounds and the N-oxides thereof.

Special groups A-1.1, B-1.1 and C-1.1 of embodiments relates to compounds of the formulae Ia, Ib and Ic, respectively, where A is $CH_2$, $CH_2CH_2$, $CHFCH_2$ or $CF_2CH_2$, in particular $CH_2$;

$R^1$ is 4-hydroxycyclohexyl, 3-hydroxycyclobutyl, or 3-(trifluoromethyl)-3-hydroxycyclobutyl;

$R^2$ is hydrogen;

$R^{3a}$ and $R^{3b}$ are hydrogen or either $R^{3a}$ is methyl and $R^{3b}$ is hydrogen or $R^{3a}$ is hydrogen and $R^{3b}$ is methyl; and $R^5$ is as defined above.

Further special groups A-1.2, B-1.2 and C-1.2 of embodiments relates to compounds of the formulae Ia, Ib and Ic, respectively, where A is $CH_2$;

$R^1$ is trans 4-hydroxycyclohexyl or trans 3-hydroxycyclobutyl;

$R^2$ is hydrogen;

$R^{3a}$ and $R^{3b}$ are hydrogen or either $R^{3a}$ is methyl and $R^{3b}$ is hydrogen or $R^{3a}$ is hydrogen and $R^{3b}$ is methyl;

$R^4$ is tert-butyl; and $R^5$ is as defined above.

In particular groups of embodiments, especially in the embodiments of groups A-1.1, B-1.1, C-1.1, A-1.2, B-1.2 and C-1.2, the variable $R^5$ in formulae Ia, Ib and Ic is preferably selected from the group consisting of $C_1$-$C_6$ alkyl, fluorinated $C_1$-$C_3$ alkyl, and $C_3$-$C_5$ cycloalkyl, which is unsubstituted or carries 1 or 2 radicals selected from fluorine, $C_1$-$C_2$-alkyl and fluorinated $C_1$-$C_2$-alkyl. In these groups of embodiments, $R^5$ is in particular selected from the group consisting of difluoromethyl, trifluoromethyl, isopropyl, tert.-butyl, cyclopropyl, 1-methylcyclopropyl, 1-fluorocyclopropyl, 2-fluorocyclopropyl, 2,2-difluorocyclopropyl, cyclobutyl, 1-fluorocyclobutyl, 3,3-difluorocyclobutyl, and cyclopentyl and even more particularly selected from the group consisting of cyclobutyl, difluoromethyl, trifluoromethyl, isopropyl and tert.-butyl and especially cyclobutyl.

In another particular groups of embodiments, especially in the embodiments of groups A-1.1, B-1.1, C-1.1, A-1.2, B-1.2 and C-1.2, the variable $R^5$ in formulae Ia, Ib and Ic is selected from the group consisting of $C_1$-$C_2$-alkoxy-$C_1$-$C_2$-alkyl, fluorinated $C_1$-$C_2$-alkoxy-$C_1$-$C_2$-alkyl and hydroxy-$C_1$-$C_4$-alkyl, especially from the group consisting of $C_1$-$C_2$-alkoxy-$C_1$-$C_2$-alkyl and hydroxy-$C_1$-$C_4$-alkyl. In these groups of embodiments, $R^5$ is in particular selected from the group consisting of methoxymethyl, ethoxymethyl, 2-methoxyethyl, difluoromethoxymethyl, 2-(difluoromethoxy)ethyl, trifluoromethoxymethyl, 2-(trifluoromethoxy)ethyl, methoxydifluoromethyl, ethoxydifluoromethyl, 2-methoxy-1,1-difluoroethyl, hydroxymethyl, 2-hydroxyethyl, 2-hydroxypropyl and 2-hydroxy-2-methylpropyl, especially from the group consisting of methoxymethyl, ethoxymethyl, 2-methoxyethyl, 2-hydroxyethyl, 2-hydroxypropyl and 2-hydroxy-2-methylpropyl.

In yet a further particular groups of embodiments, especially in the embodiments of groups A-1.1, B-1.1, C-1.1, A-1.2, B-1.2 and C-1.2, the variable $R^5$ in formulae Ia, Ib and Ic is selected from the group consisting of oxetanyl, fluorinated oxetanyl, oxolanyl, fluorinated oxolanyl, and $C_3$-$C_5$ cycloalkyl, which carries 1 or 2 radicals selected from hydroxyl, $C_1$-$C_2$-alkoxy and fluorinated $C_1$-$C_2$-alkoxy. In these groups of embodiments, $R^5$ is in particular selected from the group consisting of 2-oxetanyl, 3-oxetanyl, 2-oxolanyl, 3-oxolanyl, 3-methoxycyclobutyl and 3-hydroxycyclobutyl.

More particularly, $R^5$ in formula I and likewise in formulae Ia, Ib and Ic and especially in the embodiments of groups A-1.1, B-1.1, C-1.1, A-1.2, B-1.2 and C-1.2, is cyclobutyl, difluoromethyl, trifluoromethyl, isopropyl and tert.-butyl. Especially, $R^5$ in formula I and likewise in formulae Ia, Ib and Ic especially in the embodiments of groups A-1.1, B-1.1, C-1.1, A-1.2, B-1.2 and C-1.2, is cyclobutyl.

In formula I and likewise in formulae Ia, Ib and Ic, the radical $R^1$—C(=O)—NH and the radical $R^2$ be located either cis or trans with respect to each other. The invention thus relates both to the essentially pure cis-isomer (cis/trans ratio is at least 9:1) and to the essentially pure trans-isomer (cis/trans ratio is at most 1:9) and. The invention also relates to mixtures of said cis-isomer and said trans isomer where the cis/trans ratio is from 1:9 to 9:1.

In a particular group of embodiments, the radical $R^1$—C(=O)—NH and the radical $R^2$ predominately adopt cis-configuration. In this embodiment, the cis/trans-ratio is at least 8:1, in particular at least 9:1 and especially at least 95:5.

In another particular group of embodiments, the radical $R^1$—C(=O)—NH and the radical $R^2$ predominately adopt trans-configuration. In this embodiment, the cis/trans-ratio is at most 1:8, in particular at most 1:9 and especially at most 5:95.

Examples of compounds according to the present invention include but are not limited to the compounds of the formulae Ia, Ib, and Ic summarized in the following tables 1 to 36, where $R^1$, $R^{3a}$, $R^{3b}$ and $R^5$ are as defined in one row of table A. In table A, rows $R^{3a}$ and $R^{3b}$, the prefixes (S), (R) and (rac) indicate, whether the compound is the essentially pure R- or S-enantiomer or whether the compound is racemic.

Table 1: Compounds of the formula Ia, where A is $CH_2$ and where $R^1$, $R^{3a}$, $R^{3b}$ and $R^5$ are as defined in one row of table A.

Table 2: Compounds of the formula Ia, where A is $CH_2CH_2$ and where $R^1$, $R^{3a}$, $R^{3b}$ and $R^5$ are as defined in one row of table A.

Table 3: Compounds of the formula Ia, where A is $CF_2CH_2$, where the $CH_2$ group of $CF_2CH_2$ is attached to the nitrogen and where $R^1$, $R^{3a}$, $R^{3b}$ and $R^5$ are as defined in one row of table A.

Table 4: Compounds of the formula Ia, where A is $CHFCH_2$, where the $CH_2$ group of $CHFCH_2$ is attached to the nitrogen and where $R^1$, $R^{3a}$, $R^{3b}$ and $R^5$ are as defined in one row of table A.

Table 5: Compounds of the formula Ia, where A is $CH_2$ and where $R^1$, $R^{3a}$, $R^{3b}$ and $R^5$ are as defined in one row of table A and where the substituents on 1,4-cyclohexadiyl radical adopt cis-configuration.

Table 6: Compounds of the formula Ia, where A is A is $CH_2CH_2$ and where $R^1$, $R^{3a}$, $R^{3b}$ and $R^5$ are as defined in one row of table A and where the substituents on the 1,4-cyclohexadiyl radical predominately adopt cis-configuration.

Table 7: Compounds of the formula Ia, where A is $CF_2CH_2$, where the $CH_2$ group of $CF_2CH_2$ is attached to the nitrogen and where $R^1$, $R^{3a}$, $R^{3b}$ and $R^5$ are as defined in one row of table A and where the substituents on the 1,4-cyclohexadiyl radical predominately adopt cis-configuration.

Table 8: Compounds of the formula Ia, where A is $CHFCH_2$, where the $CH_2$ group of $CHFCH_2$ is attached to the nitrogen and where $R^1$, $R^{3a}$, $R^{3b}$ and $R^5$ are as defined in one row of table A and where the substituents on the 1,4-cyclohexadiyl radical predominately adopt cis-configuration.

Table 9 Compounds of the formula Ia, where A is $CH_2$ and where $R^1$, $R^{3a}$, $R^{3b}$ and $R^5$ are as defined in one row of table A and where the substituents on the 1,4-cyclohexadiyl radical predominately adopt trans-configuration.

Table 10: Compounds of the formula Ia, where A is A is $CH_2CH_2$ and where $R^1$, $R^{3a}$, $R^{3b}$ and $R^5$ are as defined in one row of table A and where the substituents on the 1,4-cyclohexadiyl radical predominately adopt trans-configuration.

Table 11: Compounds of the formula Ia, where A is $CF_2CH_2$, where the $CH_2$ group of $CF_2CH_2$ is attached to the nitrogen and where $R^1$, $R^{3a}$, $R^{3b}$ and $R^5$ are as defined in one row of table A and where the substituents on the 1,4-cyclohexadiyl radical predominately adopt trans-configuration.

Table 12: Compounds of the formula Ia, where A is $CHFCH_2$, where the $CH_2$ group of $CHFCH_2$ is attached to the nitrogen and where $R^1$, $R^{3a}$, $R^{3b}$ and $R^5$ are as defined in one row of table A and where the substituents on the 1,4-cyclohexadiyl radical predominately adopt trans-configuration.

Table 13: Compounds of the formula Ib, where A is $CH_2$ and where $R^1$, $R^{3a}$, $R^{3b}$ and $R^5$ are as defined in one row of table A.

Table 14: Compounds of the formula Ib, where A is CH$_2$CH$_2$ and where R$^1$, R$^{3a}$, R$^{3b}$ and R$^5$ are as defined in one row of table A.

Table 15: Compounds of the formula Ib, where A is CF$_2$CH$_2$, where the CH$_2$ group of CF$_2$CH$_2$ is attached to the nitrogen and where R$^1$, R$^{3a}$, R$^{3b}$ and R$^5$ are as defined in one row of table A.

Table 16: Compounds of the formula Ib, where A is CHFCH$_2$, where the CH$_2$ group of CHFCH$_2$ is attached to the nitrogen and where R$^1$, R$^{3a}$, R$^{3b}$ and R$^5$ are as defined in one row of table A.

Table 17: Compounds of the formula Ib, where A is CH$_2$ and where R$^1$, R$^{3a}$, R$^{3b}$ and R$^5$ are as defined in one row of table A and where the substituents on the 1,3-cyclopentadiyl radical predominately adopt cis-configuration.

Table 18: Compounds of the formula Ib, where A is A is CH$_2$CH$_2$ and where R$^1$, R$^{3a}$, R$^{3b}$ and R$^5$ are as defined in one row of table A and where the substituents on the 1,3-cyclopentadiyl radical predominately adopt cis-configuration.

Table 19: Compounds of the formula Ib, where A is CF$_2$CH$_2$, where the CH$_2$ group of CF$_2$CH$_2$ is attached to the nitrogen and where R$^1$, R$^{3a}$, R$^{3b}$ and R$^5$ are as defined in one row of table A and where the substituents on the 1,3-cyclopentadiyl radical predominately adopt cis-configuration.

Table 20: Compounds of the formula Ib, where A is CHFCH$_2$, where the CH$_2$ group of CHFCH$_2$ is attached to the nitrogen and where R$^1$, R$^{3a}$, R$^{3b}$ and R$^5$ are as defined in one row of table A and where the substituents on the 1,3-cyclopentadiyl radical predominately adopt cis-configuration.

Table 21: Compounds of the formula Ib, where A is CH$_2$ and where R$^1$, R$^{3a}$, R$^{3b}$ and R$^5$ are as defined in one row of table A and where the substituents on the 1,3-cyclopentadiyl radical predominately adopt trans-configuration.

Table 22: Compounds of the formula Ib, where A is A is CH$_2$CH$_2$ and where R$^1$, R$^{3a}$, R$^{3b}$ and R$^5$ are as defined in one row of table A and where the substituents 1,3-cyclopentadiyl radical predominately adopt trans-configuration.

Table 23: Compounds of the formula Ib, where A is CF$_2$CH$_2$, where the CH$_2$ group of CF$_2$CH$_2$ is attached to the nitrogen and where R$^1$, R$^{3a}$, R$^{3b}$ and R$^5$ are as defined in one row of table A and where the substituents on the 1,3-cyclopentadiyl radical predominately adopt trans-configuration.

Table 24: Compounds of the formula Ib, where A is CHFCH$_2$, where the CH$_2$ group of CHFCH$_2$ is attached to the nitrogen and where R$^1$, R$^{3a}$, R$^{3b}$ and R$^5$ are as defined in one row of table A and where the substituents on the 1,3-cyclopentadiyl radical predominately adopt trans-configuration.

Table 25: Compounds of the formula Ic, where A is CH$_2$ and where R$^1$, R$^{3a}$, R$^{3b}$ and R$^5$ are as defined in one row of table A.

Table 26: Compounds of the formula Ic, where A is CH$_2$CH$_2$ and where R$^1$, R$^{3a}$, R$^{3b}$ and R$^5$ are as defined in one row of table A.

Table 27: Compounds of the formula Ic, where A is CF$_2$CH$_2$, where the CH$_2$ group of CF$_2$CH$_2$ is attached to the nitrogen and where R$^1$, R$^{3a}$, R$^{3b}$ and R$^5$ are as defined in one row of table A.

Table 28: Compounds of the formula Ic, where A is CHFCH$_2$, where the CH$_2$ group of CHFCH$_2$ is attached to the nitrogen and where R$^1$, R$^{3a}$, R$^{3b}$ and R$^5$ are as defined in one row of table A.

Table 29: Compounds of the formula Ic, where A is CH$_2$ and where R$^1$, R$^{3a}$, R$^{3b}$ and R$^5$ are as defined in one row of table A and where the substituents on the 1,3-cyclobutadiyl radical predominately adopt cis-configuration.

Table 30: Compounds of the formula Ic, where A is A is CH$_2$CH$_2$ and where R$^1$, R$^{3a}$, R$^{3b}$ and R$^5$ are as defined in one row of table A and where the substituents on the 1,3-cyclobutadiyl radical predominately adopt cis-configuration.

Table 31: Compounds of the formula Ic, where A is CF$_2$CH$_2$, where the CH$_2$ group of CF$_2$CH$_2$ is attached to the nitrogen and where R$^1$, R$^{3a}$, R$^{3b}$ and R$^5$ are as defined in one row of table A and where the substituents on the 1,3-cyclobutadiyl radical predominately adopt cis-configuration.

Table 32: Compounds of the formula Ic, where A is CHFCH$_2$, where the CH$_2$ group of CHFCH$_2$ is attached to the nitrogen and where R$^1$, R$^{3a}$, R$^{3b}$ and R$^5$ are as defined in one row of table A and where the substituents on the 1,3-cyclobutadiyl radical predominately adopt cis-configuration.

Table 33: Compounds of the formula Ic, where A is CH$_2$ and where R$^1$, R$^{3a}$, R$^{3b}$ and R$^5$ are as defined in one row of table A and where the substituents on the 1,3-cyclobutadiyl radical predominately adopt trans-configuration.

Table 34: Compounds of the formula Ic, where A is A is CH$_2$CH$_2$ and where R$^1$, R$^{3a}$, R$^{3b}$ and R$^5$ are as defined in one row of table A and where the substituents 1,3-cyclobutadiyl radical predominately adopt trans-configuration.

Table 35: Compounds of the formula Ic, where A is CF$_2$CH$_2$, where the CH$_2$ group of CF$_2$CH$_2$ is attached to the nitrogen and where R$^1$, R$^{3a}$, R$^{3b}$ and R$^5$ are as defined in one row of table A and where the substituents on the 1,3-cyclobutadiyl radical predominately adopt trans-configuration.

Table 36: Compounds of the formula Ic, where A is CHFCH$_2$, where the CH$_2$ group of CHFCH$_2$ is attached to the nitrogen and where R$^1$, R$^{3a}$, R$^{3b}$ and R$^5$ are as defined in one row of table A and where the substituents on the 1,3-cyclobutadiyl radical predominately adopt trans-configuration.

TABLE A

| # | R$^1$ | R$^{3a}$ | R$^{3b}$ | R$^5$ |
|---|---|---|---|---|
| 1. | cis-4-hydroxycyclohexyl | H | H | cyclobutyl |
| 2. | cis-4-hydroxycyclohexyl | H | H | 1-methylcyclopropyl |
| 3. | cis-4-hydroxycyclohexyl | H | H | trifluoromethyl |
| 4. | cis-4-hydroxycyclohexyl | H | H | difluoromethyl |
| 5. | cis-4-hydroxycyclohexyl | H | H | 2-propyl |
| 6. | cis-4-hydroxycyclohexyl | H | H | cyclopentyl |
| 7. | cis-4-hydroxycyclohexyl | H | H | 2-methyl-2-propyl |
| 8. | cis-4-hydroxycyclohexyl | H | H | 2-methoxyethyl |
| 9. | cis-4-hydroxycyclohexyl | H | H | methoxymethyl |
| 10. | trans-4-hydroxycyclohexyl | H | H | cyclobutyl |
| 11. | trans-4-hydroxycyclohexyl | H | H | 1-methylcyclopropyl |
| 12. | trans-4-hydroxycyclohexyl | H | H | trifluoromethyl |
| 13. | trans-4-hydroxycyclohexyl | H | H | difluoromethyl |
| 14. | trans-4-hydroxycyclohexyl | H | H | 2-propyl |
| 15. | trans-4-hydroxycyclohexyl | H | H | cyclopentyl |
| 16. | trans-4-hydroxycyclohexyl | H | H | 2-methyl-2-propyl |

TABLE A-continued

| # | R¹ | R³ᵃ | R³ᵇ | R⁵ |
|---|---|---|---|---|
| 17. | trans-4-hydroxycyclohexyl | H | H | 2-methoxyethyl |
| 18. | trans-4-hydroxycyclohexyl | H | H | methoxymethyl |
| 19. | cis-4-hydroxycyclohexyl | H | (rac) CH₃ | cyclobutyl |
| 20. | cis-4-hydroxycyclohexyl | H | (rac) CH₃ | 1-methylcyclopropyl |
| 21. | cis-4-hydroxycyclohexyl | H | (rac) CH₃ | trifluoromethyl |
| 22. | cis-4-hydroxycyclohexyl | H | (rac) CH₃ | difluoromethyl |
| 23. | cis-4-hydroxycyclohexyl | H | (rac) CH₃ | 2-propyl |
| 24. | cis-4-hydroxycyclohexyl | H | (rac) CH₃ | cyclopentyl |
| 25. | cis-4-hydroxycyclohexyl | H | (rac) CH₃ | 2-methyl-2-propyl |
| 26. | cis-4-hydroxycyclohexyl | H | (rac) CH₃ | 2-methoxyethyl |
| 27. | cis-4-hydroxycyclohexyl | H | (rac) CH₃ | methoxymethyl |
| 28. | trans-4-hydroxycyclohexyl | H | (rac) CH₃ | cyclobutyl |
| 29. | trans-4-hydroxycyclohexyl | H | (rac) CH₃ | 1-methylcyclopropyl |
| 30. | trans-4-hydroxycyclohexyl | H | (rac) CH₃ | trifluoromethyl |
| 31. | trans-4-hydroxycyclohexyl | H | (rac) CH₃ | difluoromethyl |
| 32. | trans-4-hydroxycyclohexyl | H | (rac) CH₃ | 2-propyl |
| 33. | trans-4-hydroxycyclohexyl | H | (rac) CH₃ | cyclopentyl |
| 34. | trans-4-hydroxycyclohexyl | H | (rac) CH₃ | 2-methyl-2-propyl |
| 35. | trans-4-hydroxycyclohexyl | H | (rac) CH₃ | 2-methoxyethyl |
| 36. | trans-4-hydroxycyclohexyl | H | (rac) CH₃ | methoxymethyl |
| 37. | cis-4-hydroxycyclohexyl | H | (S) CH₃ | cyclobutyl |
| 38. | cis-4-hydroxycyclohexyl | H | (S) CH₃ | 1-methylcyclopropyl |
| 39. | cis-4-hydroxycyclohexyl | H | (S) CH₃ | trifluoromethyl |
| 40. | cis-4-hydroxycyclohexyl | H | (S) CH₃ | difluoromethyl |
| 41. | cis-4-hydroxycyclohexyl | H | (S) CH₃ | 2-propyl |
| 42. | cis-4-hydroxycyclohexyl | H | (S) CH₃ | cyclopentyl |
| 43. | cis-4-hydroxycyclohexyl | H | (S) CH₃ | 2-methyl-2-propyl |
| 44. | cis-4-hydroxycyclohexyl | H | (S) CH₃ | 2-methoxyethyl |
| 45. | cis-4-hydroxycyclohexyl | H | (S) CH₃ | methoxymethyl |
| 46. | trans-4-hydroxycyclohexyl | H | (S) CH₃ | cyclobutyl |
| 47. | trans-4-hydroxycyclohexyl | H | (S) CH₃ | 1-methylcyclopropyl |
| 48. | trans-4-hydroxycyclohexyl | H | (S) CH₃ | trifluoromethyl |
| 49. | trans-4-hydroxycyclohexyl | H | (S) CH₃ | difluoromethyl |
| 50. | trans-4-hydroxycyclohexyl | H | (S) CH₃ | 2-propyl |
| 51. | trans-4-hydroxycyclohexyl | H | (S) CH₃ | cyclopentyl |
| 52. | trans-4-hydroxycyclohexyl | H | (S) CH₃ | 2-methyl-2-propyl |
| 53. | trans-4-hydroxycyclohexyl | H | (S) CH₃ | 2-methoxyethyl |
| 54. | trans-4-hydroxycyclohexyl | H | (S) CH₃ | methoxymethyl |
| 55. | cis-4-hydroxycyclohexyl | H | (R) CH₃ | cyclobutyl |
| 56. | cis-4-hydroxycyclohexyl | H | (R) CH₃ | 1-methylcyclopropyl |
| 57. | cis-4-hydroxycyclohexyl | H | (R) CH₃ | trifluoromethyl |
| 58. | cis-4-hydroxycyclohexyl | H | (R) CH₃ | difluoromethyl |
| 59. | cis-4-hydroxycyclohexyl | H | (R) CH₃ | 2-propyl |
| 60. | cis-4-hydroxycyclohexyl | H | (R) CH₃ | cyclopentyl |
| 61. | cis-4-hydroxycyclohexyl | H | (R) CH₃ | 2-methyl-2-propyl |
| 62. | cis-4-hydroxycyclohexyl | H | (R) CH₃ | 2-methoxyethyl |
| 63. | cis-4-hydroxycyclohexyl | H | (R) CH₃ | methoxymethyl |
| 64. | trans-4-hydroxycyclohexyl | H | (R) CH₃ | cyclobutyl |
| 65. | trans-4-hydroxycyclohexyl | H | (R) CH₃ | 1-methylcyclopropyl |
| 66. | trans-4-hydroxycyclohexyl | H | (R) CH₃ | trifluoromethyl |
| 67. | trans-4-hydroxycyclohexyl | H | (R) CH₃ | difluoromethyl |
| 68. | trans-4-hydroxycyclohexyl | H | (R) CH₃ | 2-propyl |
| 69. | trans-4-hydroxycyclohexyl | H | (R) CH₃ | cyclopentyl |
| 70. | trans-4-hydroxycyclohexyl | H | (R) CH₃ | 2-methyl-2-propyl |
| 71. | trans-4-hydroxycyclohexyl | H | (R) CH₃ | 2-methoxyethyl |
| 72. | trans-4-hydroxycyclohexyl | H | (R) CH₃ | methoxymethyl |
| 73. | trans-4-hydroxycyclohexyl | (rac) CH₃ | H | cyclobutyl |
| 74. | cis-4-hydroxycyclohexyl | (rac) CH₃ | H | 1-methylcyclopropyl |
| 75. | cis-4-hydroxycyclohexyl | (rac) CH₃ | H | trifluoromethyl |
| 76. | cis-4-hydroxycyclohexyl | (rac) CH₃ | H | difluoromethyl |
| 77. | cis-4-hydroxycyclohexyl | (rac) CH₃ | H | 2-propyl |
| 78. | cis-4-hydroxycyclohexyl | (rac) CH₃ | H | cyclopentyl |
| 79. | cis-4-hydroxycyclohexyl | (rac) CH₃ | H | 2-methyl-2-propyl |
| 80. | cis-4-hydroxycyclohexyl | (rac) CH₃ | H | 2-methoxyethyl |
| 81. | cis-4-hydroxycyclohexyl | (rac) CH₃ | H | methoxymethyl |
| 82. | cis-4-hydroxycyclohexyl | (rac) CH₃ | H | cyclobutyl |
| 83. | trans-4-hydroxycyclohexyl | (rac) CH₃ | H | 1-methylcyclopropyl |
| 84. | trans-4-hydroxycyclohexyl | (rac) CH₃ | H | trifluoromethyl |
| 85. | trans-4-hydroxycyclohexyl | (rac) CH₃ | H | difluoromethyl |
| 86. | trans-4-hydroxycyclohexyl | (rac) CH₃ | H | 2-propyl |
| 87. | trans-4-hydroxycyclohexyl | (rac) CH₃ | H | cyclopentyl |
| 88. | trans-4-hydroxycyclohexyl | (rac) CH₃ | H | 2-methyl-2-propyl |
| 89. | trans-4-hydroxycyclohexyl | (rac) CH₃ | H | 2-methoxyethyl |
| 90. | trans-4-hydroxycyclohexyl | (rac) CH₃ | H | methoxymethyl |
| 91. | cis-4-hydroxycyclohexyl | (S) CH₃ | H | cyclobutyl |
| 92. | cis-4-hydroxycyclohexyl | (S) CH₃ | H | 1-methylcyclopropyl |
| 93. | cis-4-hydroxycyclohexyl | (S) CH₃ | H | trifluoromethyl |
| 94. | cis-4-hydroxycyclohexyl | (S) CH₃ | H | difluoromethyl |

TABLE A-continued

| # | R¹ | R³ᵃ | R³ᵇ | R⁵ |
|---|---|---|---|---|
| 95. | cis-4-hydroxycyclohexyl | (S) CH₃ | H | 2-propyl |
| 96. | cis-4-hydroxycyclohexyl | (S) CH₃ | H | cyclopentyl |
| 97. | cis-4-hydroxycyclohexyl | (S) CH₃ | H | 2-methyl-2-propyl |
| 98. | cis-4-hydroxycyclohexyl | (S) CH₃ | H | 2-methoxyethyl |
| 99. | cis-4-hydroxycyclohexyl | (S) CH₃ | H | methoxymethyl |
| 100. | trans-4-hydroxycyclohexyl | (S) CH₃ | H | cyclobutyl |
| 101. | trans-4-hydroxycyclohexyl | (S) CH₃ | H | 1-methylcyclopropyl |
| 102. | trans-4-hydroxycyclohexyl | (S) CH₃ | H | trifluoromethyl |
| 103. | trans-4-hydroxycyclohexyl | (S) CH₃ | H | difluoromethyl |
| 104. | trans-4-hydroxycyclohexyl | (S) CH₃ | H | 2-propyl |
| 105. | trans-4-hydroxycyclohexyl | (S) CH₃ | H | cyclopentyl |
| 106. | trans-4-hydroxycyclohexyl | (S) CH₃ | H | 2-methyl-2-propyl |
| 107. | trans-4-hydroxycyclohexyl | (S) CH₃ | H | 2-methoxyethyl |
| 108. | trans-4-hydroxycyclohexyl | (S) CH₃ | H | methoxymethyl |
| 109. | cis-4-hydroxycyclohexyl | (R) CH₃ | H | cyclobutyl |
| 110. | cis-4-hydroxycyclohexyl | (R) CH₃ | H | 1-methylcyclopropyl |
| 111. | cis-4-hydroxycyclohexyl | (R) CH₃ | H | trifluoromethyl |
| 112. | cis-4-hydroxycyclohexyl | (R) CH₃ | H | difluoromethyl |
| 113. | cis-4-hydroxycyclohexyl | (R) CH₃ | H | 2-propyl |
| 114. | cis-4-hydroxycyclohexyl | (R) CH₃ | H | cyclopentyl |
| 115. | cis-4-hydroxycyclohexyl | (R) CH₃ | H | 2-methyl-2-propyl |
| 116. | cis-4-hydroxycyclohexyl | (R) CH₃ | H | 2-methoxyethyl |
| 117. | cis-4-hydroxycyclohexyl | (R) CH₃ | H | methoxymethyl |
| 118. | trans-4-hydroxycyclohexyl | (R) CH₃ | H | cyclobutyl |
| 119. | trans-4-hydroxycyclohexyl | (R) CH₃ | H | 1-methylcyclopropyl |
| 120. | trans-4-hydroxycyclohexyl | (R) CH₃ | H | trifluoromethyl |
| 121. | trans-4-hydroxycyclohexyl | (R) CH₃ | H | difluoromethyl |
| 122. | trans-4-hydroxycyclohexyl | (R) CH₃ | H | 2-propyl |
| 123. | trans-4-hydroxycyclohexyl | (R) CH₃ | H | cyclopentyl |
| 124. | trans-4-hydroxycyclohexyl | (R) CH₃ | H | 2-methyl-2-propyl |
| 125. | trans-4-hydroxycyclohexyl | (R) CH₃ | H | 2-methoxyethyl |
| 126. | trans-4-hydroxycyclohexyl | (R) CH₃ | H | methoxymethyl |
| 127. | cis-3-hydroxycyclobutyl | H | H | cyclobutyl |
| 128. | cis-3-hydroxycyclobutyl | H | H | 1-methylcyclopropyl |
| 129. | cis-3-hydroxycyclobutyl | H | H | trifluoromethyl |
| 130. | cis-3-hydroxycyclobutyl | H | H | difluoromethyl |
| 131. | cis-3-hydroxycyclobutyl | H | H | 2-propyl |
| 132. | cis-3-hydroxycyclobutyl | H | H | cyclopentyl |
| 133. | cis-3-hydroxycyclobutyl | H | H | 2-methyl-2-propyl |
| 134. | cis-3-hydroxycyclobutyl | H | H | 2-methoxyethyl |
| 135. | cis-3-hydroxycyclobutyl | H | H | methoxymethyl |
| 136. | trans-3-hydroxycyclobutyl | H | H | cyclobutyl |
| 137. | trans-3-hydroxycyclobutyl | H | H | 1-methylcyclopropyl |
| 138. | trans-3-hydroxycyclobutyl | H | H | trifluoromethyl |
| 139. | trans-3-hydroxycyclobutyl | H | H | difluoromethyl |
| 140. | trans-3-hydroxycyclobutyl | H | H | 2-propyl |
| 141. | trans-3-hydroxycyclobutyl | H | H | cyclopentyl |
| 142. | trans-3-hydroxycyclobutyl | H | H | 2-methyl-2-propyl |
| 143. | trans-3-hydroxycyclobutyl | H | H | 2-methoxyethyl |
| 144. | trans-3-hydroxycyclobutyl | H | H | methoxymethyl |
| 145. | cis-3-hydroxycyclobutyl | H | (rac) CH₃ | cyclobutyl |
| 146. | cis-3-hydroxycyclobutyl | H | (rac) CH₃ | 1-methylcyclopropyl |
| 147. | cis-3-hydroxycyclobutyl | H | (rac) CH₃ | trifluoromethyl |
| 148. | cis-3-hydroxycyclobutyl | H | (rac) CH₃ | difluoromethyl |
| 149. | cis-3-hydroxycyclobutyl | H | (rac) CH₃ | 2-propyl |
| 150. | cis-3-hydroxycyclobutyl | H | (rac) CH₃ | cyclopentyl |
| 151. | cis-3-hydroxycyclobutyl | H | (rac) CH₃ | 2-methyl-2-propyl |
| 152. | cis-3-hydroxycyclobutyl | H | (rac) CH₃ | 2-methoxyethyl |
| 153. | cis-3-hydroxycyclobutyl | H | (rac) CH₃ | methoxymethyl |
| 154. | trans-3-hydroxycyclobutyl | H | (rac) CH₃ | cyclobutyl |
| 155. | trans-3-hydroxycyclobutyl | H | (rac) CH₃ | 1-methylcyclopropyl |
| 156. | trans-3-hydroxycyclobutyl | H | (rac) CH₃ | trifluoromethyl |
| 157. | trans-3-hydroxycyclobutyl | H | (rac) CH₃ | difluoromethyl |
| 158. | trans-3-hydroxycyclobutyl | H | (rac) CH₃ | 2-propyl |
| 159. | trans-3-hydroxycyclobutyl | H | (rac) CH₃ | cyclopentyl |
| 160. | trans-3-hydroxycyclobutyl | H | (rac) CH₃ | 2-methyl-2-propyl |
| 161. | trans-3-hydroxycyclobutyl | H | (rac) CH₃ | 2-methoxyethyl |
| 162. | trans-3-hydroxycyclobutyl | H | (rac) CH₃ | methoxymethyl |
| 163. | cis-3-hydroxycyclobutyl | H | (S) CH₃ | cyclobutyl |
| 164. | cis-3-hydroxycyclobutyl | H | (S) CH₃ | 1-methylcyclopropyl |
| 165. | cis-3-hydroxycyclobutyl | H | (S) CH₃ | trifluoromethyl |
| 166. | cis-3-hydroxycyclobutyl | H | (S) CH₃ | difluoromethyl |
| 167. | cis-3-hydroxycyclobutyl | H | (S) CH₃ | 2-propyl |
| 168. | cis-3-hydroxycyclobutyl | H | (S) CH₃ | cyclopentyl |
| 169. | cis-3-hydroxycyclobutyl | H | (S) CH₃ | 2-methyl-2-propyl |
| 170. | cis-3-hydroxycyclobutyl | H | (S) CH₃ | 2-methoxyethyl |
| 171. | cis-3-hydroxycyclobutyl | H | (S) CH₃ | methoxymethyl |
| 172. | trans-3-hydroxycyclobutyl | H | (S) CH₃ | cyclobutyl |

TABLE A-continued

| # | R¹ | R³ᵃ | R³ᵇ | R⁵ |
|---|---|---|---|---|
| 173. | trans-3-hydroxycyclobutyl | H | (S) CH$_3$ | 1-methylcyclopropyl |
| 174. | trans-3-hydroxycyclobutyl | H | (S) CH$_3$ | trifluoromethyl |
| 175. | trans-3-hydroxycyclobutyl | H | (S) CH$_3$ | difluoromethyl |
| 176. | trans-3-hydroxycyclobutyl | H | (S) CH$_3$ | 2-propyl |
| 177. | trans-3-hydroxycyclobutyl | H | (S) CH$_3$ | cyclopentyl |
| 178. | trans-3-hydroxycyclobutyl | H | (S) CH$_3$ | 2-methyl-2-propyl |
| 179. | trans-3-hydroxycyclobutyl | H | (S) CH$_3$ | 2-methoxyethyl |
| 180. | trans-3-hydroxycyclobutyl | H | (S) CH$_3$ | methoxymethyl |
| 181. | cis-3-hydroxycyclobutyl | H | (R) CH$_3$ | cyclobutyl |
| 182. | cis-3-hydroxycyclobutyl | H | (R) CH$_3$ | 1-methylcyclopropyl |
| 183. | cis-3-hydroxycyclobutyl | H | (R) CH$_3$ | trifluoromethyl |
| 184. | cis-3-hydroxycyclobutyl | H | (R) CH$_3$ | difluoromethyl |
| 185. | cis-3-hydroxycyclobutyl | H | (R) CH$_3$ | 2-propyl |
| 186. | cis-3-hydroxycyclobutyl | H | (R) CH$_3$ | cyclopentyl |
| 187. | cis-3-hydroxycyclobutyl | H | (R) CH$_3$ | 2-methyl-2-propyl |
| 188. | cis-3-hydroxycyclobutyl | H | (R) CH$_3$ | 2-methoxyethyl |
| 189. | cis-3-hydroxycyclobutyl | H | (R) CH$_3$ | methoxymethyl |
| 190. | trans-3-hydroxycyclobutyl | H | (R) CH$_3$ | cyclobutyl |
| 191. | trans-3-hydroxycyclobutyl | H | (R) CH$_3$ | 1-methylcyclopropyl |
| 192. | trans-3-hydroxycyclobutyl | H | (R) CH$_3$ | trifluoromethyl |
| 193. | trans-3-hydroxycyclobutyl | H | (R) CH$_3$ | difluoromethyl |
| 194. | trans-3-hydroxycyclobutyl | H | (R) CH$_3$ | 2-propyl |
| 195. | trans-3-hydroxycyclobutyl | H | (R) CH$_3$ | cyclopentyl |
| 196. | trans-3-hydroxycyclobutyl | H | (R) CH$_3$ | 2-methyl-2-propyl |
| 197. | trans-3-hydroxycyclobutyl | H | (R) CH$_3$ | 2-methoxyethyl |
| 198. | trans-3-hydroxycyclobutyl | H | (R) CH$_3$ | methoxymethyl |
| 199. | cis-3-hydroxycyclobutyl | (rac) CH$_3$ | H | cyclobutyl |
| 200. | cis-3-hydroxycyclobutyl | (rac) CH$_3$ | H | 1-methylcyclopropyl |
| 201. | cis-3-hydroxycyclobutyl | (rac) CH$_3$ | H | trifluoromethyl |
| 202. | cis-3-hydroxycyclobutyl | (rac) CH$_3$ | H | difluoromethyl |
| 203. | cis-3-hydroxycyclobutyl | (rac) CH$_3$ | H | 2-propyl |
| 204. | cis-3-hydroxycyclobutyl | (rac) CH$_3$ | H | cyclopentyl |
| 205. | cis-3-hydroxycyclobutyl | (rac) CH$_3$ | H | 2-methyl-2-propyl |
| 206. | cis-3-hydroxycyclobutyl | (rac) CH$_3$ | H | 2-methoxyethyl |
| 207. | cis-3-hydroxycyclobutyl | (rac) CH$_3$ | H | methoxymethyl |
| 208. | trans-3-hydroxycyclobutyl | (rac) CH$_3$ | H | cyclobutyl |
| 209. | trans-3-hydroxycyclobutyl | (rac) CH$_3$ | H | 1-methylcyclopropyl |
| 210. | trans-3-hydroxycyclobutyl | (rac) CH$_3$ | H | trifluoromethyl |
| 211. | trans-3-hydroxycyclobutyl | (rac) CH$_3$ | H | difluoromethyl |
| 212. | trans-3-hydroxycyclobutyl | (rac) CH$_3$ | H | 2-propyl |
| 213. | trans-3-hydroxycyclobutyl | (rac) CH$_3$ | H | cyclopentyl |
| 214. | trans-3-hydroxycyclobutyl | (rac) CH$_3$ | H | 2-methyl-2-propyl |
| 215. | trans-3-hydroxycyclobutyl | (rac) CH$_3$ | H | 2-methoxyethyl |
| 216. | trans-3-hydroxycyclobutyl | (rac) CH$_3$ | H | methoxymethyl |
| 217. | cis-3-hydroxycyclobutyl | (S) CH$_3$ | H | cyclobutyl |
| 218. | cis-3-hydroxycyclobutyl | (S) CH$_3$ | H | 1-methylcyclopropyl |
| 219. | cis-3-hydroxycyclobutyl | (S) CH$_3$ | H | trifluoromethyl |
| 220. | cis-3-hydroxycyclobutyl | (S) CH$_3$ | H | difluoromethyl |
| 221. | cis-3-hydroxycyclobutyl | (S) CH$_3$ | H | 2-propyl |
| 222. | cis-3-hydroxycyclobutyl | (S) CH$_3$ | H | cyclopentyl |
| 223. | cis-3-hydroxycyclobutyl | (S) CH$_3$ | H | 2-methyl-2-propyl |
| 224. | cis-3-hydroxycyclobutyl | (S) CH$_3$ | H | 2-methoxyethyl |
| 225. | cis-3-hydroxycyclobutyl | (S) CH$_3$ | H | methoxymethyl |
| 226. | trans-3-hydroxycyclobutyl | (S) CH$_3$ | H | cyclobutyl |
| 227. | trans-3-hydroxycyclobutyl | (S) CH$_3$ | H | 1-methylcyclopropyl |
| 228. | trans-3-hydroxycyclobutyl | (S) CH$_3$ | H | trifluoromethyl |
| 229. | trans-3-hydroxycyclobutyl | (S) CH$_3$ | H | difluoromethyl |
| 230. | trans-3-hydroxycyclobutyl | (S) CH$_3$ | H | 2-propyl |
| 231. | trans-3-hydroxycyclobutyl | (S) CH$_3$ | H | cyclopentyl |
| 232. | trans-3-hydroxycyclobutyl | (S) CH$_3$ | H | 2-methyl-2-propyl |
| 233. | trans-3-hydroxycyclobutyl | (S) CH$_3$ | H | 2-methoxyethyl |
| 234. | trans-3-hydroxycyclobutyl | (S) CH$_3$ | H | methoxymethyl |
| 235. | cis-3-hydroxycyclobutyl | (R) CH$_3$ | H | cyclobutyl |
| 236. | cis-3-hydroxycyclobutyl | (R) CH$_3$ | H | 1-methylcyclopropyl |
| 237. | cis-3-hydroxycyclobutyl | (R) CH$_3$ | H | trifluoromethyl |
| 238. | cis-3-hydroxycyclobutyl | (R) CH$_3$ | H | difluoromethyl |
| 239. | cis-3-hydroxycyclobutyl | (R) CH$_3$ | H | 2-propyl |
| 240. | cis-3-hydroxycyclobutyl | (R) CH$_3$ | H | cyclopentyl |
| 241. | cis-3-hydroxycyclobutyl | (R) CH$_3$ | H | 2-methyl-2-propyl |
| 242. | cis-3-hydroxycyclobutyl | (R) CH$_3$ | H | 2-methoxyethyl |
| 243. | cis-3-hydroxycyclobutyl | (R) CH$_3$ | H | methoxymethyl |
| 244. | trans-3-hydroxycyclobutyl | (R) CH$_3$ | H | cyclobutyl |
| 245. | trans-3-hydroxycyclobutyl | (R) CH$_3$ | H | 1-methylcyclopropyl |
| 246. | trans-3-hydroxycyclobutyl | (R) CH$_3$ | H | trifluoromethyl |
| 247. | trans-3-hydroxycyclobutyl | (R) CH$_3$ | H | difluoromethyl |
| 248. | trans-3-hydroxycyclobutyl | (R) CH$_3$ | H | 2-propyl |
| 249. | trans-3-hydroxycyclobutyl | (R) CH$_3$ | H | cyclopentyl |
| 250. | trans-3-hydroxycyclobutyl | (R) CH$_3$ | H | 2-methyl-2-propyl |

TABLE A-continued

| # | R¹ | R³ᵃ | R³ᵇ | R⁵ |
|---|---|---|---|---|
| 251. | trans-3-hydroxycyclobutyl | (R) CH₃ | H | 2-methoxyethyl |
| 252. | trans-3-hydroxycyclobutyl | (R) CH₃ | H | methoxymethyl |
| 253. | 3-hydroxy-3-trifluoro-methylcyclobutyl | H | H | cyclobutyl |
| 254. | 3-hydroxy-3-trifluoro-methylcyclobutyl | H | H | 1-methylcyclopropyl |
| 255. | 3-hydroxy-3-trifluoro-methylcyclobutyl | H | H | trifluoromethyl |
| 256. | 3-hydroxy-3-trifluoro-methylcyclobutyl | H | H | difluoromethyl |
| 257. | 3-hydroxy-3-trifluoro-methylcyclobutyl | H | H | 2-propyl |
| 258. | 3-hydroxy-3-trifluoro-methylcyclobutyl | H | H | cyclopentyl |
| 259. | 3-hydroxy-3-trifluoro-methylcyclobutyl | H | H | 2-methyl-2-propyl |
| 260. | 3-hydroxy-3-trifluoro-methylcyclobutyl | H | H | 2-methoxyethyl |
| 261. | 3-hydroxy-3-trifluoro-methylcyclobutyl | H | H | methoxymethyl |
| 262. | 3-hydroxy-3-trifluoro-methylcyclobutyl | H | (rac) CH₃ | cyclobutyl |
| 263. | 3-hydroxy-3-trifluoro-methylcyclobutyl | H | (rac) CH₃ | 1-methylcyclopropyl |
| 264. | 3-hydroxy-3-trifluoro-methylcyclobutyl | H | (rac) CH₃ | trifluoromethyl |
| 265. | 3-hydroxy-3-trifluoro-methylcyclobutyl | H | (rac) CH₃ | difluoromethyl |
| 266. | 3-hydroxy-3-trifluoro-methylcyclobutyl | H | (rac) CH₃ | 2-propyl |
| 267. | 3-hydroxy-3-trifluoro-methylcyclobutyl | H | (rac) CH₃ | cyclopentyl |
| 268. | 3-hydroxy-3-trifluoro-methylcyclobutyl | H | (rac) CH₃ | 2-methyl-2-propyl |
| 269. | 3-hydroxy-3-trifluoro-methylcyclobutyl | H | (rac) CH₃ | 2-methoxyethyl |
| 270. | 3-hydroxy-3-trifluoro-methylcyclobutyl | H | (rac) CH₃ | methoxymethyl |
| 271. | 3-hydroxy-3-trifluoro-methylcyclobutyl | H | (S) CH₃ | cyclobutyl |
| 272. | 3-hydroxy-3-trifluoro-methylcyclobutyl | H | (S) CH₃ | 1-methylcyclopropyl |
| 273. | 3-hydroxy-3-trifluoro-methylcyclobutyl | H | (S) CH₃ | trifluoromethyl |
| 274. | 3-hydroxy-3-trifluoro-methylcyclobutyl | H | (S) CH₃ | difluoromethyl |
| 275. | 3-hydroxy-3-trifluoro-methylcyclobutyl | H | (S) CH₃ | 2-propyl |
| 276. | 3-hydroxy-3-trifluoro-methylcyclobutyl | H | (S) CH₃ | cyclopentyl |
| 277. | 3-hydroxy-3-trifluoro-methylcyclobutyl | H | (S) CH₃ | 2-methyl-2-propyl |
| 278. | 3-hydroxy-3-trifluoro-methylcyclobutyl | H | (S) CH₃ | 2-methoxyethyl |
| 279. | 3-hydroxy-3-trifluoro-methylcyclobutyl | H | (S) CH₃ | methoxymethyl |
| 280. | 3-hydroxy-3-trifluoro-methylcyclobutyl | H | (R) CH₃ | cyclobutyl |
| 281. | 3-hydroxy-3-trifluoro-methylcyclobutyl | H | (R) CH₃ | 1-methylcyclopropyl |
| 282. | 3-hydroxy-3-trifluoro-methylcyclobutyl | H | (R) CH₃ | trifluoromethyl |
| 283. | 3-hydroxy-3-trifluoro-methylcyclobutyl | H | (R) CH₃ | difluoromethyl |
| 284. | 3-hydroxy-3-trifluoro-methylcyclobutyl | H | (R) CH₃ | 2-propyl |
| 285. | 3-hydroxy-3-trifluoro-methylcyclobutyl | H | (R) CH₃ | cyclopentyl |
| 286. | 3-hydroxy-3-trifluoro-methylcyclobutyl | H | (R) CH₃ | 2-methyl-2-propyl |
| 287. | 3-hydroxy-3-trifluoro-methylcyclobutyl | H | (R) CH₃ | 2-methoxyethyl |
| 288. | 3-hydroxy-3-trifluoro-methylcyclobutyl | H | (R) CH₃ | methoxymethyl |
| 289. | 3-hydroxy-3-trifluoro-methylcyclobutyl | (rac) CH₃ | H | cyclobutyl |
| 290. | 3-hydroxy-3-trifluoro-methylcyclobutyl | (rac) CH₃ | H | 1-methylcyclopropyl |

TABLE A-continued

| # | R¹ | R³ᵃ | R³ᵇ | R⁵ |
|---|---|---|---|---|
| 291. | 3-hydroxy-3-trifluoro-methylcyclobutyl | (rac) CH₃ | H | trifluoromethyl |
| 292. | 3-hydroxy-3-trifluoro-methylcyclobutyl | (rac) CH₃ | H | difluoromethyl |
| 293. | 3-hydroxy-3-trifluoro-methylcyclobutyl | (rac) CH₃ | H | 2-propyl |
| 294. | 3-hydroxy-3-trifluoro-methylcyclobutyl | (rac) CH₃ | H | cyclopentyl |
| 295. | 3-hydroxy-3-trifluoro-methylcyclobutyl | (rac) CH₃ | H | 2-methyl-2-propyl |
| 296. | 3-hydroxy-3-trifluoro-methylcyclobutyl | (rac) CH₃ | H | 2-methoxyethyl |
| 297. | 3-hydroxy-3-trifluoro-methylcyclobutyl | (rac) CH₃ | H | methoxymethyl |
| 298. | 3-hydroxy-3-trifluoro-methylcyclobutyl | (S) CH₃ | H | cyclobutyl |
| 299. | 3-hydroxy-3-trifluoro-methylcyclobutyl | (S) CH₃ | H | 1-methylcyclopropyl |
| 300. | 3-hydroxy-3-trifluoro-methylcyclobutyl | (S) CH₃ | H | trifluoromethyl |
| 301. | 3-hydroxy-3-trifluoro-methylcyclobutyl | (S) CH₃ | H | difluoromethyl |
| 302. | 3-hydroxy-3-trifluoro-methylcyclobutyl | (S) CH₃ | H | 2-propyl |
| 303. | 3-hydroxy-3-trifluoro-methylcyclobutyl | (S) CH₃ | H | cyclopentyl |
| 304. | 3-hydroxy-3-trifluoro-methylcyclobutyl | (S) CH₃ | H | 2-methyl-2-propyl |
| 305. | 3-hydroxy-3-trifluoro-methylcyclobutyl | (S) CH₃ | H | 2-methoxyethyl |
| 306. | 3-hydroxy-3-trifluoro-methylcyclobutyl | (S) CH₃ | H | methoxymethyl |
| 307. | 3-hydroxy-3-trifluoro-methylcyclobutyl | (R) CH₃ | H | cyclobutyl |
| 308. | 3-hydroxy-3-trifluoro-methylcyclobutyl | (R) CH₃ | H | 1-methylcyclopropyl |
| 309. | 3-hydroxy-3-trifluoro-methylcyclobutyl | (R) CH₃ | H | trifluoromethyl |
| 310. | 3-hydroxy-3-trifluoro-methylcyclobutyl | (R) CH₃ | H | difluoromethyl |
| 311. | 3-hydroxy-3-trifluoro-methylcyclobutyl | (R) CH₃ | H | 2-propyl |
| 312. | 3-hydroxy-3-trifluoro-methylcyclobutyl | (R) CH₃ | H | cyclopentyl |
| 313. | 3-hydroxy-3-trifluoro-methylcyclobutyl | (R) CH₃ | H | 2-methyl-2-propyl |
| 314. | 3-hydroxy-3-trifluoro-methylcyclobutyl | (R) CH₃ | H | 2-methoxyethyl |
| 315. | 3-hydroxy-3-trifluoro-methylcyclobutyl | (R) CH₃ | H | methoxymethyl |
| 316. | cis-4-methoxycyclohexyl | H | H | cyclobutyl |
| 317. | cis-4-methoxycyclohexyl | H | H | 1-methylcyclopropyl |
| 318. | cis-4-methoxycyclohexyl | H | H | trifluoromethyl |
| 319. | cis-4-methoxycyclohexyl | H | H | difluoromethyl |
| 320. | cis-4-methoxycyclohexyl | H | H | 2-propyl |
| 321. | cis-4-methoxycyclohexyl | H | H | cyclopentyl |
| 322. | cis-4-methoxycyclohexyl | H | H | 2-methyl-2-propyl |
| 323. | cis-4-methoxycyclohexyl | H | H | 2-methoxyethyl |
| 324. | cis-4-methoxycyclohexyl | H | H | methoxymethyl |
| 325. | trans-4-methoxycyclohexyl | H | H | cyclobutyl |
| 326. | trans-4-methoxycyclohexyl | H | H | 1-methylcyclopropyl |
| 327. | trans-4-methoxycyclohexyl | H | H | trifluoromethyl |
| 328. | trans-4-methoxycyclohexyl | H | H | difluoromethyl |
| 329. | trans-4-methoxycyclohexyl | H | H | 2-propyl |
| 330. | trans-4-methoxycyclohexyl | H | H | cyclopentyl |
| 331. | trans-4-methoxycyclohexyl | H | H | 2-methyl-2-propyl |
| 332. | trans-4-methoxycyclohexyl | H | H | 2-methoxyethyl |
| 333. | trans-4-methoxycyclohexyl | H | H | methoxymethyl |
| 334. | cis-4-methoxycyclohexyl | H | (rac) CH₃ | cyclobutyl |
| 335. | cis-4-methoxycyclohexyl | H | (rac) CH₃ | 1-methylcyclopropyl |
| 336. | cis-4-methoxycyclohexyl | H | (rac) CH₃ | trifluoromethyl |
| 337. | cis-4-methoxycyclohexyl | H | (rac) CH₃ | difluoromethyl |
| 338. | cis-4-methoxycyclohexyl | H | (rac) CH₃ | 2-propyl |
| 339. | cis-4-methoxycyclohexyl | H | (rac) CH₃ | cyclopentyl |
| 340. | cis-4-methoxycyclohexyl | H | (rac) CH₃ | 2-methyl-2-propyl |
| 341. | cis-4-methoxycyclohexyl | H | (rac) CH₃ | 2-methoxyethyl |
| 342. | cis-4-methoxycyclohexyl | H | (rac) CH₃ | methoxymethyl |
| 343. | trans-4-methoxycyclohexyl | H | (rac) CH₃ | cyclobutyl |

TABLE A-continued

| # | R¹ | R³ᵃ | R³ᵇ | R⁵ |
|---|---|---|---|---|
| 344. | trans-4-methoxycyclohexyl | H | (rac) CH₃ | 1-methylcyclopropyl |
| 345. | trans-4-methoxycyclohexyl | H | (rac) CH₃ | trifluoromethyl |
| 346. | trans-4-methoxycyclohexyl | H | (rac) CH₃ | difluoromethyl |
| 347. | trans-4-methoxycyclohexyl | H | (rac) CH₃ | 2-propyl |
| 348. | trans-4-methoxycyclohexyl | H | (rac) CH₃ | cyclopentyl |
| 349. | trans-4-methoxycyclohexyl | H | (rac) CH₃ | 2-methyl-2-propyl |
| 350. | trans-4-methoxycyclohexyl | H | (rac) CH₃ | 2-methoxyethyl |
| 351. | trans-4-methoxycyclohexyl | H | (rac) CH₃ | methoxymethyl |
| 352. | cis-4-methoxycyclohexyl | H | (S) CH₃ | cyclobutyl |
| 353. | cis-4-methoxycyclohexyl | H | (S) CH₃ | 1-methylcyclopropyl |
| 354. | cis-4-methoxycyclohexyl | H | (S) CH₃ | trifluoromethyl |
| 355. | cis-4-methoxycyclohexyl | H | (S) CH₃ | difluoromethyl |
| 356. | cis-4-methoxycyclohexyl | H | (S) CH₃ | 2-propyl |
| 357. | cis-4-methoxycyclohexyl | H | (S) CH₃ | cyclopentyl |
| 358. | cis-4-methoxycyclohexyl | H | (S) CH₃ | 2-methyl-2-propyl |
| 359. | cis-4-methoxycyclohexyl | H | (S) CH₃ | 2-methoxyethyl |
| 360. | cis-4-methoxycyclohexyl | H | (S) CH₃ | methoxymethyl |
| 361. | trans-4-methoxycyclohexyl | H | (S) CH₃ | cyclobutyl |
| 362. | trans-4-methoxycyclohexyl | H | (S) CH₃ | 1-methylcyclopropyl |
| 363. | trans-4-methoxycyclohexyl | H | (S) CH₃ | trifluoromethyl |
| 364. | trans-4-methoxycyclohexyl | H | (S) CH₃ | difluoromethyl |
| 365. | trans-4-methoxycyclohexyl | H | (S) CH₃ | 2-propyl |
| 366. | trans-4-methoxycyclohexyl | H | (S) CH₃ | cyclopentyl |
| 367. | trans-4-methoxycyclohexyl | H | (S) CH₃ | 2-methyl-2-propyl |
| 368. | trans-4-methoxycyclohexyl | H | (S) CH₃ | 2-methoxyethyl |
| 369. | trans-4-methoxycyclohexyl | H | (S) CH₃ | methoxymethyl |
| 370. | cis-4-methoxycyclohexyl | H | (R) CH₃ | cyclobutyl |
| 371. | cis-4-methoxycyclohexyl | H | (R) CH₃ | 1-methylcyclopropyl |
| 372. | cis-4-methoxycyclohexyl | H | (R) CH₃ | trifluoromethyl |
| 373. | cis-4-methoxycyclohexyl | H | (R) CH₃ | difluoromethyl |
| 374. | cis-4-methoxycyclohexyl | H | (R) CH₃ | 2-propyl |
| 375. | cis-4-methoxycyclohexyl | H | (R) CH₃ | cyclopentyl |
| 376. | cis-4-methoxycyclohexyl | H | (R) CH₃ | 2-methyl-2-propyl |
| 377. | cis-4-methoxycyclohexyl | H | (R) CH₃ | 2-methoxyethyl |
| 378. | cis-4-methoxycyclohexyl | H | (R) CH₃ | methoxymethyl |
| 379. | trans-4-methoxycyclohexyl | H | (R) CH₃ | cyclobutyl |
| 380. | trans-4-methoxycyclohexyl | H | (R) CH₃ | 1-methylcyclopropyl |
| 381. | trans-4-methoxycyclohexyl | H | (R) CH₃ | trifluoromethyl |
| 382. | trans-4-methoxycyclohexyl | H | (R) CH₃ | difluoromethyl |
| 383. | trans-4-methoxycyclohexyl | H | (R) CH₃ | 2-propyl |
| 384. | trans-4-methoxycyclohexyl | H | (R) CH₃ | cyclopentyl |
| 385. | trans-4-methoxycyclohexyl | H | (R) CH₃ | 2-methyl-2-propyl |
| 386. | trans-4-methoxycyclohexyl | H | (R) CH₃ | 2-methoxyethyl |
| 387. | trans-4-methoxycyclohexyl | H | (R) CH₃ | methoxymethyl |
| 388. | cis-4-methoxycyclohexyl | (rac) CH₃ | H | cyclobutyl |
| 389. | cis-4-methoxycyclohexyl | (rac) CH₃ | H | 1-methylcyclopropyl |
| 390. | cis-4-methoxycyclohexyl | (rac) CH₃ | H | trifluoromethyl |
| 391. | cis-4-methoxycyclohexyl | (rac) CH₃ | H | difluoromethyl |
| 392. | cis-4-methoxycyclohexyl | (rac) CH₃ | H | 2-propyl |
| 393. | cis-4-methoxycyclohexyl | (rac) CH₃ | H | cyclopentyl |
| 394. | cis-4-methoxycyclohexyl | (rac) CH₃ | H | 2-methyl-2-propyl |
| 395. | cis-4-methoxycyclohexyl | (rac) CH₃ | H | 2-methoxyethyl |
| 396. | cis-4-methoxycyclohexyl | (rac) CH₃ | H | methoxymethyl |
| 397. | trans-4-methoxycyclohexyl | (rac) CH₃ | H | cyclobutyl |
| 398. | trans-4-methoxycyclohexyl | (rac) CH₃ | H | 1-methylcyclopropyl |
| 399. | trans-4-methoxycyclohexyl | (rac) CH₃ | H | trifluoromethyl |
| 400. | trans-4-methoxycyclohexyl | (rac) CH₃ | H | difluoromethyl |
| 401. | trans-4-methoxycyclohexyl | (rac) CH₃ | H | 2-propyl |
| 402. | trans-4-methoxycyclohexyl | (rac) CH₃ | H | cyclopentyl |
| 403. | trans-4-methoxycyclohexyl | (rac) CH₃ | H | 2-methyl-2-propyl |
| 404. | trans-4-methoxycyclohexyl | (rac) CH₃ | H | 2-methoxyethyl |
| 405. | trans-4-methoxycyclohexyl | (rac) CH₃ | H | methoxymethyl |
| 406. | cis-4-methoxycyclohexyl | (S) CH₃ | H | cyclobutyl |
| 407. | cis-4-methoxycyclohexyl | (S) CH₃ | H | 1-methylcyclopropyl |
| 408. | cis-4-methoxycyclohexyl | (S) CH₃ | H | trifluoromethyl |
| 409. | cis-4-methoxycyclohexyl | (S) CH₃ | H | difluoromethyl |
| 410. | cis-4-methoxycyclohexyl | (S) CH₃ | H | 2-propyl |
| 411. | cis-4-methoxycyclohexyl | (S) CH₃ | H | cyclopentyl |
| 412. | cis-4-methoxycyclohexyl | (S) CH₃ | H | 2-methyl-2-propyl |
| 413. | cis-4-methoxycyclohexyl | (S) CH₃ | H | 2-methoxyethyl |
| 414. | cis-4-methoxycyclohexyl | (S) CH₃ | H | methoxymethyl |
| 415. | trans-4-methoxycyclohexyl | (S) CH₃ | H | cyclobutyl |
| 416. | trans-4-methoxycyclohexyl | (S) CH₃ | H | 1-methylcyclopropyl |
| 417. | trans-4-methoxycyclohexyl | (S) CH₃ | H | trifluoromethyl |
| 418. | trans-4-methoxycyclohexyl | (S) CH₃ | H | difluoromethyl |
| 419. | trans-4-methoxycyclohexyl | (S) CH₃ | H | 2-propyl |
| 420. | trans-4-methoxycyclohexyl | (S) CH₃ | H | cyclopentyl |
| 421. | trans-4-methoxycyclohexyl | (S) CH₃ | H | 2-methyl-2-propyl |

TABLE A-continued

| # | R¹ | R³ᵃ | R³ᵇ | R⁵ |
|---|---|---|---|---|
| 422. | trans-4-methoxycyclohexyl | (S) CH₃ | H | 2-methoxyethyl |
| 423. | trans-4-methoxycyclohexyl | (S) CH₃ | H | methoxymethyl |
| 424. | cis-4-methoxycyclohexyl | (R) CH₃ | H | cyclobutyl |
| 425. | cis-4-methoxycyclohexyl | (R) CH₃ | H | 1-methylcyclopropyl |
| 426. | cis-4-methoxycyclohexyl | (R) CH₃ | H | trifluoromethyl |
| 427. | cis-4-methoxycyclohexyl | (R) CH₃ | H | difluoromethyl |
| 428. | cis-4-methoxycyclohexyl | (R) CH₃ | H | 2-propyl |
| 429. | cis-4-methoxycyclohexyl | (R) CH₃ | H | cyclopentyl |
| 430. | cis-4-methoxycyclohexyl | (R) CH₃ | H | 2-methyl-2-propyl |
| 431. | cis-4-methoxycyclohexyl | (R) CH₃ | H | 2-methoxyethyl |
| 432. | cis-4-methoxycyclohexyl | (R) CH₃ | H | methoxymethyl |
| 433. | trans-4-methoxycyclohexyl | (R) CH₃ | H | cyclobutyl |
| 434. | trans-4-methoxycyclohexyl | (R) CH₃ | H | 1-methylcyclopropyl |
| 435. | trans-4-methoxycyclohexyl | (R) CH₃ | H | trifluoromethyl |
| 436. | trans-4-methoxycyclohexyl | (R) CH₃ | H | difluoromethyl |
| 437. | trans-4-methoxycyclohexyl | (R) CH₃ | H | 2-propyl |
| 438. | trans-4-methoxycyclohexyl | (R) CH₃ | H | cyclopentyl |
| 439. | trans-4-methoxycyclohexyl | (R) CH₃ | H | 2-methyl-2-propyl |
| 440. | trans-4-methoxycyclohexyl | (R) CH₃ | H | 2-methoxyethyl |
| 441. | trans-4-methoxycyclohexyl | (R) CH₃ | H | methoxymethyl |
| 442. | 4-oxocyclohexyl | H | H | cyclobutyl |
| 443. | 4-oxocyclohexyl | H | H | 1-methylcyclopropyl |
| 444. | 4-oxocyclohexyl | H | H | trifluoromethyl |
| 445. | 4-oxocyclohexyl | H | H | difluoromethyl |
| 446. | 4-oxocyclohexyl | H | H | 2-propyl |
| 447. | 4-oxocyclohexyl | H | H | cyclopentyl |
| 448. | 4-oxocyclohexyl | H | H | 2-methyl-2-propyl |
| 449. | 4-oxocyclohexyl | H | H | 2-methoxyethyl |
| 450. | 4-oxocyclohexyl | H | H | methoxymethyl |
| 451. | 4-oxocyclohexyl | H | (rac) CH₃ | cyclobutyl |
| 452. | 4-oxocyclohexyl | H | (rac) CH₃ | 1-methylcyclopropyl |
| 453. | 4-oxocyclohexyl | H | (rac) CH₃ | trifluoromethyl |
| 454. | 4-oxocyclohexyl | H | (rac) CH₃ | difluoromethyl |
| 455. | 4-oxocyclohexyl | H | (rac) CH₃ | 2-propyl |
| 456. | 4-oxocyclohexyl | H | (rac) CH₃ | cyclopentyl |
| 457. | 4-oxocyclohexyl | H | (rac) CH₃ | 2-methyl-2-propyl |
| 458. | 4-oxocyclohexyl | H | (rac) CH₃ | 2-methoxyethyl |
| 459. | 4-oxocyclohexyl | H | (rac) CH₃ | methoxymethyl |
| 460. | 4-oxocyclohexyl | H | (S) CH₃ | cyclobutyl |
| 461. | 4-oxocyclohexyl | H | (S) CH₃ | 1-methylcyclopropyl |
| 462. | 4-oxocyclohexyl | H | (S) CH₃ | trifluoromethyl |
| 463. | 4-oxocyclohexyl | H | (S) CH₃ | difluoromethyl |
| 464. | 4-oxocyclohexyl | H | (S) CH₃ | 2-propyl |
| 465. | 4-oxocyclohexyl | H | (S) CH₃ | cyclopentyl |
| 466. | 4-oxocyclohexyl | H | (S) CH₃ | 2-methyl-2-propyl |
| 467. | 4-oxocyclohexyl | H | (S) CH₃ | 2-methoxyethyl |
| 468. | 4-oxocyclohexyl | H | (S) CH₃ | methoxymethyl |
| 469. | 4-oxocyclohexyl | H | (R) CH₃ | cyclobutyl |
| 470. | 4-oxocyclohexyl | H | (R) CH₃ | 1-methylcyclopropyl |
| 471. | 4-oxocyclohexyl | H | (R) CH₃ | trifluoromethyl |
| 472. | 4-oxocyclohexyl | H | (R) CH₃ | difluoromethyl |
| 473. | 4-oxocyclohexyl | H | (R) CH₃ | 2-propyl |
| 474. | 4-oxocyclohexyl | H | (R) CH₃ | cyclopentyl |
| 475. | 4-oxocyclohexyl | H | (R) CH₃ | 2-methyl-2-propyl |
| 476. | 4-oxocyclohexyl | H | (R) CH₃ | 2-methoxyethyl |
| 477. | 4-oxocyclohexyl | H | (R) CH₃ | methoxymethyl |
| 478. | 4-oxocyclohexyl | (rac) CH₃ | H | cyclobutyl |
| 479. | 4-oxocyclohexyl | (rac) CH₃ | H | 1-methylcyclopropyl |
| 480. | 4-oxocyclohexyl | (rac) CH₃ | H | trifluoromethyl |
| 481. | 4-oxocyclohexyl | (rac) CH₃ | H | difluoromethyl |
| 482. | 4-oxocyclohexyl | (rac) CH₃ | H | 2-propyl |
| 483. | 4-oxocyclohexyl | (rac) CH₃ | H | cyclopentyl |
| 484. | 4-oxocyclohexyl | (rac) CH₃ | H | 2-methyl-2-propyl |
| 485. | 4-oxocyclohexyl | (rac) CH₃ | H | 2-methoxyethyl |
| 486. | 4-oxocyclohexyl | (rac) CH₃ | H | methoxymethyl |
| 487. | 4-oxocyclohexyl | (S) CH₃ | H | cyclobutyl |
| 488. | 4-oxocyclohexyl | (S) CH₃ | H | 1-methylcyclopropyl |
| 489. | 4-oxocyclohexyl | (S) CH₃ | H | trifluoromethyl |
| 490. | 4-oxocyclohexyl | (S) CH₃ | H | difluoromethyl |
| 491. | 4-oxocyclohexyl | (S) CH₃ | H | 2-propyl |
| 492. | 4-oxocyclohexyl | (S) CH₃ | H | cyclopentyl |
| 493. | 4-oxocyclohexyl | (S) CH₃ | H | 2-methyl-2-propyl |
| 494. | 4-oxocyclohexyl | (S) CH₃ | H | 2-methoxyethyl |
| 495. | 4-oxocyclohexyl | (S) CH₃ | H | methoxymethyl |
| 496. | 4-oxocyclohexyl | (R) CH₃ | H | cyclobutyl |
| 497. | 4-oxocyclohexyl | (R) CH₃ | H | 1-methylcyclopropyl |
| 498. | 4-oxocyclohexyl | (R) CH₃ | H | trifluoromethyl |
| 499. | 4-oxocyclohexyl | (R) CH₃ | H | difluoromethyl |

TABLE A-continued

| # | R¹ | R³ᵃ | R³ᵇ | R⁵ |
|---|---|---|---|---|
| 500. | 4-oxocyclohexyl | (R) CH₃ | H | 2-propyl |
| 501. | 4-oxocyclohexyl | (R) CH₃ | H | cyclopentyl |
| 502. | 4-oxocyclohexyl | (R) CH₃ | H | 2-methyl-2-propyl |
| 503. | 4-oxocyclohexyl | (R) CH₃ | H | 2-methoxyethyl |
| 504. | 4-oxocyclohexyl | (R) CH₃ | H | methoxymethyl |
| 505. | (rac) cis-3-hydroxycyclohexyl | H | H | cyclobutyl |
| 506. | (rac) cis-3-hydroxycyclohexyl | H | H | 1-methylcyclopropyl |
| 507. | (rac) cis-3-hydroxycyclohexyl | H | H | trifluoromethyl |
| 508. | (rac) cis-3-hydroxycyclohexyl | H | H | difluoromethyl |
| 509. | (rac) cis-3-hydroxycyclohexyl | H | H | 2-propyl |
| 510. | (rac) cis-3-hydroxycyclohexyl | H | H | cyclopentyl |
| 511. | (rac) cis-3-hydroxycyclohexyl | H | H | 2-methyl-2-propyl |
| 512. | (rac) cis-3-hydroxycyclohexyl | H | H | 2-methoxyethyl |
| 513. | (rac) cis-3-hydroxycyclohexyl | H | H | methoxymethyl |
| 514. | (rac) trans-3-hydroxycyclohexyl | H | H | cyclobutyl |
| 515. | (rac) trans-3-hydroxycyclohexyl | H | H | 1-methylcyclopropyl |
| 516. | (rac) trans-3-hydroxycyclohexyl | H | H | trifluoromethyl |
| 517. | (rac) trans-3-hydroxycyclohexyl | H | H | difluoromethyl |
| 518. | (rac) trans-3-hydroxycyclohexyl | H | H | 2-propyl |
| 519. | (rac) trans-3-hydroxycyclohexyl | H | H | cyclopentyl |
| 520. | (rac) trans-3-hydroxycyclohexyl | H | H | 2-methyl-2-propyl |
| 521. | (rac) trans-3-hydroxycyclohexyl | H | H | 2-methoxyethyl |
| 522. | (rac) trans-3-hydroxycyclohexyl | H | H | methoxymethyl |
| 523. | (1S,3R)-3-hydroxycyclohexyl | H | H | cyclobutyl |
| 524. | (1S,3R)-3-hydroxycyclohexyl | H | H | 1-methylcyclopropyl |
| 525. | (1S,3R)-3-hydroxycyclohexyl | H | H | trifluoromethyl |
| 526. | (1S,3R)-3-hydroxycyclohexyl | H | H | difluoromethyl |
| 527. | (1S,3R)-3-hydroxycyclohexyl | H | H | 2-propyl |
| 528. | (1S,3R)-3-hydroxycyclohexyl | H | H | cyclopentyl |
| 529. | (1S,3R)-3-hydroxycyclohexyl | H | H | 2-methyl-2-propyl |
| 530. | (1S,3R)-3-hydroxycyclohexyl | H | H | 2-methoxyethyl |
| 531. | (1S,3R)-3-hydroxycyclohexyl | H | H | methoxymethyl |
| 532. | (1S,3S)-3-hydroxycyclohexyl | H | H | cyclobutyl |
| 533. | (1S,3S)-3-hydroxycyclohexyl | H | H | 1-methylcyclopropyl |
| 534. | (1S,3S)-3-hydroxycyclohexyl | H | H | trifluoromethyl |
| 535. | (1S,3S)-3-hydroxycyclohexyl | H | H | difluoromethyl |
| 536. | (1S,3S)-3-hydroxycyclohexyl | H | H | 2-propyl |
| 537. | (1S,3S)-3-hydroxycyclohexyl | H | H | cyclopentyl |
| 538. | (1S,3S)-3-hydroxycyclohexyl | H | H | 2-methyl-2-propyl |
| 539. | (1S,3S)-3-hydroxycyclohexyl | H | H | 2-methoxyethyl |
| 540. | (1S,3S)-3-hydroxycyclohexyl | H | H | methoxymethyl |
| 541. | (1R,3S)-3-hydroxycyclohexyl | H | H | cyclobutyl |
| 542. | (1R,3S)-3-hydroxycyclohexyl | H | H | 1-methylcyclopropyl |
| 543. | (1R,3S)-3-hydroxycyclohexyl | H | H | trifluoromethyl |
| 544. | (1R,3S)-3-hydroxycyclohexyl | H | H | difluoromethyl |
| 545. | (1R,3S)-3-hydroxycyclohexyl | H | H | 2-propyl |
| 546. | (1R,3S)-3-hydroxycyclohexyl | H | H | cyclopentyl |
| 547. | (1R,3S)-3-hydroxycyclohexyl | H | H | 2-methyl-2-propyl |
| 548. | (1R,3S)-3-hydroxycyclohexyl | H | H | 2-methoxyethyl |
| 549. | (1R,3S)-3-hydroxycyclohexyl | H | H | methoxymethyl |
| 550. | (1R,3R)-3-hydroxycyclohexyl | H | H | cyclobutyl |
| 551. | (1R,3R)-3-hydroxycyclohexyl | H | H | 1-methylcyclopropyl |
| 552. | (1R,3R)-3-hydroxycyclohexyl | H | H | trifluoromethyl |
| 553. | (1R,3R)-3-hydroxycyclohexyl | H | H | difluoromethyl |
| 554. | (1R,3R)-3-hydroxycyclohexyl | H | H | 2-propyl |
| 555. | (1R,3R)-3-hydroxycyclohexyl | H | H | cyclopentyl |
| 556. | (1R,3R)-3-hydroxycyclohexyl | H | H | 2-methyl-2-propyl |
| 557. | (1R,3R)-3-hydroxycyclohexyl | H | H | 2-methoxyethyl |
| 558. | (1R,3R)-3-hydroxycyclohexyl | H | H | methoxymethyl |

The compounds I according to the invention can be prepared by analogy to methods known from the literature. An important approach to the compounds according to the invention is offered by the reaction of a 2-(N-protected aminocycloalkyl)-acetaldehyde compound II with an 4-piperazine-1yl-pyrimidine compound III as depicted in scheme 1.

Scheme 1:

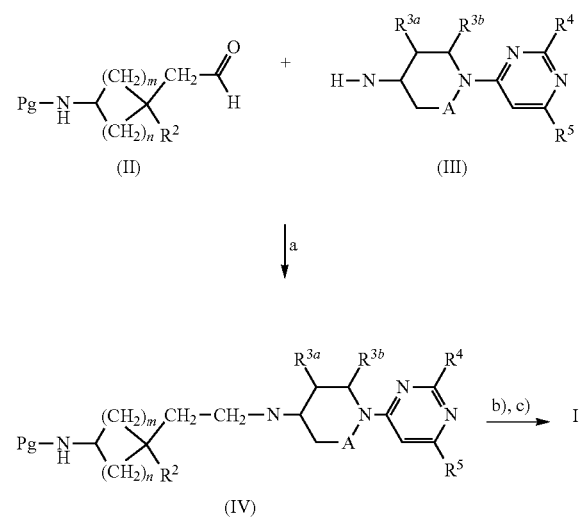

In scheme 1, $R^1$, $R^2$, $R^{3a}$, $R^{3b}$, $R^4$, $R^5$ and A have the aforementioned meanings. Pg is N-protective group which can be cleaved under mild conditions, such as methoxycarbonyl, ethoxycarbonyl, tert-butoxycrbonyl (boc), benzyloxycarbonyl (cbz), 2-trimethylsilylethoxycarbonyl (Teoc) or 9-fluorenylmethoxycaronbyl (fmoc).

In step a) of scheme 1, an aldehyde of the formula (II) is reacted with a compound of formula III under conditions of a reductive amination. Usually a mild reducing agent, e.g. a borohydride such as sodium borohydride, sodium cyanoborohydride or sodium triacetoxyborohydride, is used. The skilled person is familiar with the reaction conditions which are required for a reductive amination, e.g. from Bioorganic and Medicinal Chemistry Lett. 2002, 12(5), pp. 795-798 and 12(7) pp. 1269-1273.

The thus obtained compound of formula IV is deprotected in step b) and reacted in step c) with an acylating agent, e.g. an acyl halide, in particular an acylchloride of the formula $R^1$—C(O)Cl, a carboxylic acid of the formula $R^1$—C(O)OH, a $C_1$-$C_4$-alkyl ester or an anhydride thereof, to yield the compound of the formula I.

Compounds of the formula II are well known, e.g. from WO 2008/125891, or can be prepared by analogy to the methods described in J. Med. Chem. 43, 1878 (2000)

Compounds of the formula III are well known, or can be prepared by analogy to the methods described in WO 99/02503, WO 2004/080981, WO2004/108706, WO 2005/118558, WO 2005/118571 and WO 2009/056625.

A particular approach to compounds of the formula III is shown in scheme 2 below:

Scheme 2:

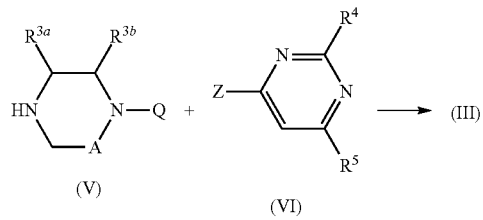

In a first step, a piperazine compound V wherein Q is H or an N-protecting group is reacted with a pyrimidine compound VI wherein Z is halogen to yield a compound of the formula III. This method is known from the prior art cited in the introductory part of the application and also from WO 99/09015 and WO 03/002543.

The preparation of the pyrimidine compounds VI is simply achieved by reacting an amidinium chloride (VIII) with a suitable β-ketoester VII to yield a 4-hydroxypyrimidine of the formula IX which can be transformed to the halo compound VI by reacting it with halogenating agent such as thionyl chloride, phosphoryl chloride, phosphoryl bromide, phosphorous trichloride, phosphorous tribromide or phosphorous pentachloride (see scheme 3):

Scheme 3:

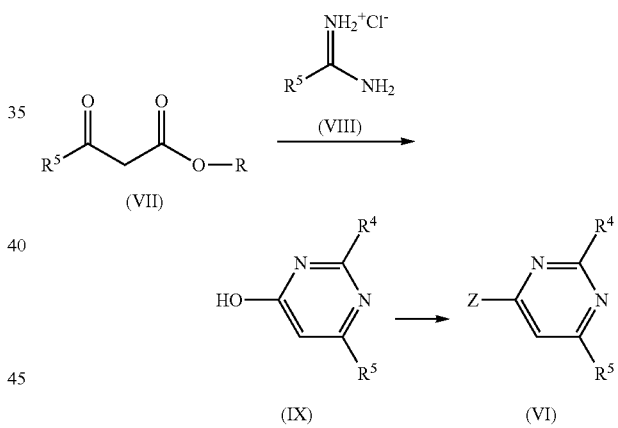

βB-Ketoesters VII can be simply synthesized according to the methods described in this application from the corresponding acid chlorides $R^5$—COCl by reaction with meldrum's acid (2,2-dimethyl-4,6-dioxo-1,3-dioxan) according to the process as described herein and in B. Trost et al., Journal of the American Chemical Society (2002), 124(35): 10396-10415; Paknikar, S. K. et al., Journal of the Indian Institute of Science (2001), 81(2):175-179; and Brummell, David G. et al., Journal of Medicinal Chemistry (2001), 44(1):78-93.

The N-oxides of compound I may be prepared from the compounds of formula I according to conventional oxidation methods, for example by treating said compounds with an organic peracid; such as metachloroperbenzoic acid or 3-chloroperbenzoic acid [Journal of Medicinal Chemistry 38(11), 1892-1903 (1995), WO 03/64572]; or with inorganic oxidizing agents; such as hydrogen peroxide [cf. Journal of Heterocyclic Chemistry 18 (7), 1305-1308 (1981)] or oxone [cf. Journal of the American Chemical Society 123(25), 5962-5973 (2001)]. The oxidation may lead to pure mono-N-oxides or to a mixture of different N-oxides, which can be separated by conventional methods; such as chromatography.

The reactions are usually performed in an organic solvent, including aprotic organic solvent, e.g. substituted amides, lactames and ureas; such as dimethylformamide, dimethylacetamide, N-methylpyrrolidone, tetramethyl urea, cyclic ethers; such as dioxane, tetrahydrofurane, halogenated hydrocarbons; such as dichloromethane, and mixtures thereof as well as mixtures thereof with $C_1$-$C_6$-alkanols and/or water.

The reactions described above will be usually performed at temperatures ranging from –10° C. to 100° C., depending on the reactivity of the used compounds.

The reaction mixtures are worked up in a conventional way, e.g. by mixing with water, separating the phases and, where appropriate, purifying the crude products by chromatography. The intermediates and final products in some cases result in the form of colorless or pale brownish, viscous oils which are freed of volatiles or purified under reduced pressure and at moderately elevated temperature. If the intermediates and final products are obtained as solids, the purification can also take place by recrystallization or digestion.

Due to their capability of selectively binding to the dopamine D3 receptor at low concentrations, in particular at least partially antagonizing the Dopamine D3 receptor, the compounds of the formula I, their N-oxides and their prodrugs and the pharmaceutically acceptable salts thereof, are particularly suitable for treating disorders or conditions, which can be treated by modulation of the dopamine D3 receptor, in particular by at least partially antagonizing the Dopamine D3 receptor. The terms "treating" and "treatment" in terms of the present invention have to be understood to include both curative treatment of the cause of a disease or disorder, the treatment of the symptoms associated with a disease or disorder, i.e. controlling the disease or disorder or ameliorating the conditions or symptoms associated with a disease or disorder, and prophylactic treatment, i.e. a treatment for reducing the risk of a disease or disorder.

Neurological and psychiatric disorders or conditions which can be treated by dopamine D3 receptor ligands, including curative treatment, control or amelioration and prophylaxis, include CNS disorders, in particular schizophrenia, depression, motivation disturbances, bipolar disorders, cognitive dysfunctions, in particular cognitive dysfunctions associated with schizophrenia, cognitive dysfunctions associated with dementia (Alzheimer's disease), Parkinson's disease, anxiety, dyskinesia, in particular L-DOPA induced dyskinesia (LID), especially dyskinesia associated with L-DOPA therapy to treat Parkinson's disease, substance-related disorders, especially substance use disorder, substance tolerance conditions associated with substance withdrawal, attention deficit disorders with or without hyperactivity, eating disorders, and personality disorder as well as pain. Disorders or conditions which can be treated by modulating the dopamine D3 receptor, including curative treatment, control or amelioration and prophylaxis, also include treatment of disturbances of kidney function, i.e. renal function disorders, in particular kidney function disturbances which are caused by diabetes such as diabetes mellitus, also termed as diabetic nephropathy.

Thus, the invention relates to the use of compounds of formula I, their N-oxides and their prodrugs and the pharmaceutically acceptable salts thereof, for treatment of disorders or conditions, which can be treated by modulation of the dopamine D3 receptor, i.e. the invention relates to the use of such compounds for curative treatment of such a disease or disorder, controlling such a disease or disorder, ameliorating the symptoms associated with such a disease or disorder and reducing the risk for such a disease or disorder.

The present invention also relates to a method for the treatment of a medical disorder, selected from neurological and psychiatric disorders which can be treated by modulation of the dopamine D3 receptor, said method comprising administering an effective amount of at least one compound, selected from the group of compounds of formula I, their N-oxides, their prodrugs and the pharmaceutically acceptable salts thereof, to a mammal in need thereof. The present invention also relates to a method for the treatment of renal function disorders, in particular kidney function disturbances which are caused by diabetes such as diabetes mellitus, said method comprising administering an effective amount of at least one compound, selected from the group of compounds of formula I, their N-oxides, their prodrugs and the pharmaceutically acceptable salts thereof, to a mammal in need thereof.

The present invention in particular relates to:
a method for treating, controlling, ameliorating or reducing the risk of schizophrenia in a mammalian;
a method for treating, controlling, ameliorating or reducing the risk of cognitive disturbances associated with schizophrenia in a mammalian;
a method for treating, controlling, ameliorating or reducing the risk of depression in a mammalian;
a method for treating, controlling, ameliorating or reducing the risk of bipolar disorders in a mammalian;
a method for treating or ameliorating the symptoms associated with substance abuse disorders in a mammalian;
a method for treating or ameliorating the symptoms associated with eating disorders in a mammalian;
a method for treating, controlling, ameliorating or reducing the risk of cognitive disturbances associated with Alzheimer's disease in a mammalian;
a method for treating, controlling, ameliorating or reducing the risk of anxiety in a mammalian;
a method for treating, controlling, ameliorating or reducing the risk of Parkinson's disease in a mammalian;
a method for treating, controlling, ameliorating or reducing the risk of disturbances associated with Parkinson's disease in a mammalian;
a method for treating, controlling, ameliorating or reducing the risk of renal function disorders, in particular diabetic nephropathy in a mammalian;
a method for treating, controlling, ameliorating or reducing the risk of disturbances associated with renal function disorders, in particular diabetic nephropathy, in a mammalian;
a method for treating, controlling, ameliorating or reducing the risk of dyskinesia, in particular L-DOPA induced dyskinesia (LID), especially LID associated with treatment of Parkinson's disease, more especially LID associated with long-term treatment of Parkinson's disease;
and a method for treating, ameliorating or reducing the risk of pain in a mammalian;

which methods comprising administering an effective amount of at least one compound, selected from the group of compounds of formula I, their N-oxides, their prodrugs and the pharmaceutically acceptable salts thereof, to a mammal in need thereof. The subject treated in the present methods is generally a mammal, preferably a human being, male or female, in whom modulation of dopamine D3 receptor is desired. The terms "effective amount" and "therapeutically effective amount" mean the amount of the subject compound that will elicit the biological or medical response of a tissue, system, animal or human that is being sought by the researcher, veterinarian, medical doc-tor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes, wherein there may be a slowing, interrupting, arresting, controlling, or stopping of the progression of the disorders described herein, but does not necessarily indicate a total elimination of all disorder symptoms, as well as the prophylactic therapy of the mentioned conditions, particularly in a patient who is pre-disposed to such disease or disorder. The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of and or "administering a" compound should be understood to mean providing a compound of the invention or a prodrug of a compound of the invention to the individual in need of treatment.

A preferred embodiment of the present invention provides a method for treating schizophrenia, comprising: administering to a patient in need thereof an effective amount of at least one compound, selected from the group of compounds of formula I, their N-oxides, their prodrugs and the pharmaceutically acceptable salts thereof.

In another preferred embodiment, the present invention provides a method for treating cognitive disturbances associated with schizophrenia, comprising: administering to a patient in need thereof an effective amount of at least one compound, selected from the group of compounds of formula I, their N-oxides, their prodrugs and the pharmaceutically acceptable salts thereof.

In another preferred embodiment, the present invention provides a method for treating dyskinesia comprising: administering to a patient in need thereof an effective amount of at least one compound, selected from the group of compounds of formula I, their N-oxides, their prodrugs and the pharmaceutically acceptable salts thereof.

In another preferred embodiment, the present invention provides a method for treating L-DOPA induced dyskinesia (LID), in particular LID associated with treatment of Parkinson's disease, especially LID associated with long-term treatment of Parkinson's disease comprising: administering to a patient in need thereof an effective amount of at least one compound, selected from the group of compounds of formula I, their N-oxides, their prodrugs and the pharmaceutically acceptable salts thereof.

At present, the fourth edition of the Diagnostic and Statistical Manual of Mental Disorders (DSM-IV) (1994, American Psychiatric Association, Washington, D.C.), provides a diagnostic tool including schizophrenia and other psychotic disorders. These include: disorders having psychotic symptoms as the defining feature. The term psychotic refers to delusions, prominent hallucinations, disorganized speech, disorganized or catatonic behavior. The disorder includes: paranoid, disorganized, catatonic, undif-ferentiated, and residual schizophrenia, schizophreniform disorder, schizoaffective disorder, delusional disorder, brief psychotic disorder, shared psychotic disorder, psychotic disorder due to a general medical condition, substance-induced psychotic disorder, and psychotic disorder not otherwise specified. The skilled artisan will recognize that there are alternative nomenclatures, nosologies, and classification systems for neurological and psychiatric disorders, and particular schizophrenia, and that these systems evolve with medical scientific progress. Thus, the term "schizophrenia" is intended to include like disorders that are described in other diagnostic sources.

In another preferred embodiment, the present invention provides a method for treating substance-related disorders, comprising: administering to a patient in need thereof an effective amount of at least one compound, selected from the group of compounds of formula I, their N-oxides, their prodrugs and the pharmaceutically acceptable salts thereof.

In another preferred embodiment, the present invention provides a method for treating anxiety, comprising: administering to a patient in need thereof an effective amount of at least one compound, selected from the group of compounds of formula I, their N-oxides, their prodrugs and the pharmaceutically acceptable salts thereof. At present, the fourth edition of the Diagnostic and Statistical Manual of Mental Disorders (DSM-IV) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified. As used herein the term "anxiety" includes treatment of those anxiety disorders and related disorder as described in the DSM-IV. The skilled artisan will recognize that there are alternative nomenclatures, nosologies, and classification systems for neurological and psychiatric disorders, and particular anxiety, and that these systems evolve with medical scientific progress. Thus, the term "anxiety" is intended to include like disorders that are described in other diagnostic sources.

In another preferred embodiment, the present invention provides a method for treating depression, comprising: administering to a patient in need thereof an effective amount of at least one compound, selected from the group of compounds of formula I, their N-oxides, their prodrugs and the pharmaceutically acceptable salts thereof. At present, the fourth edition of the Diagnostic and Statistical Manual of Mental Disorders (DSM-IV) (1994, American Psychiatric Association, Washington, D.C.), provides a diagnostic tool including depression and related disorders. Depressive disorders include, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder. As used herein the term "depression" includes treatment of those depression disorders and related disorder as described in the DSM-1V.

In another preferred embodiment, the present invention provides a method for treating substance-related disorders, especially substance dependence, substance abuse, substance tolerance, and substance withdrawal, comprising: administering to a patient in need thereof an effective amount at least one compound, selected from the group of compounds of formula I, their N-oxides, their prodrugs and the pharmaceutically acceptable salts thereof. At present, the fourth edition of the Diagnostic and Statistical Manual of Mental Disorders (DSM-IV) (1994, American Psychiatric Association, Washington, D.C.), provides a diagnostic tool including disorders related to taking a drug of abuse (including alcohol), to the side effects of a medication, and to toxin exposure. Substances include alcohol, amphetamine and similarly acting sympathomimetics, caffeine, cannabis, cocaine, hallucinogens, inhalants, nicotine, opioids, phencyclidine (PCP) or similarly acting arylcyclohexylamines, and sedatives, hypnotics, or anxiolytics. Also, polysubstance dependence and other unknown substance-related disorders are included. The skilled artisan will recognize that there are alternative nomenclatures, nosologies, and classification systems for neurological and psychiatric disorders, and particular substance-related disorders, and that these systems evolve with medical scientific progress. Thus, the term "substance-related disorder" is intended to include like disorders that are described in other diagnostic sources.

In another preferred embodiment, the present invention provides a method for treating Parkinson's disease and the symptoms and disturbances associated with Parkinson's disease: comprising: administering to a patient in need thereof an effective amount at least one compound, selected from the group of compounds of formula I, their N-oxides, their prodrugs and the pharmaceutically acceptable salts thereof.

In another preferred embodiment, the present invention provides a method for treating renal function disorders, in particular diabetic nephropathy: comprising administering to a patient in need thereof an effective amount at least one compound, selected from the group of compounds of formula I, their N-oxides, their prodrugs and the pharmaceutically acceptable salts thereof.

In the treatment, prevention, control, amelioration, or reduction of risk of conditions which require modulation of the dopamine D3 receptor an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day. When treating, preventing, controlling, ameliorating, or reducing the risk of neurological and psychiatric disorders or other diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligram to about 500 milligrams, in the case of a 70 kg adult human, the total daily dose will generally be from about 3 milligrams to about 350 milligrams. This dosage regimen may be adjusted to provide the optimal therapeutic response. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the present invention may be administered by conventional routes of administration, including parenteral (e.g., intramuscular, intrapentoneal, intravenous, ICV, intracisternal injection or infusion, subcutaneous injection, or implant), oral, by inhalation spray, nasal, vaginal, rectal, sublingual, or topical routes of administration.

The compounds according to the present invention are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefore, contemporaneously or sequentially with a compound of Formula I. When a compound of formula I is used contemporaneously with one or more other drugs, a pharmaceutical composition in unit dosage form containing such other drugs and the compound of formula I is preferred. However, the combination therapy may also include therapies in which the compound of formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of formula I, an N-oxide, a prodrug or a salt thereof. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The present invention also relates to pharmaceutical compositions (i.e. medica-ments) which comprise at least one compound of the present invention and, where appropriate, one or more suitable excipients.

These excipients/drug carriers are chosen according to the pharmaceutical form and the desired mode of administration.

The compounds of the present invention can be used to manufacture pharmaceutical compositions for parenteral (e.g., intramuscular, intrapentoneal, intravenous, ICV, intracisternal injection or infusion, subcutaneous injection, or implant), oral, sublingual, intratracheal, intranasal, topical, transdermal, vaginal or rectal administration, and be administered to animals or humans in unit dose forms, mixed with conventional pharmaceutical carriers, for the prophylaxis or treatment of the above impairments or diseases.

In the pharmaceutical compositions, the at least one compound of the present invention may be formulated alone or together with further active compounds, in suitable dosage unit formulations containing conventional excipients, which generally are non-toxic and/or pharmaceutically acceptable. Carriers or excipients can be solid, semisolid or liquid materials which serve as vehicles, carriers or medium for the active compound. Suitable excipients are listed in the specialist medicinal monographs. In addition, the formulations can comprise pharmaceutically acceptable carriers or customary auxiliary substances, such as glidants; wetting agents; emulsifying and suspending agents; pre-servatives; antioxidants; antiirritants; chelating agents; coating auxiliaries; emulsion stabilizers; film formers; gel formers; odor masking agents; taste corrigents; resin; hy-drocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharma-cy, cosmetics and related fields], 4$^{th}$ edition, Aulendorf: ECV-Editio-Kantor-Verlag, 1996.

Suitable unit dose forms include forms for oral administration, such as tablets, gelatin capsules, powders, granules and solutions or suspensions for oral intake, forms for sublingual, buccal, intratracheal or intranasal administration, aerosols, implants, forms of subcutaneous, intramuscular or intravenous administration and forms of rectal administration.

The compounds of the invention can be used in creams, ointments or lotions for topical administration.

If a solid composition is prepared in the form of tablets, the main ingredient is mixed with a pharmaceutical carrier such as gelatin, starch, lactose, magnesium stearate, talc, silicon dioxide or the like.

The tablets may be coated with sucrose, a cellulose derivative or another suitable substance or be treated otherwise in order to display a prolonged or delayed activity and in order to release a predetermined amount of the active basic ingredient continuously.

A preparation in the form of gelatin capsules is obtained by mixing the active ingredient with an extender and taking up the resulting mixture in soft or hard gelatin capsules.

A preparation in the form of a syrup or elixir or for administration in the form of drops may comprise active ingredients together with a sweetener, which is preferably calorie-free, methylparaben or propylparaben as antiseptics, a flavoring and a suitable coloring.

The water-dispersible powders or granules may comprise the active ingredients mixed with dispersants, wetting agents or suspending agents such as polyvinylpyrrolidones, and sweeteners or taste improvers.

Rectal administration is achieved by the use of suppositories which are prepared with binders which melt at the rectal temperature, for example cocobutter or polyethylene glycols. Parenteral administration is effected by using aqueous suspensions, isotonic salt solutions or sterile and injectable solutions which comprise pharmacologically suitable dispersants and/or wetting agents, for example propylene glycol or polyethylene glycol.

The active basic ingredient may also be formulated as microcapsules or liposomes/centrosomes, if suitable with one or more carriers or additives.

In addition to the compounds of the general formula I, their prodrugs, their N-oxides, their tautomers, their hydrates or their pharmaceutically suitable salts, the compositions of the invention may comprise further active basic ingredients which may be beneficial for the treatment of the impairments or diseases indicated above.

The present invention thus further relates to pharmaceutical compositions in which a plurality of active basic ingredients are present together, where at least one thereof is a compound of the invention.

When producing the pharmaceutical compositions, the compounds according to the invention are optionally mixed or diluted with one or more carriers.

The following examples are intended for further illustration of the present invention.

The compounds were either characterized via $^1$H NMR in d$_6$-dimethylsulfoxid, deuteromethanol or deuterochloroform, if not stated otherwise, on a 400 MHz, 500 MHz, or 600 MHz NMR instrument (Bruker AVANCE), or by mass spectrometry, generally recorded via HPLC-MS in a fast gradient on C18-material (electrospray-ionisation (ESI) mode), or melting point.

The magnetic nuclear resonance spectral properties (NMR) refer to the chemical shifts (δ) expressed in parts per million (ppm). The relative area of the shifts in the 1H NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m).

Abbreviations:
AcOH acetic acid
Boc tert-butyloxycarbonyl
DCE 1,2-dichloroethane
DCM dichloromethane
EA ethyl acetate
EtOH ethanol
hr hour
MeOH methanol
NaOMe sodium methoxide
MeOD deuteromethanol
PE petrolether
pre-TLC preparative thin layer chromatography
RT retention time
THF tetrahydrofuran Intermediates I. Pyrimidyl-Piperazine Building Block I.1 2-tert-Butyl-4-(2-methoxy-ethyl)-6-piperazin-1-yl-pyrimidine I.1.1 5-Methoxy-3-oxo-pentanoic acid methyl ester To a solution of 3-methoxy propionyl chloride (51.7 g, 359 mmol) and pyridine (87 mL, 1077 mmol) in DCM (400 mL), dimedon (44 g, 359 mmol) was added dropwise at 0° C. to 10° C. The reaction mixture was stirred overnight at room temperature, 1 N HCl (400 mL) was added, extracted with DCM (500 mL×3). The organic layer was washed with water, dried over $Na_2SO_4$, filtered, and concentrated to dryness. The oily residue was dissolved in MeOH (400 mL) and refluxed for 2 hrs. The reaction mixture was concentrated to dryness. The residue was purified by silica gel column (PE:EA=15:1) to give the title compound (27 g, 47.0% yield) as white oil.

$^1$H NMR (400 MHz $CDCl_3$): δ 3.72 (s, 3H), 3.65-3.62 (m, 2H), 3.49 (s, 2H), 3.31 (s, 3H), 2.78-2.75 (m, 2H).

I.1.2 2-tert-Butyl-6-(2-methoxy-ethyl)-pyrimidin-4-ol

5-Methoxy-3-oxo-pentanoic acid methyl ester (27 g, 169 mmol) and tert-butyl amidinium hydrochloride (18.57 g, 185 mmol) were dissolved in MeOH (200 mL); sodium methanolate (27.3 g, 506 mmol) was added in portions to the solution at 10° C. The reaction mixture was then stirred at room temperature overnight. The reaction mixture was concentrated to half the volume, filtered, the filtrate was acidified with 1 N HCl to pH=5, the precipitate was collected by filtration, which was dried under high vacuum to give the title compound (20 g, 56% yield) as white oil.

$^1$H NMR (400 MHz $CDCl_3$): δ 11.91 (s, 1H), 6.19 (s, 1H), 3.73-3.71 (m, 2H), 3.34 (s, 3H), 2.79-2.75 (m, 2H), 1.37 (s, 9H).

I.1.3 2-tert-Butyl-4-chloro-6-(2-methoxy-ethyl)-pyrimidine

To a solution of 2-tert-butyl-6-(2-methoxy-ethyl)-pyrimidin-4-ol (20 g, 95 mmol) in toluene (200 mL) and DMF (2 mL) was added dropwise $POCl_3$ (36.5 g, 238 mmol) in an ice bath. The mixture was stirred for 3 hrs at room temperature. The reaction mixture was poured into water, extracted with DCM (400 mL×3). The organic layer was dried over $Na_2SO_4$ and concentrated to give the title compound (20 g, 92% yield) as a yellow oil.

$^1$H NMR (400 MHz $CDCl_3$): δ 7.02 (s, 1H), 3.78-3.75 (m, 2H), 3.33 (s, 3H), 2.96-2.93 (m, 2H), 1.36 (s, 9H).

I.1.4 2-tert-Butyl-4-(2-methoxy-ethyl)-6-piperazin-1-yl-pyrimidine

A solution of piperazine (45.2 g, 525 mmol) in ethanol (300 mL) was heated to reflux. A solution of 2-tert-butyl-4-chloro-6-(2-methoxy-ethyl)-pyrimidine (20 g, 87 mmol) in ethanol (50 mL) was added dropwise to the above solution. The solution was refluxed for another 3 hrs, cooled to room temperature. Then water was added and the organic layer was extracted with EA (400 mL×3). To the organic layer was added 5% citric acid (1 L), separated, and the aqueous layer was collected and adjusted to alkaline pH>8 with 2 N NaOH. The alkaline aqueous layer was extracted with EA (400 mL×3), and the organic phase was dried over $Na_2SO_4$, filtered and concentrated to give the title compound (20 g, 82% yield) as a yellow oil.

$^1$H NMR ($CDCl_3$ 400 MHz): δ 6.17 (s, 1H), 3.76-3.73 (m, 2H), 3.60-3.57 (m, 4H), 3.33 (s, 3H), 2.93-2.90 (m, 4H), 2.83-2.80 (m, 2H), 1.72-1.70 (m, 1H), 1.31 (s, 9H).

LC-MS (ESI): m/z 279 (M+H)$^+$.

I.2 2-tert-butyl-4-cyclobutyl-6-(piperazin-1-yl)pyrimidine

I.2.1 2-tert-butyl-6-cyclobutyl-pyrimdin-4-ol

A mixture of methyl 3-cyclobutyl-3-oxo-propanoate (4.3 g, 27.53 mmol) and 2,2-dimethylpropanamidine (2.3 g, 22.10 mmol) was stirred in dry MeOH (50 mL) and NaOMe (5.0 g, 92 mmol) was added in portions at 10° C. The suspension was stirred at room temperature overnight. The reaction mixture was concentrated to roughly half of the volume and filtered. The filtrate was extracted with water and DCM. The combined organic layers were washed with brine, dried over $Na_2SO_4$, filtered, and concentrated under reduced pressure. The residue was stirred with acetone and the precipitate collected, dried under vacuum to give the title compound (3.15 g, 15.27 mmol, 66%).

LC-MS (ESI): m/z 207 (M+H)$^+$, TR: 0.864 min.

I.2.2 2-tert-butyl-4-chloro-6-cyclobutyl-pyrimidine 2-tert-butyl-6-cyclobutyl-pyrimdin-4-ol (3.15 g, 15.27 mmol) was dissolved in toluene (25 ml)/DMF (0.3 ml). $POCl_3$ (3.5 mL, 38 mmol) was added dropwise at 10° C. The resulted solution was stirred at room temperature for 3 h then poured into water, extracted with DCM. The organic layer was dried over $Na_2SO_4$, filtered, and concentrated under reduced pressure to give the title compound (3.28 g, 97%). The crude material was used without further purification for the next step.

LC-MS: m/z=225.0 (M+H)$^+$, RT: 1.186 min

I.2.3 2-tert-butyl-4-cyclobutyl-6-(piperazin-1-yl)pyrimidine piperazine (7.54 g, 87.57 mmol) was dissolved in EtOH, 2-tert-butyl-4-chloro-6-cyclobutyl-pyrimidine (3.28 g, 14.60 mmol) was added dropwise at 80° C. over 10 min. The solution was refluxed overnight and then concentrated under reduced pressure. The residue was dissolved in EtOAc, washed with water and brine, dried over Na₂SO₄, filtered, and concentrated under reduced pressure to give the title compound (3.5 g, 87%).

LC-MS: m/z=275.0 (M+H), RT: 0.564 min

II. Aldehyde Building Block

II.1 tert-butyl N-[3-(2-oxoethyl)cyclobutyl]carbamate

II.1.1 (3-tert-Butoxycarbonylamino-cyclobutyl-idene)-acetic acid methyl ester To a solution of (3-oxo-cyclobutyl)-carbamic acid tert-butyl ester (5.6 g, 30 2 mmol) in anhydrous toluene (100 mL) was added methyl (triphenylphosphoranylidene)acetate (10.7 g, 45.4 mmol) and heated to reflux overnight under N₂. After cooling to room temperature, the mixture was poured into water and extracted with EA. The organic phase was dried over Na₂SO₄, concentrated under reduced pressure to give a residue, which was purified by column chromatography on silica gel (eluted with PE:EA=20:1) to give the title compound (7 g, yield 96%) as a white solid.

¹H NMR (400 MHz, CDCl₃): δ 5.71 (s, 1H), 4.86 (br, 1H), 4.25 (br, 1H), 3.70 (s, 3H), 3.60 (br, 1H), 3.23-3.18 (br, 1H), 2.97-2.92 (br, 1H), 2.79-2.73 (br, 1H), 1.46 (s, 9H).

II.1.2 (3-tert-Butoxycarbonylamino-cyclobutyl)-acetic acid methyl ester

To a solution of (3-tert-Butoxycarbonylamino-cyclobutyl-idene)-acetic acid methyl ester (7 g, 29 mmol) in methanol (100 mL) was added Pd/C (5 g) and stirred at room temperature under H₂ balloon overnight. After TLC showed the reaction was completed, the mixture was filtered over Celite. The filtrate was concentrated under reduced pressure to give the title compound (7 g, yield 99%) as a white solid, which was used for the next step directly without further purification.

II.1.3 3-(2-Hydroxy-ethyl)-cyclobutyl]-carbamic acid tert-butyl ester

To a solution of (3-tert-butoxycarbonylamino-cyclobutyl)-acetic acid methyl ester (7 g, 28.8 mmol) in anhydrous THF (100 mL) was added LiAlH₄ (2.18 g, 57.5 mmol) dropwise at 0° C. and the mixture was stirred at 0° C. for 2 hrs. The mixture was quenched with water (2 mL), NaOH solution (0.5 N, 2 mL) and water (2 mL), filtered and extracted with EA. The organic phase was washed by brine, dried over Na₂SO₄, filtered and concentrated under reduced pressure to give the title compound (5.7 g, yield 92%) as a white solid, which was used for next step directly without further purification.

II.1.4 tert-butyl N-[3-(2-oxoethyl)cyclobutyl]carbamate

To a solution of 3-(2-hydroxy-ethyl)-cyclobutyl]-carbamic acid tert-butyl ester (5.2 g, 24.1 mmol) in anhydrous DCM (100 mL) was added Dess-Martin periodinane (20.5 g, 48.3 mmol) and stirred at room temperature for 5 hrs. The mixture was quenched with Na₂S₂O₃ solution, extracted with DCM. The organic phase was concentrated under reduced pressure to give a residue, which was purified by column chromatography on silica gel (eluted with PE:EA=5:1) to give the title compound (2.7 g, yield 52%) as an oily liquid.

II.2 tert-butyl trans-4-(2-oxoethyl)cyclohexylcarbamate

Commercially available

II.3 tert-butyl cis-4-(2-oxoethyl)cyclohexylcarbamate

Commercially available

III. EXAMPLES

Example 1 trans-N-[trans-4-[2-[4-(2-tert-butyl-6-cyclobutyl-pyrimidin-4-yl)piperazin-1-yl]ethyl]cyclohexyl]-4-hydroxy-cyclohexanecarboxamide (compound 1; compound of the formula I, where R¹ is trans-4-hydroxycyclohexyl; m is 2, n is 2, R²=H and the radical R¹—C(=O)—NH and the radical R² have cis configuration)

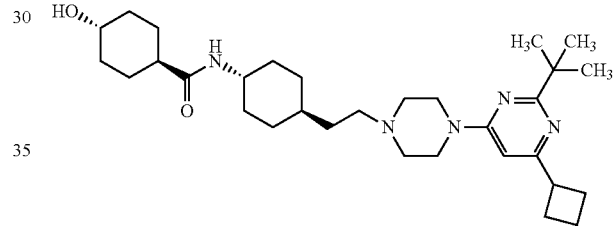

1.1 tert-butyl trans-N-[4-[2-[4-(2-tert-butyl-6-cyclobutyl-pyrimidin-4-yl)piperazin-1-yl]ethyl]cyclohexyl]carbamate

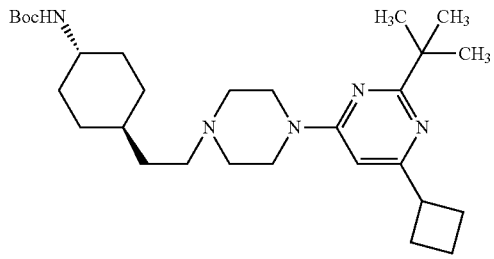 [SMILES: CC(C)(C)OC(=O)N[C@H]1CC[C@H](CCN2CCN(c3cc(C4CCC4)nc(C(C)(C)C)n3)CC2)CC1]

A mixture of 2-tert-butyl-4-cyclobutyl-6-(piperazin-1-yl) pyrimidine (7.16 g, 26.1 mmol) and tert-butyl trans-4-(2-oxoethyl)cyclohexylcarbamate (6 g, 24.86 mmol) in DCE (100 ml) was stirred at room temperature for 10 min. AcOH and sodium triacetox-yhydroborate (7.90 g, 37.3 mmol) were added. After 4 h, water was added. The aqueous layer was extracted with methylene chloride (3×50 mL). The combined organic layers were washed with brine, dried over Na₂SO₄, filtered, and concentrated under reduced pressure to give the title compound as a yellow oil of (11.2 g, 21.29 mmol, 86% yield) which was used next step without purification.
LC-MS: M/z=500.0 (M+H)⁺, RT: 0.67 min.

1.2 Trans-4-(2-(4-(2-(tert-butyl)-6-cyclobutylpyrimidin-4-yl)piperazin-1-yl)ethyl)cyclohexanamine

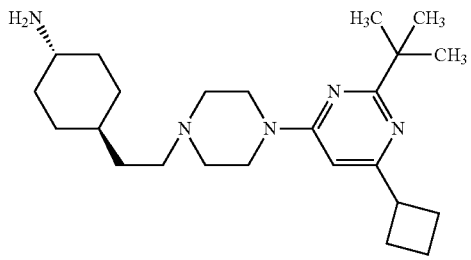 [SMILES: CC(C)(C)c1nc(C2CCC2)cc(N2CCN(CC[C@H]3CC[C@H](N)CC3)CC2)n1]

Tert-butyl N-[trans-[4-[2-[4-(2-tert-butyl-6-cyclobutyl-pyrimidin-4-yl)piperazin-1-yl]ethyl]cyclohexyl]carbamate (11.20 g, 22.41 mmol) was dissolved in HCl/ethyl acetate (150 mL). The resulting solution was stirred at about 25° C. for 16 h. Solvent was removed under reduced pressure to provide the title compound (8.9 g, 21.16 mmol, 94% yield) as a colorless solid.
LC-MS: M/z=400.0 (M+H)⁺, RT: 0.52 min 1.3 trans-N-[trans-4-[2-[4-(2-tert-butyl-6-cyclobutyl-pyrimidin-4-yl)piperazin-1-yl]ethyl]cyclohexyl]-4-hydroxy-cyclohexanecarboxamide Trans-4-hydroxycyclohexanecarboxylic acid (1,991 g, 13.81 mmol) was added to a solution of trans-4-(2-(4-(2-(tert-butyl)-6-cyclobutylpyrimidin-4-yl)piperazin-1-yl)ethyl)cyclohexanamine (4.6 g, 11.51 mmol) in dichloromethane. HATU (2-(3H-[1,2,3]triazolo[4,5-b]pyridin-3-yl)-1,1,3,3-tetramethylisouronium hexafluorophosphate, 5.25 g, 13.8 mmol) and diisopropylethylamine (6.03 mL, 34.5 mmol) were added and the mixture stirred at room temperature for 14 h. The solvent was evaporated and the residue partitioned between dichloromethane and water. The aqueous phase was extracted several times with dichloromethane. The combined organic layers were washed twice with 5% aqueous sodium bicarbonate solution and twice with saturated aqueous sodium chloride solution, dried over sodium sulfate, filtered and evaporated to dryness. Purification via silica gel chromatography (330 g Reveleris NP cartridge) with di-chloromethane/methanol (0-80%) as eluent yielded 6.05 g of the title compound.
LC-MS: m/z 526.4 (M+H)⁺, RT: 2.54 min.
¹H-NMR (CDCl₃, 400 MHz): 1.04-1.08 (m, 4H), 1.13-1.25 (m, 3H), 1.34 (s, 9H), 1.43-1.63 (m, 5H), 1.74-1.79 (m, 2H), 1.87-2.06 (m, 9H), 2.25-2.37 (m, 4H), 2.42 (m, 2H), 2.53 (bs, 4H), 3.43-3.46 (m, 1H), 3.59-3.67 (m, 2H), 3.67 (bs, 4H), 5.23 (d, J=8.4 Hz, 1H), 6.12 (s, 1H).
The compounds of the examples 2 to 44 were prepared following the same way shown above Example 2 trans-N-[trans-4-[2-[4-[2-tert-butyl-6-(2-methoxyethyl) pyrimidin-4-yl]piperazin-1-yl]ethyl]cyclohexyl]-4-hydroxy-cyclohexanecarboxamide (compound 2; compound of the formula I, where R¹ is trans-4-hydroxycyclohexyl; m is 2, n is 2, R²=H, and the radical R¹—C(=O)—NH and the radical R² have cis-configuration)

Example 3 trans-N-[cis-4-[2-[4-[2-tert-butyl-6-(2-methoxyethyl)pyrimidin-4-yl]piperazin-1-yl]ethyl]cyclohexyl]-4-hydroxy-cyclohexanecarboxamide (compound 3; compound of the formula I, where R¹ is trans-4-hydroxycyclohexyl; m is 2, n is 2, R²=H and the radical R¹—C(=O)—NH and the radical R² have trans-configuration)

Example 4 cis-N-[trans-4-[2-[4-[2-tert-butyl-6-(2-methoxyethyl)pyrimidin-4-yl]piperazin-1-yl]ethyl]cyclohexyl]-4-hydroxy-cyclohexanecarboxamide (compound 4; compound of the formula I, where R¹ is cis-4-hydroxycyclohexyl; m is 2, n is 2, R²=H and the radical R¹—C(=O)—NH and the radical R² have cis-configuration)

Example 5

Cis-N-[cis-4-[2-[4-[2-tert-butyl-6-(2-methoxyethyl)pyrimidin-4-yl]piperazin-1-yl]ethyl]cyclohexyl]-4-hydroxy-cyclohexanecarboxamide (compound 5; compound of the formula I, where R¹ is cis-4-hydroxycyclohexyl; m is 2, n is 2, R²=H, and the radical R¹—C(=O)—NH and the radical R² have trans-configuration)

Example 6 trans-N-[cis-4-[2-[4-(2-tert-butyl-6-cyclobutyl-pyrimidin-4-yl)piperazin-1-yl]ethyl]cyclohexyl]-4-hydroxy-cyclohexanecarboxamide (compound 6, compound of the formula I, where R¹ is trans-4-hydroxycyclohexyl; m is 2, n is 2, R²=H and the radical R¹—C(=O)—NH and the radical R² have trans-configuration)

Example 7

Trans-N-[trans-3-[2-[4-[2-tert-butyl-6-(2-methoxyethyl) pyrimidin-4-yl]piperazin-1-yl]ethyl]cyclobutyl]-4-hydroxy-cyclohexanecarboxamide; 2,2,2-trifluoroacetic acid (compound 7, compound of the formula I, where R¹ is trans-4-hydroxycyclohexyl; m is 1, n is 1, R²=H and the radical R¹—C(=O)—NH and the radical R² have cis-configuration)

Example 8 trans-N-[cis-3-[2-[4-[2-tert-butyl-6-(2-methoxyethyl)pyrimidin-4-yl]piperazin-1-yl]ethyl]cyclobutyl]-4-hydroxy-cyclohexanecarboxamide; 2,2,2-trifluoroacetic acid (compound 8, compound of the formula I, where R¹ is trans-4-hydroxycyclohexyl; m is 1, n is 1, R²=H and the radical R¹—C(=O)—NH and the radical R² have trans-configuration)

Example 9

Trans-N-[trans-3-[2-[4-(2-tert-butyl-6-cyclobutyl-pyrimidin-4-yl)piperazin-1-yl]ethyl]cyclobutyl]-4-hydroxy-cyclohexanecarboxamide; compound 9; compound of the formula I, where R¹ is trans-4-hydroxycyclohexyl; m is 1, n is 1 and the radical R¹—C(=O)—NH, R²=H and the radical R² have cis-configuration)

Example 10

Trans-N-[cis-3-[2-[4-(2-tert-butyl-6-cyclobutyl-pyrimidin-4-yl)piperazin-1-yl]ethyl]cyclobutyl]-4-hydroxy-cyclohexanecarboxamide (compound 10; compound of the formula I, where $R^1$ is trans-4-hydroxycyclohexyl; m is 1, n is 1, $R^2$=H and the radical $R^1$—C(=O)—NH and the radical $R^2$ have trans-configuration)

Example 11

N-[trans-3-[2-[4-[2-tert-butyl-6-(2-methoxyethyl)pyrimidin-4-yl]piperazin-1-yl]ethyl]cyclobutyl]-4-hydroxy-cyclohexanecarboxamide (compound 11; compound of the formula I, where $R^1$ is 4-hydroxycyclohexyl; m is 1, n is 1, $R^2$=H and the radical $R^1$—C(=O)—NH and the radical $R^2$ have cis-configuration)

Example 12

Cis-N-[cis-3-[2-[4-[2-tert-butyl-6-(2-methoxyethyl)pyrimidin-4-yl]piperazin-1-yl]ethyl]cyclobutyl]-4-hydroxy-cyclohexanecarboxamide (compound 12; compound of the formula I, where $R^1$ is cis-4-hydroxycyclohexyl; m is 1, n is 1, $R^2$=H and the radical $R^1$—C(=O)—NH and the radical $R^2$ have trans-configuration)

Example 13

Cis-N-[trans-4-[2-[4-(2-tert-butyl-6-cyclobutyl-pyrimidin-4-yl)piperazin-1-yl]ethyl]cyclohexyl]-3-hydroxy-cyclobutanecarboxamide (compound 13; compound of the formula I, where $R^1$ is cis-3-hydroxycyclobutyl; m is 2, n is 2, $R^2$=H and the radical $R^1$—C(=O)—NH and the radical $R^2$ have cis-configuration)

Example 14

Cis-N-[trans-4-[2-[4-(2-tert-butyl-6-cyclobutyl-pyrimidin-4-yl)piperazin-1-yl]ethyl]cyclohexyl]-4-hydroxy-cyclohexanecarboxamide; 2,2,2-trifluoroacetic acid (compound 14; compound of the formula I, where $R^1$ is cis-4-hydroxycyclohexyl; m is 2, n is 2, $R^2$=H and the radical $R^1$—C(=O)—NH and the radical $R^2$ have cis-configuration)

Example 15

Cis-N-[cis-4-[2-[4-(2-tert-butyl-6-cyclobutyl-pyrimidin-4-yl)piperazin-1-yl]ethyl]cyclohexyl]-4-hydroxy-cyclohexanecarboxamide; 2,2,2-trifluoroacetic acid (compound 15; compound of the formula I, where $R^1$ is cis-4-hydroxycyclohexyl; m is 2, n is 2, $R^2$=H and the radical $R^1$—C(=O)—NH and the radical $R^2$ have trans-configuration)

Example 16

Cis-N-[trans-3-[2-[4-(2-tert-butyl-6-cyclobutyl-pyrimidin-4-yl)piperazin-1-yl]ethyl]cyclobutyl]-4-hydroxy-cyclohexanecarboxamide; 2,2,2-trifluoroacetic acid (compound 16; compound of the formula I, where $R^1$ is cis-4-hydroxycyclohexyl; m is 1, n is 1, $R^2$=H and the radical $R^1$—C(=O)—NH and the radical $R^2$ have cis-configuration)

Example 17 cis-N-[cis-4-[2-[4-[2-tert-butyl-6-(2-methoxyethyl)pyrimidin-4-yl]piperazin-1-yl]ethyl]cyclohexyl]-3-hydroxy-cyclobutanecarboxamide (compound 17; compound of the formula I, where $R^1$ is cis-4-hydroxycyclohexyl; m is 1, n is 1, $R^2$=H and the radical $R^1$—C(=O)—NH and the radical $R^2$ have trans-configuration)

Example 18 cis-N-[trans-4-[2-[4-[2-tert-butyl-6-(2-methoxyethyl)pyrimidin-4-yl]piperazin-1-yl]ethyl]cyclohexyl]-3-hydroxy-cyclobutanecarboxamide (compound 18; compound of the formula I, where $R^1$ is cis-3-hydroxycyclobutyl; m is 2, n is 2, $R^2$=H and the radical $R^1$—C(=O)—NH and the radical $R^2$ have cis-configuration)

Example 19

N-[trans-4-[2-[4-(2-tert-butyl-6-cyclobutyl-pyrimidin-4-yl)piperazin-1-yl]ethyl]cyclohexyl]-3-hydroxy-3-(trifluoromethyl)cyclobutanecarboxamide (Compound 19; compound of the formula I, where $R^1$ is 3-hydroxy-3-trifluoromethylcyclobutyl; m is 2, n is 2, $R^2$=H and the radical $R^1$—C(=O)—NH and the radical $R^2$ have cis-configuration)

Example 20 trans-N-[trans-4-[2-[4-(2,6-ditert-butylpyrimidin-4-yl)piperazin-1-yl]ethyl]cyclohexyl]-4-hydroxy-cyclohexanecarboxamide (compound 20; compound of the formula I, where $R^1$ is trans-4-hydroxycyclohexyl; m is 2, n is 2, $R^2$=H and the radical $R^1$—C(=O)—NH and the radical $R^2$ have cis-configuration)

Example 21 trans-N-[trans-4-[2-[4-[2-tert-butyl-6-(trifluoromethyl)pyrimidin-4-yl]piperazin-1-yl]ethyl]cyclohexyl]-4-hydroxy-cyclohexanecarboxamide (compound 21; compound of the formula I, where $R^1$ is trans-4-hydroxycyclohexyl; m is 2, n is 2, $R^2$=H and the radical $R^1$—C(=O)—NH and the radical $R^2$ have cis-configuration)

Example 22 trans-N-[cis-4-[2-[4-(2,6-ditert-butylpyrimidin-4-yl)piperazin-1-yl]ethyl]cyclohexyl]-4-hydroxy-cyclohexanecarboxamide (compound 22; compound of the formula I, where $R^1$ is trans-4-hydroxycyclohexyl; m is 2, n is 2, $R^2$=H and the radical $R^1$—C(=O)—NH and the radical $R^2$ have trans-configuration)

Example 23

Trans-N-[cis-4-[2-[4-[2-tert-butyl-6-(trifluoromethyl)pyrimidin-4-yl]piperazin-1-yl]ethyl]cyclohexyl]-4-hydroxy-cyclohexanecarboxamide (compound 23; compound of the formula I, where $R^1$ is trans-4-hydroxycyclohexyl; m is 2, n is 2, $R^2$=H and the radical $R^1$—C(=O)—NH and the radical $R^2$ have trans-configuration)

Example 24 trans-N-[trans-4-[2-[4-[2-tert-butyl-6-(2-methoxyethyl)pyrimidin-4-yl]piperazin-1-yl]ethyl]cyclohexyl]-4-methoxy-cyclohexanecarboxamide (compound 24; compound of the formula I, where $R^1$ is trans-4-methoxycyclohexyl; m is 2, n is 2, $R^2$=H and the radical $R^1$—C(=O)—NH and the radical $R^2$ have cis-configuration)

Example 25

N-[trans-4-[2-[4-[2-tert-butyl-6-(2-methoxyethyl)pyrimidin-4-yl]piperazin-1-yl]ethyl]cyclohexyl]-3-hydroxy-3-(trifluoromethyl)cyclobutanecarboxamide (compound 25; compound of the formula I, where $R^1$ is 3-hydroxy-3-trifluoromethylcyclobutyl, m is 2, n is 2, $R^2$=H and the radical $R^1$—C(=O)—NH and the radical $R^2$ have cis-configuration)

Example 26

N-[cis-4-[2-[4-[2-tert-butyl-6-(2-methoxyethyl)pyrimidin-4-yl]piperazin-1-yl]ethyl]cyclohexyl]-3-hydroxy-3-(trifluoromethyl)cyclobutanecarboxamide (compound 26; compound of the formula I, where $R^1$ is 3-hydroxy-3-trifluoromethylcyclobutyl, m is 2, n is 2, $R^2$=H and the radical $R^1$—C(=O)—NH and the radical $R^2$ have trans-configuration)

Example 27

N-[4-[2-[4-[2-tert-butyl-6-(1-methylcyclopropyl)pyrimidin-4-yl]piperazin-1-yl]ethyl]cyclohexyl]-4-hydroxy-cyclohexanecarboxamide (compound 27; compound of the formula I, where $R^1$ is 4-hydroxycyclohexyl; m is 2, n is 2, $R^2$=H)

Example 28

Trans-N-[cis-4-[2-[4-[2-tert-butyl-6-(1-methylcyclopropyl)pyrimidin-4-yl]piperazin-1-yl]ethyl]cyclohexyl]-4-hydroxy-cyclohexanecarboxamide (compound 28; compound of the formula I, where $R^1$ is trans-4-hydroxycyclohexyl; m is 2, n is 2, $R^2$=H and the radical $R^1$—C(=O)—NH and the radical $R^2$ have trans-configuration)

Example 29

N-[4-[2-[4-[2-tert-butyl-6-(difluoromethyl)pyrimidin-4-yl]piperazin-1-yl]ethyl]cyclohexyl]-4-hydroxy-cyclohexanecarboxamide (compound 29; compound of the formula I, where $R^1$ is 4-hydroxycyclohexyl; m is 2, n is 2, $R^2$=H)

Example 30

Trans-N-[cis-4-[2-[4-[2-tert-butyl-6-(difluoromethyl)pyrimidin-4-yl]piperazin-1-yl]ethyl]cyclohexyl]-4-hydroxy-cyclohexanecarboxamide (compound 30; compound of the formula I, where $R^1$ is trans-4-hydroxycyclohexyl; m is 2, n is 2, $R^2$=H and the radical $R^1$—C(=O)—NH and the radical $R^2$ have trans-configuration)

Example 31

N-[4-[2-[4-(2-tert-butyl-6-isopropyl-pyrimidin-4-yl)piperazin-1-yl]ethyl]cyclohexyl]-4-hydroxy-cyclohexanecarboxamide (compound 31; compound of the formula I, where $R^1$ is 4-hydroxycyclohexyl; m is 2, n is 2, $R^2$=H)

Example 32

Trans-N-[trans-4-[2-[4-(2-tert-butyl-6-isopropyl-pyrimidin-4-yl)piperazin-1-yl]ethyl]cyclohexyl]-4-hydroxy-cyclohexanecarboxamide (compound 32; compound of the formula I, where $R^1$ is trans-4-hydroxycyclohexyl; m is 2, n is 2, $R^2$=H and the radical $R^1$—C(=O)—NH and the radical $R^2$ have cis-configuration)

Example 33

N-[4-[2-[(3R)-4-[2-tert-butyl-6-(2-methoxyethyl)pyrimidin-4-yl]-3-methyl-piperazin-1-yl]ethyl]cyclohexyl]-4-hydroxy-cyclohexanecarboxamide (compound 33; compound of the formula I, where $R^1$ is 4-hydroxycyclohexyl; m is 2, n is 2, $R^2$=H)

Example 34 trans-N-[trans-4-[2-[(3R)-4-[2-tert-butyl-6-(2-methoxyethyl)pyrimidin-4-yl]-3-methyl-piperazin-1-yl]ethyl]cyclohexyl]-4-hydroxy-cyclohexanecarboxamide (compound 34; compound of the formula I, where $R^1$ is trans-4-hydroxycyclohexyl; m is 2, n is 2, $R^2$=H and the radical $R^1$—C(=O)—NH and the radical $R^2$ have cis-configuration)

Example 35 trans-N-[trans-4-[2-[4-(2-tert-butyl-6-cyclopentyl-pyrimidin-4-yl)piperazin-1-yl]ethyl]cyclohexyl]-4-hydroxy-cyclohexanecarboxamide (compound 35; compound of the formula I, where $R^1$ is trans-4-hydroxycyclohexyl; m is 2, n is 2, $R^2$=H and the radical $R^1$—C(=O)—NH and the radical $R^2$ have cis-configuration)

Example 36 trans-N-[cis-4-[2-[4-(2-tert-butyl-6-cyclopentyl-pyrimidin-4-yl)piperazin-1-yl]ethyl]cyclohexyl]-4-hydroxy-cyclohexanecarboxamide (compound 36; compound of the formula I, where $R^1$ is trans-4-hydroxycyclohexyl; m is 2, n is 2, $R^2$=H and the radical $R^1$—C(=O)—NH and the radical $R^2$ have trans-configuration)

Example 37 trans-N-[trans-4-[2-[4-[2-tert-butyl-6-(methoxymethyl)pyrimidin-4-yl]piperazin-1-yl]ethyl]cyclohexyl]-4-hydroxy-cyclohexanecarboxamide (compound 37; compound of the formula I, where $R^1$ is trans-4-hydroxycyclohexyl; m is 2, n is 2, $R^2$=H and the radical $R^1$—C(=O)—NH and the radical $R^2$ have cis-configuration)

Example 38 trans-N-[trans-4-[2-[4-(2-tert-butyl-6-cyclobutyl-pyrimidin-4-yl)piperazin-1-yl]ethyl]cyclohexyl]-3-hydroxy-cyclobutanecarboxamide; 2,2,2-trifluoroacetic acid (compound 38; compound of the formula I, where $R^1$ is trans-3-hydroxy-cyclobutyl; m is 2, n is 2, $R^2$=H and the radical $R^1$—C(=O)—NH and the radical $R^2$ have cis-configuration)

Example 39 trans-N-[trans-3-[2-[4-(2-tert-butyl-6-cyclobutyl-pyrimidin-4-yl)piperazin-1-yl]ethyl]cyclobutyl]-3-hydroxy-cyclobutanecarboxamide; 2,2,2-trifluoroacetic acid (compound 39; compound of the formula I, where $R^1$ is trans-3-hydroxy-cyclobutyl; m is 1, n is 1, $R^2$=H and the radical $R^1$—C(=O)—NH and the radical $R^2$ have cis-configuration)

Example 40 cis-N-[trans-4-[2-[4-[2-tert-butyl-6-(methoxymethyl)pyrimidin-4-yl]piperazin-1-yl]ethyl]cyclohexyl]-3-hydroxy-cyclobutanecarboxamide (compound 40; compound of the formula I, where $R^1$ is cis-3-hydroxycyclobutyl; m is 2, n is 2, $R^2$=H and the radical $R^1$—C(=O)—NH and the radical $R^2$ have cis-configuration)

Example 41

Trans-N-[4-[2-[(3S)-4-(2-tert-butyl-6-isopropyl-pyrimidin-4-yl)-3-methyl-piperazin-1-yl]ethyl]cyclohexyl]-trans-4-hydroxy-cyclohexanecarboxamide (compound 41, compound of the formula I, where $R^1$ is trans-4-hydroxycyclohexyl; m is 2, n is 2, $R^2$=H, $R^{3b}$ is (S) methyl and the radical $R^1$—C(=O)—NH and the radical $R^2$ have cis-configuration)

LCMS: m/z 528.4 (M+H)

$^1$H-NMR (CDCl$_3$, 400 MHz): δ: 6.1 (s, 1H), 5.23 (d, 1H), 4.55 (m, 1H), 4.15 (m, 1H), 3.7 (m, 1H), 3.62 (m, 1H), 3.13 (m, 1H), 2.9 (m, 1H), 2.78 (m, 2H), 2.4 (m, 1H), 2.3 (m, 1H), 2.2 (m, 1H), 1.85-2.1 (several m, 10H), 1.8 (m, 2H), 1.2-1.6 (broad, several m, 5H), 1.55 (m, 2H), 1.4 (m, 2H), 1.3 (s, 9H), 1.25 (m, 6H), 1.1 (m, 3H).

Example 42

N-[3-2-[(3S)-4-(2-tert-butyl-6-isopropyl-pyrimidin-4-yl)-3-methyl-piperazin-1-yl]ethyl]cyclobutyl]-trans-4-hydroxy-cyclohexanecarboxamide (compound 42, compound of the formula I, where $R^1$ is trans-4-hydroxycyclohexyl; m is 1, n is 1, $R^2$=H, $R^{3b}$ is (S)-methyl and the radical $R^1$—C(=O)—NH and the radical $R^2$ have trans-configuration)

LCMS: m/z 500.3 (M+H)

$^1$H-NMR (CDCl$_3$, 400 MHz): δ: 6.08 (s, 1H), 5.5 (d, 1H), 4.55 (m, 1H), 4.25 (m, 1H), 4.15 (m, 1H), 3.6 (m, 1H), 3.12 (m, 1H), 2.88 (m, 1H), 2.7-2.85 (m, 2H), 2.55 (m, 2H), 2.3 (m, 1H), 2.2 (m, 2H), 1.8-2.1 (several m, 7H), 1.35-1.7 (several m, 9H), 1.33 (s, 9H), 1.28 (m, 2H), 1.2 (d, 6H).

Example 43

Cis-N-[4-[2-[4-(2 tert-butyl-6-isopropyl-pyrimidin-4-yl)piperazin-1-yl]ethyl]cyclohexyl]-trans-4-hydroxy-cyclohexanecarboxamide (compound 43, compound of the formula I, where $R^1$ is trans-4-hydroxycyclohexyl; m is 2, n is 2, $R^2$=H, and the radical $R^1$—C(=O)—NH and the radical $R^2$ have trans-configuration)

LCMS: m/z 514.5 (M+H)

$^1$H-NMR (CDCl$_3$, 600 MHz): δ: 6.14 (s, 1H), 5.49 (d, J=7.5 Hz, 1H), 3.97-4.05 (m, 1H), 3.60-3.69 (m, 5H), 2.81 (spt, J=6.9 Hz, 1H), 2.52 (t, J=5.1 Hz, 4H), 2.40 (dd, J=8.8, 6.6 Hz, 2H), 2.03-2.1 (m, 2H), 1.98-1.99 (m, 1H), 1.87-1.94 (m, 2H), 1.59-1.65 (m, 5H), 1.57 (d, J=3.4 Hz, 1H), 1.55 (d, J=3.2 Hz, 1H), 1.48-1.54 (m, 3H), 1.45-1.47 (m, 1H), 1.33 (s, 9H), 1.28-1.34 (m, 1H), 1.23 (d, J=6.8 Hz, 6H), 1.18-1.26 (m, 2H).

Example 44

Cis-N-[4-[2-[(3S)-4-[2-tert-butyl-6-(difluoromethyl)pyrimidin-4-yl]-3-methyl-piperazin-1-yl]ethyl]cyclohexyl]-trans-4-hydroxy-cyclohexanecarboxamide (compound 44, compound of the formula I, where $R^1$ is trans-4-hydroxycyclohexyl; m is 2, n is 2, $R^2$=H, $R^{3b}$ is (S) methyl, and the radical $R^1$—C(=O)—NH and the radical $R^2$ have trans-configuration)

LCMS: m/z 536.5 (M+H)

$^1$H-NMR (CD$_3$OD, 400 MHz): δ: 7.7 (d, 1H), 6.7 (s, 1H), 6.47 (t, 1H, CHF$_2$), 4.7 (m, 1H), 4.3 (m, 1H), 3.85 (m, 1H), 3.5 (m, 1H), 3.3 (m, 2H), 3.2 (m, 1H), 3.05 (m, 1H), 2.95 (m, 1H), 2.4 (m, 1H), 2.23 (m, 2H), 2.1 (m, 1H), 2.03 (m, 2H), 1.8 (m, 2H), 1.2-2.7 (several m, 13H), 1.35 (s, 9H), 1.28 (d, 3H), 0.92 (m, 1H).

Example 45

Trans-N-[(1S)-3-[2-[(3S)-4-(2-tert-butyl-6-isopropyl-pyrimidin-4-yl)-3-methyl-piperazin-1-yl]ethyl]cyclopentyl]-4-hydroxy-cyclohexanecarboxamide (compound 45, compound of the formula I, where $R^1$ is trans-4-hydroxycyclohexyl, m is 2, n is 1, $R^2$=H, $R^{3a}$ is H, $R^{3b}$ is (S) methyl, A is CH$_2$, $R^4$ is tert.butyl, $R^5$ is isopropyl, and the radical $R^1$—C(=O)—NH and the radical $R^2$ have trans-configuration)

LCMS: m/z 514.4 (M+H)

Example 46

Trans-N-[4-2-[(3S)-4-(2-tert-butyl-6-isopropyl-pyrimidin-4-yl)-3-methyl-piperazin-1-yl]ethyl]cyclohexyl]-4-hydroxy-cyclohexanecarboxamide (compound 46, compound of the formula I, where $R^1$ is trans-4-hydroxycyclohexyl, m is 2, n is 2, $R^2$=H, $R^{3a}$ is H, $R^{3b}$ is (S) methyl, A is CH$_2$, $R^4$ is tert.butyl, $R^5$ is isopropyl, and the radical $R^1$—C(=O)—NH and the radical $R^2$ have trans-configuration)

LCMS: m/z 528.4 (M+H)

$^1$H NMR (CHLOROFORM-d, 600 MHz): δ=6.1 (s, 1H), 5.5 (d, 1H), 4.55 (m, 1H), 4.15 (m, 1H), 4.0 (m, 1H), 3.65 (m, 1H), 3.12 (m, 1H), 2.9 (m, 1H), 2.8 (m, 2H), 2.4 (m, 1H), 2.3 (m, 1H), 2.18 (m, 1H), 1.98-2.1 (several m, 4H), 1.92 (m, 1H), 1.4-1.7 (several m, 14H), 1.32 (s, 9H), 1.3 (m, 2H), 1.22 (d, 6H), 1.2 (m, 2H).

Example 47

Trans-N-[4-[2-[(3S)-4-(2-tert-butyl-6-isopropyl-pyrimidin-4-yl)-3-methyl-piperazin-1-yl]ethyl]cyclohexyl]-3-methoxy-cyclobutanecarboxamide (compound 48, compound of the formula I, where $R^1$ is trans-3-methoxycyclobutyl, m is 2, n is 2, $R^2$=H, $R^{3a}$ is H, $R^{3b}$ is (S) methyl, A is CH$_2$, $R^4$ is tert.butyl, $R^5$ is isopropyl, and the radical $R^1$—C(=O)—NH and the radical $R^2$ have trans-configuration)

LCMS: m/z 514.4 (M+H)

$^1$H-NMR (CDCl$_3$, 600 Hz): δ [ppm] 6.1 (s, 1H), 5.2 (d, 1H), 4.56 (broad, 1H), 4.13 (m, 1H), 3.72 (m, 1H), 3.24, (s, 3H), 3.15 (m, 1H), 2.90 (m, 1H), 2.82 (m, 2H), 2.47 (m, 2H), 2.39 (m, 1H), 2.29 (m, 1H), 2.17 (m, 3H), 2.04 (m, 1H), 1.98 (m, 2H), 1.89 (m, 2H), 1.44 (m, 2H), 1.34 (s, 9H), 1.2-1.35 (m, 11H), 1.08 (m, 4H).

Example 48

Trans-N-[4-[2-[(3S)-4-(2-tert-butyl-6-isopropyl-pyrimidin-4-yl)-3-methyl-piperazin-1-yl]ethyl]cyclohexyl]-3-hydroxycyclobutanecarboxamide (compound 48, compound of the formula I, where $R^1$ is trans-3-hydroxycyclobutyl, m is 2, n is 2, $R^2$=H, $R^{3a}$ is H, $R^{3b}$ is (S) methyl, A is CH$_2$, $R^4$ is tert.butyl, $R^5$ is isopropyl, and the radical $R^1$—C(=O)—NH and the radical $R^2$ have trans-configuration)

The title compound was prepared by O-demethylation of the corresponding 3-methoxy-cyclobutyl-carboxamide of example 47 with BBr₃ and subsequent purification.

LCMS: m/z 500.5 (M+H)

Example 49

Trans-N-[4-[2-[4-(2-tert-butyl-6-isopropyl-pyrimidin-4-yl)-piperazin-1-yl]ethyl]cyclohexyl]-3-methoxy-cyclobutanecarboxamide (compound 49, compound of the formula I, where $R^1$ is trans-3-methoxycyclobutyl, m is 2, n is 2, $R^2$=H, $R^{3a}$ is H, $R^{3b}$ is H, A is $CH_2$, $R^4$ is tert.butyl, $R^5$ is isopropyl, and the radical $R^1$—C(=O)—NH and the radical $R^2$ have trans-configuration)

LCMS: m/z 500.4 (M+H)

¹H-NMR (CDCl₃, 600 Hz): δ [ppm] 6.13 (s, 1H), 5.19 (d, 1H), 4.11 (m, 1H), 3.72 (m, 1H), 3.65 (m, 4H), 3.24, (s, 3H), 2.81 (m, 2H), 2.45-2.55 (m, 5H), 2.4 (m, 2H), 2.17 (m, 2H), 1.98 (m, 2H), 1.78 (m, 2H), 1.44 (m, 2H), 1.33 (s, 9H), 1.2-1.28 (m, 7H), 1.08 (m, 4H).

Example 50

Trans-N-[4-[2-[4-(2-tert-butyl-6-isopropyl-pyrimidin-4-yl)-piperazin-1-yl]ethyl]cyclohexyl]-3-hydroxy-cyclobutanecarboxamide (compound 50, compound of the formula I, where $R^1$ is trans-3-hydroxycyclobutyl, m is 2, n is 2, $R^2$=H, $R^{3a}$ is H, $R^{3b}$ is H, A is $CH_2$, $R^4$ is tert.butyl, $R^5$ is isopropyl, and the radical $R^1$—C(=O)—NH and the radical $R^2$ have trans-configuration)

The title compound was prepared by O-demethylation of the corresponding 3-methoxy-cyclobutyl-carboxamide of example 49 with BBr₃ and subsequent purification.

LCMS: m/z 486.4 (M+H)

¹H NMR (CHLOROFORM-d, 600 MHz): δ=6.14 (s, 1H), 5.2 (d, J=7.5 Hz, 1H), 4.62 (m, 1H), 3.60-3.8 (broad, 4H), 2.8 (m, 2H), 2.52 (m, 2H), 2.45 (m, broad, 2H), 2.17 (m, 2H), 1.97 (m, 2H), 1.7 (m, 2H), 1.57 (m, 7H), 1.3 (s, 9H), 1.2 (m, 6H), 1.1 (m, 4H).

IV. Biological Investigations

1. Receptor Binding Studies

The substance to be tested was either dissolved in methanol/Chremophor® (BASF SE) or in dimethyl sulfoxide and then diluted with water to the desired concentration.

a) Dopamine D₃ receptor:
The assay mixture (0.250 ml) was composed of membranes derived from ~10⁶ HEK-293 cells possessing stably expressed human dopamine D₃ receptors, 0.1 nM [¹²⁵I]-iodosulpride and incubation buffer (total binding) or, in addition, test substance (inhibition curve) or 1 μM spiperone (nonspecific binding). Each assay mixture was run in triplicate.

The incubation buffer contained 50 mM tris, 120 mM NaCl, 5 mM KCl, 2 mM CaCl₂, 2 mM MgCl₂ and 0.1% bovine serum albumin, 10 μM quinolone and 0.1% ascorbic acid (prepared fresh daily). The buffer was adjusted to pH 7.4 with HCl.

b) Dopamine D₂L receptor:
The assay mixture (1 ml) was composed of membranes from ~10⁶ HEK-293 cells possessing stably expressed human dopamine D₂L receptors (long isoform) and 0.01 nM [¹²⁵I] iodospiperone and incubation buffer (total binding) or, in addition, test substance (inhibition curve) or 1 μM haloperidol (nonspecific binding). Each assay mixture was run in triplicate.

The incubation buffer contained 50 mM tris, 120 mM NaCl, 5 mM KCl, 2 mM CaCl₂, 2 mM MgCl₂ and 0.1% bovine serum albumin. The buffer was adjusted to pH 7.4 with HCl.

c) Measurement and analysis:
After having been incubated at 25° C. for 60 minutes, the assay mixtures were filtered through a Whatman GF/B glass fiber filter under vacuum using a cell col-lecting device. The filters were transferred to scintillation viols using a filter transfer system. After 4 ml of Ultima Gold® (Packard) have been added, the samples were shaken for one hour and the radioactivity was then counted in a Beta-Counter (Packard, Tricarb 2000 or 2200CA). The cpm values were con-verted into dpm using a standard quench series and the program belonging to the instrument.

The inhibition curves were analyzed by means of iterative nonlinear regression analysis using the Statistical Analysis System (SAS) which is similar to the "LIGAND" program described by Munson and Rodbard.

In these tests, the compounds according to the invention exhibit very good affinities for the D₃ receptor (<100 nM, frequently <50 nM, in particular <10 nM) and bind selectively to the D₃ receptor.

The results of the binding tests are given in Table 1.

TABLE 1

| Compound | D3 $K_i$ | D2/D3 |
|---|---|---|
| 1 | +++ | +++ |
| 2 | +++ | ++ |
| 3 | +++ | ++ |
| 4 | +++ | ++ |
| 5 | ++ | ++ |
| 6 | +++ | +++ |
| 7 | +++ | +++ |
| 8 | +++ | +++ |
| 9 | +++ | +++ |
| 10 | +++ | +++ |
| 11 | +++ | ++ |
| 12 | ++ | +++ |
| 13 | +++ | ++ |
| 14 | +++ | ++ |
| 15 | +++ | +++ |
| 16 | +++ | ++ |
| 17 | +++ | +++ |
| 18 | +++ | +++ |
| 19 | +++ | + |
| 20 | +++ | ++ |
| 21 | +++ | ++ |
| 22 | ++ | +++ |
| 23 | ++ | +++ |
| 24 | ++ | ++ |
| 25 | +++ | ++ |
| 26 | ++ | +++ |
| 27 | +++ | ++ |
| 28 | +++ | ++ |
| 29 | +++ | + |
| 30 | +++ | ++ |
| 31 | +++ | ++ |
| 32 | +++ | ++ |
| 33 | ++ | +++ |
| 34 | +++ | +++ |
| 35 | +++ | + |
| 36 | +++ | +++ |
| 37 | +++ | +++ |
| 38 | +++ | ++ |
| 39 | +++ | +++ |
| 41 | +++ | +++ |
| 42 | +++ | +++ |
| 43 | +++ | +++ |

TABLE 1-continued

| Compound | D3 $K_i$ | D2/D3 |
|---|---|---|
| 44 | +++ | +++ |
| 45 | +++ | +++ |
| 46 | +++ | +++ |
| 47 | +++ | +++ |
| 48 | +++ | +++ |
| 49 | +++ | +++ |
| 50 | +++ | +++ |

$K_i$ (D$_3$): +++ <10 nM, ++ <50 nM, + <100 nM
$K_i$ (D$_{2L}$)/$K_i$ (D$_3$): +++ >50, ++ >20, + >10

2. Determination of the Microsomal Half-Life

The metabolic stability of the compounds of the invention was determined in the following assay.

The test substances were incubated in a concentration of 0.5 µM as follows:

0.5 µM test substance are preincubated together with liver microsomes from different species (from rat, human or other species) (0.25 mg of microsomal protein/ml) in 0.05 M potassium phosphate buffer of pH 7.4 in microtiter plates at 37° C. for 5 min. The reaction is started by adding NADPH (1 mg/mL). After 0, 5, 10, 15, 20 and 30 min, 50 µl aliquots are removed, and the reaction is immediately stopped and cooled with the same volume of acetonitrile. The samples are frozen until analyzed. The remaining concentration of undegraded test substance is determined by MSMS. The half-life (T1/2) is determined from the gradient of the signal of test substance/unit time plot, it being possible to calculate the half-life of the test substance, assuming first order kinetics, from the decrease in the concentration of the compound with time. The microsomal clearance (mC1) is calculated from mC1=1n2/T1/2/(content of microsomal protein in mg/ml)×1000 [ml/min/mg] (modified from references: Di, The Society for Biomoleculur Screening, 2003, 453-462; Obach, DMD, 1999 vol 27. N 11, 1350-1359). The results are shown in Table 2.

TABLE 2

| Compound | Human mCl[2)] [µl min$^{-1}$ mg$^{-1}$] |
|---|---|
| 1 | + |
| 2 | + |
| 3 | + |
| 4 | o |
| 5 | o |
| 6 | + |
| 7 | + |
| 8 | + |
| 9 | + |
| 10 | + |
| 11 | + |
| 12 | + |
| 13 | o |
| 14 | o |
| 15 | o |
| 16 | o |
| 17 | o |
| 18 | + |
| 19 | + |
| 20 | + |
| 21 | + |
| 22 | + |
| 23 | + |
| 24 | o |
| 25 | o |
| 26 | ++ |
| 27 | + |
| 28 | + |
| 29 | + |

TABLE 2-continued

| Compound | Human mCl[2)] [µl min$^{-1}$ mg$^{-1}$] |
|---|---|
| 30 | + |
| 31 | + |
| 32 | + |
| 33 | + |
| 34 | + |
| 35 | + |
| 36 | + |
| 37 | + |
| 38 | ++ |
| 39 | ++ |
| 40 | + | mCl mikrosomal clearance
[2)] ++: <20 µl min$^{-1}$ mg$^{-1}$
+: 20-120 µl min$^{-1}$ mg$^{-1}$
o: >120 µl min$^{-1}$ mg$^{-1}$

3. Blocking the hERG Channel

The binding affinity of test drugs for the hERG cardiac K$^+$ channel was determined by their ability to displace tritiated dofetilide (a class III antiarrhythmic drug and potent hERG blocker) in membrane homogenates from HEK-293 cells heterogeneously expressing the hERG channel. The assay was performed as previously described G. J. Diaz et al., Journal of Pharmacological and Toxicological Methods, 50 (2004), 187-199). For this, drug dilutions were prepared from 10 mM DMSO stocks and the following were added to a 96-well polystyrene plate (Perkin-Elmer Optiplate): 20 µl of assay binding buffer (for total bounds), or 1 µM astemizole (for non-specific bounds), or test drug, 50 µl of [$^3$H]dofetilide (20 nM, ~80 Ci/mmol specific activity), and 130 µl of membrane homogenate from HEK 293 cells stably transfected with hERG K$^+$ channels (final protein concentration of 30 µg per well). The plates were incubated at ambient temperature for 45 min, aspirated onto GF/B filter plates (Perkin-Elmer), and washed with 2 ml of cold wash buffer. After allowing the plates to dry, 50 µl of scintillant (Per-kin-Elmer MicroScint 20) were added to each well and the radioactivity was counted in a Perkin-Elmer Topcount NXT scintillation counter. IC$_{50}$ determinations were calculated from competition curves using 6 drug concentrations, half-log apart, starting at a high concentration of 100 µM (final assay DMSO concentration=1%) using a four-parameter logistic equation. The results are given as IC$_{50}$ value. The compound of example 1 showed an IC$_{50}$ of >10 µm.

We claim:

1. A compound, selected from the group consisting of
   Trans-N-[4-[2-[(3S)-4-(2-tert-butyl-6-isopropyl-pyrimidin-4-yl)-3-methyl-piperazin-1-yl]ethyl]cyclohexyl]-trans-4-hydroxy-cyclohexanecarboxamide;
   N-[3-[2-[(3S)-4-(2-tert-butyl-6-isopropyl-pyrimidin-4-yl)-3-methyl-piperazin-1-yl]ethyl]cyclobutyl]-trans-4-hydroxy-cyclohexanecarboxamide;
   Cis-N-[4-[2-[4-(2-tert-butyl-6-isopropyl-pyrimidin-4-yl)piperazin-1-yl]ethyl]cyclohexyl]-trans-4-hydroxy-cyclohexanecarb oxamide;
   Cis-N-[4-[2-[(3S)-4-[2-tert-butyl-6-(difluoromethyl)pyrimidin-4-yl]-3-methyl-piperazin-1-yl]ethyl]cyclohexyl]-trans-4-hydroxy-cyclohexanecarboxamide;
   trans-N-[(1S)-3-[2-[(3S)-4-(2-tert-butyl-6-isopropyl-pyrimidin-4-yl)-3-methyl-piperazin-1-yl]ethyl]cyclopentyl]-4-hydroxy-cyclohexanecarboxamide;
   trans-N-[4-[2-[(3S)-4-(2-tert-butyl-6-isopropyl-pyrimidin-4-yl)-3-methyl-piperazin-1-yl]ethyl]cyclohexyl]-4-hydroxy-cyclohexanecarboxamide;

trans-N-[4-[2-[(3S)-4-(2-tert-butyl-6-isopropyl-pyrimidin-4-yl)-3-methyl-piperazin-1-yl]ethyl]cyclohexyl]-3-methoxy-cyclobutanecarboxamide;

trans-N-[4-[2-[(3S)-4-(2-tert-butyl-6-isopropyl-pyrimidin-4-yl)-3-methyl-piperazin-1-yl]ethyl]cyclohexyl]-3-hydroxy-cyclobutanecarboxamide;

trans-N-[4-[2-[4-(2-tert-butyl-6-isopropyl-pyrimidin-4-yl)-piperazin-1-yl]ethyl]cyclohexyl]-3-methoxy-cyclobutanecarboxamide; and trans-N-[4-[2-[4-(2-tert-butyl-6-isopropyl-pyrimidin-4-yl)-piperazin-1-yl]ethyl]cyclohexyl]-3-hydroxy-cyclobutanecarboxamide;

or an N-oxide, or a pharmaceutically acceptable salt thereof.

2. A pharmaceutical composition comprising at least one compound as claimed in claim 1, optionally together with at least one physiologically acceptable carrier or auxiliary substance.

3. A method for treating a medical disorder or condition selected from the group consisting of Parkinson's disease, schizophrenia, depression, anxiety, and diabetic nephropathy, said method comprising administering an effective amount of at least one compound as claimed in claim 1, to a subject in need thereof.

4. A method for treating a medical disorder or condition selected from the group consisting of amotivation, anorexia and drug addiction, said method comprising administering an effective amount of at least one compound as claimed in claim 1 to a subject in need thereof.

5. A method for treating Parkinson's disease, said method comprising administering an effective amount of at least one compound as claimed in claim 1 to a subject in need thereof.

6. A method for treating diabetic nephropathy, said method comprising administering an effective amount of at least one compound as claimed in claim 1 to a subject in need thereof.

* * * * *